(12) United States Patent
Barrett et al.

(10) Patent No.: US 9,120,820 B2
(45) Date of Patent: Sep. 1, 2015

(54) FLUORESCENT MOLECULAR PROBES FOR USE IN ASSAYS THAT MEASURE TEST COMPOUND COMPETITIVE BINDING WITH SAM-UTILIZING PROTEINS

(75) Inventors: Stephen Douglas Barrett, Hartland, MI (US); Daniel Austin Bochar, Ann Arbor, MI (US); Levi Lynn Blazer, Ann Arbor, MI (US); Fred Lawrence Ciske, Dexter, MI (US); Gregory William Endres, Saline, MI (US); Jeffrey Keith Johnson, Ann Arbor, MI (US); Gregory Scott Keyes, Dexter, MI (US); Ranjinder Singh Sidhu, Ann Arbor, MI (US); Raymond C. Trievel, Ypsilanti, MI (US); Margaret Lynn Collins, Canton, MI (US)

(73) Assignees: CAYMAN CHEMICAL COMPANY, INCORPORATED, Ann Arbor, MI (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 291 days.

(21) Appl. No.: 13/475,618

(22) Filed: May 18, 2012

(65) Prior Publication Data
US 2012/0295283 A1 Nov. 22, 2012

Related U.S. Application Data

(60) Provisional application No. 61/487,461, filed on May 18, 2011.

(51) Int. Cl.
*C07D 519/00* (2006.01)
*G01N 21/64* (2006.01)
(52) U.S. Cl.
CPC .......... *C07D 519/00* (2013.01); *G01N 21/6428* (2013.01)

(58) Field of Classification Search
None
See application file for complete search history.

(56) References Cited

U.S. PATENT DOCUMENTS

2007/0281902 A1 * 12/2007 Baraldi et al. .................. 514/47

FOREIGN PATENT DOCUMENTS

WO WO 2012/016704 A1 2/2012

OTHER PUBLICATIONS

STN Registry Entry for CAS RN 134618-13-6; Entered STN Registry Jun. 28, 1991; Accessed Feb. 4, 2015.*

* cited by examiner

*Primary Examiner* — Alicia L Otton
(74) *Attorney, Agent, or Firm* — Howard & Howard Attorneys PLLC

(57) ABSTRACT

Assay methods may generally comprise forming homogeneous assay mixtures comprising target SAM-utilizing protein, fluorescent detection analyte, and test compound, incubating, and measuring FP or TR-FRET signal emitted in order to determine a measure of test compound-SAM-utilizing protein binding. Assay mixtures comprise a SAM-utilizing protein, and a fluorescent detection analyte that binds with the SAM-utilizing protein in the absence of test compound. Assay mixtures may further comprise a test compound. Assay mixture embodiments may generate FP or TR-FRET signal properties that are a function of the inherent binding interactions of both the test compound and the detection analyte with the SAM-utilizing protein. Fluorescent detection analytes comprise a fluorophore moiety, a covalent linker moiety, and a SAM-utilizing protein ligand moiety and could be utilized in FP or TR-FRET assays to measure test compound binding.

7 Claims, 14 Drawing Sheets

FIGURE 4
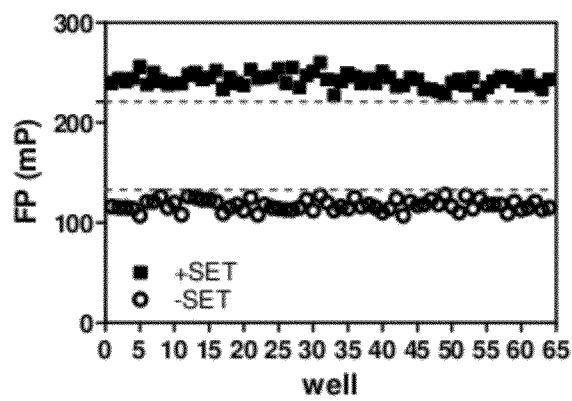
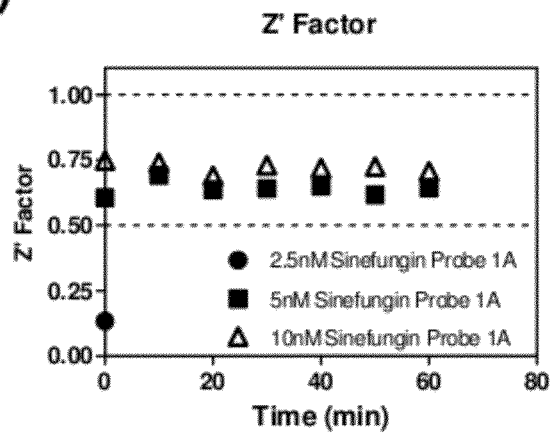

FIGURE 7
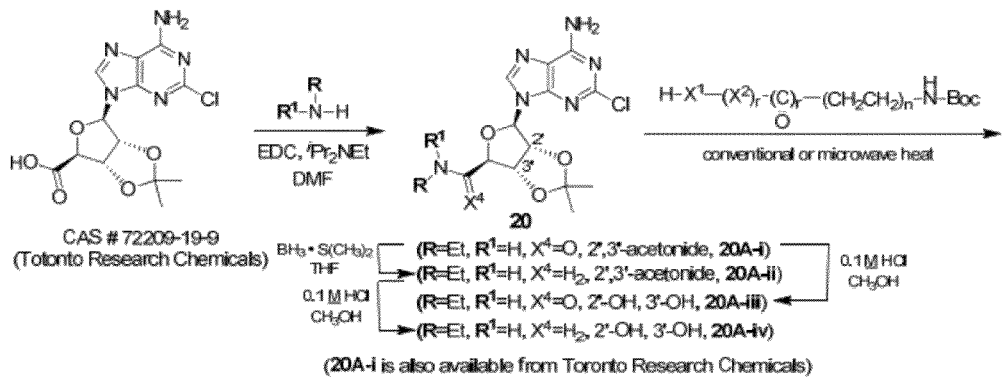
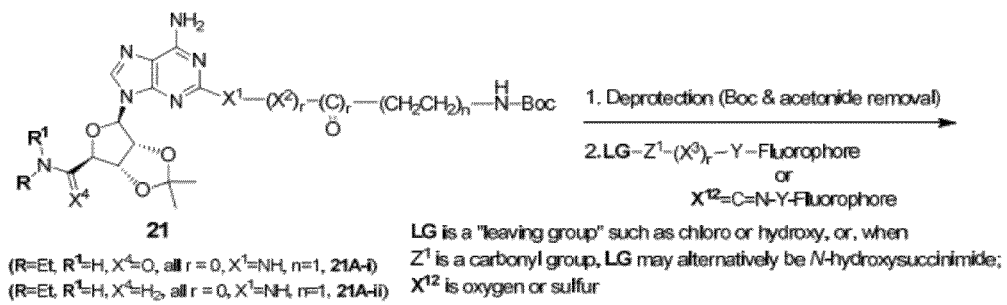
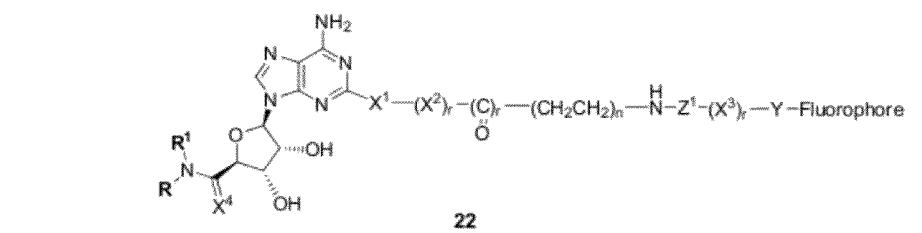

FLUORESCENT MOLECULAR PROBES FOR USE IN ASSAYS THAT MEASURE TEST COMPOUND COMPETITIVE BINDING WITH SAM-UTILIZING PROTEINS

CROSS REFERENCE TO RELATED APPLICATIONS

The present application claims priority from U.S. Provisional Application Ser. No. 61/487,461, filed May 18, 2011, which is herein incorporated by reference.

GOVERNMENT CONTRACT

This invention was made with government support under GM073839 awarded by the National Institute of Health. The government has certain rights in this invention.

FIELD OF THE INVENTION

The subject matter disclosed and claimed herein centers on fluorescent molecular probes that may be used as detection analytes in binding assay mixtures and the use of the assay mixtures for measuring test compound binding to SAM-utilizing proteins.

BACKGROUND OF THE INVENTION

All references, including patents and patent applications, are hereby incorporated by reference in their entireties.

S-Adenosylmethionine (SAM) is a ubiquitous metabolic intermediate that is biosynthesized by the enzyme methionine adenosyltransferase (SAM synthetase), which accelerates the coupling of adenosine triphosphate (ATP) with methionine (Mato, J. M., *Pharmacology and Therapeutics*, 1997, 73(3), 265-280). SAM plays a key role in various biochemical processes such as enzymatic reactions that involve transmethylation, transsulfuration, and the polyamine-generating aminoalkylation pathway (Roje, S., *Phytochemistry*, 2006, 67(15), 1686-1698; Giulidori, P. et al., *The Journal of Biological Chemistry*, 1984, 259(7), 4205-4211). Other enzymatic reactions that involve interaction of proteins with SAM or isostructural SAM analogs include transfer of methylene, ribosyl, and 5'-deoxyadenosyl groups; formation of redox intermediate 5'-deoxyadenosyl radical; and SAM decarboxylation. SAM-nonenzymatic protein interactions also exist wherewith SAM acts as a ligand affecting structural and functional modification in the effector protein (Kozbial, P. Z. and Mushegian, A. R., *BMC Structural Biology*, 2005, 5, 19-44).

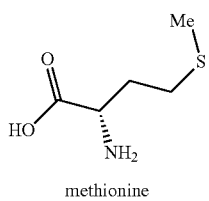

methionine

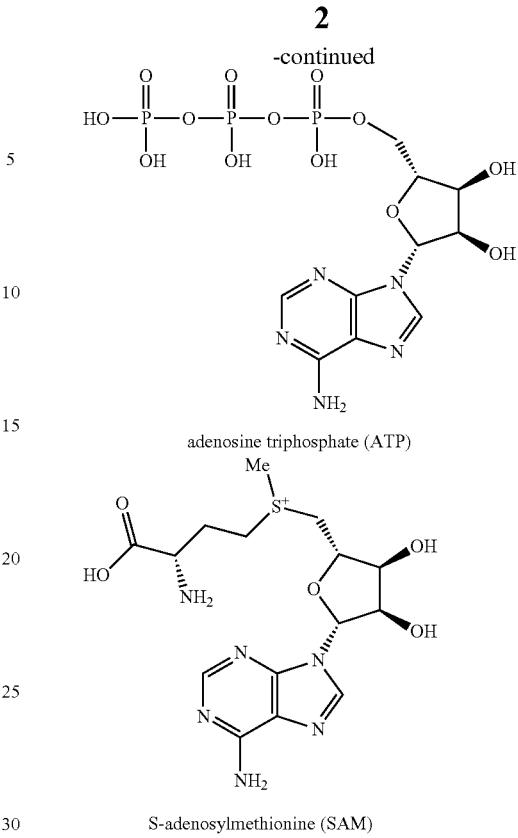

adenosine triphosphate (ATP)

S-adenosylmethionine (SAM)

One of the most understood processes involving SAM-utilizing proteins is biochemical transmethylation. The relatively unreactive thioether methyl group of methionine is made very reactive toward nitrogen, oxygen, sulfur, and carbon nucleophiles when coupled with the adenosyl group to provide the chemically destabilizing positively-charged sulfonium ion of SAM. SAM-utilizing methyltransferases are enzymes that catalyze transfer of the reactive methyl group from SAM to a substrate for covalent modification, leaving the stabilized S-adenosylhomocysteine (SAH or AdoHcy) by-product. Methyltransferases comprise a significant percentage of the proteome and are found in all organisms (Petrossian, T. C. and Clarke, S. G., *Molecular and Cellular Proteomics*, 2011, 10(1)). A large and diverse set of SAM-utilizing methyltransferase substrates is known. Broad substrate classes include histone and non-histone proteins, nucleic acids, polysaccharides, lipids, small organic molecules (e.g. catechol: Mannisto, P. T. and Kaakkola, S., *Pharmacological Reviews*, 1999, 51(4), 593-628), and inorganic substrates (e.g. arsenic: Thomas, D. J. et al., *Experimental Biology and Medicine*, 2007, 232(1), 3-13; Hayakawa, T. et al., *Archives of Toxicology*, 2004, 79(4), 183-191); and halides: (Ohsawa, N. et al., *Bioscience, Biotechnology and Biochemistry*, 2001, 65, 2397-2404; Attieh, J. M. et al., 1995, 270, 9250-9257). SAM-utilizing methyltransferases play a role in critical cellular processes including biosynthesis, signal transduction, chromatin regulation, and gene silencing.

While the SAM-utilizing methyltransferases share a common requirement for SAM, distinct differences exist in the SAM binding structural fold and also in the SAM binding mode. These different structural families can be grouped into at least seven classes, five classes that are typically designated I through V (Schubert, H. L. et al., *Trends in Biochemical Sciences*, 2003, 28(6), 329-335). Two other classes include the radical SAM enzymes (Frey, P. A. et al., *Critical Reviews* in *Biochemistry and Molecular Biology,* 2008, 43, 63-88), which catalyze diverse radical-based reactions that include methylation, and the isoprenylcysteine carboxy methyltransferases (ICMTs), which are integral membrane proteins (Yang, J. et al., *Molecular Cell,* 2011, 44(6), 997-1004). Amino-acid sequence homology within each class can be as low as 10%, showing that wide variations in molecular environment mediating catalysis of methyl transfer from SAM to substrate are allowed, which at least in part may be due to the favorable energetics involved in the conversion of SAM to SAH. Methyltransferases that bind and methylate protein substrates are generally found in Class I (classical fold) or Class V (SET fold), and methyltransferases that act on DNA substrates have been found in Classes I or IV (Schubert, H. L. et al., *Trends in Biochemical Sciences,* 2003, 28(6), 329-335). Non-catalytic domains outside the core structure determine substrate recognition. SAM-utilizing methyltransferases recruit SAM and a substrate to the SAM-dependent methyltransferase fold, where methyl transfer occurs and modified substrate and SAH are produced and released.

The involvement of methyltransferases in epigenetics is currently an intense area of research (Copeland, R. A. et al., *Nature Reviews Drug Discovery,* 2009, 8, 724-732). The field of epigenetics studies molecular changes such as DNA methylation and post-translational histone modifications that influence phenotype without alterations in the DNA sequence of the genome. Methyltransferases play a major role in epigenetic regulation of gene expression by catalyzing the modification of chromatin by specific methylations of DNA, histones, or biomolecules associated with chromatin (Kouzarides, T., *Cell,* 2007, 128, 693-705). Chromatin remodeling methyltransferases can generally be divided into two categories according to their substrates. DNA methyltransferases (DNMTs) methylate the 5-position carbon atom of cytosine in the CpG dinucleotide sites of the mammalian genome (Cheng, X. and Blumenthal, R. M., *Structure,* 2008, 16, 341-350). Protein methyltransferases (PMTs), which can generally be subdivided into protein lysine methyltransferases (PKMTs) and protein arginine methyltransferases (PRMTs), methylate protein lysine or arginine residues, respectively. The histone targets of PMTs are largely characterized while non-histone protein targets such as the FOXO transcription factors continue to be discovered (Yamagata, K. et al., *Molecular Cell,* 2008, 32, 221-231; Greer, E. L. and Brunet, A., *Oncogene,* 2005, 24, 7410-7425).

Aberrant DNA and histone methylation due to abnormal methyltransferase expression levels or mutations is associated with the onset and progression of a variety of cancers and other diseases and conditions (Egger, G., *Nature,* 2004, 429, 457-463; Esteller, M., *New England Journal of Medicine,* 2008, 358, 1148-1159).

Selective, small-molecule inhibitors of epigenetic targets, such as histone deacetylases (HDACs) and DNMTs, have been successfully designed and deployed as therapeutic agents for the treatment of myelomas, lymphomas, and other cancers and have been further investigated for use against inflammatory and autoimmune disorders (Copeland, R. A. et al., *Nature Reviews Drug Discovery,* 2009, 8, 724-732; Szyf, M., *Clinical Reviews in Allergy and Immunology,* 2010, 39(1), 62-77; Kaiser, J., *Science,* 2010, 330(6004), 576-578). PKMTs and PRMTs are favorable drug targets amenable to small-molecule inhibition (Copeland, R. A. et al., *Current Opinion in Chemical Biology,* 2010, 4, 505-510). Each methyltransferase is structurally unique and has a distinct functional profile (Dillon, S. C. et al., *Genome Biology,* 2005, 6, 227; Cheng, X. et al., *Annual Reviews in Biophysical and Biomolecular Structure,* 2005, 34, 267-294). Small molecule inhibitors are currently sought after for a variety of methyltransferases in the search for new drug therapies (Shaaban, S. A. and Bedford, M. A., *Chemistry and Biology,* 2007, 14(3), 242-244), and the potential pharmaceutical utility in areas such as antibiotics and treatment of Parkinson's Disease (e.g. catechol-O-methyltransferase inhibitors) and beyond is vast; thus, an efficient means for rapidly screening large compound collections against an ever-growing number of known SAM-utilizing methyltransferases is needed.

Various SAM-utilizing methyltransferase screening assays have been developed and used for identifying compound inhibitors. One such assay reported is a universal competitive fluorescence polarization (FP) methyltransferase activity immunoassay that measures formation of SAH (Graves, T. L. et al., *Analytical Biochemistry,* 2008, 373, 296-306). The assay employs an anti-AdoHcy antibody and fluorescence-labeled AdoHcy conjugate tracer to measure AdoHcy generated from the methyltransferase activity. Another SAM-utilizing methyltransferase assay reported is an enzyme-coupled continuous spectrophotometric screen (Dorgan, K. M. et al., *Analytical Biochemistry,* 2006, 350, 249-255). In this assay SAH generated from demethylation of SAM is hydrolyzed to S-ribosylhomocysteine and adenine by recombinant S-adenosylhomocysteine/5'-methylthioadenosine nucleosidase. Adenine is subsequently hydrolyzed to hypoxanthine and ammonia by recombinant adenine deaminase, a process which is monitored continuously by measuring absorbance at a wavelength of 256 nm. Another enzyme coupled assay used for measuring SAM-utilizing methyltransferase activity involves the conjugation of homocysteine (Hcy), which is generated from cleavage of SAH by SAH hydrolase (SAHH), to a thiol-reactive fluorophore (Collazo, E. et al., *Analytical Biochemistry,* 2005, 342, 86-92). A commercial radiometric histone methyltransferase assay is also known and has been adapted for high throughput screening (Horiuchi, K. Y. et al., *FASEB J,* 2010, 24, lb61). All of these assays gauge SAM-utilizing methyltransferase activity by measuring the generation of products formed as a consequence of the signature methyl-transfer reaction from SAM to the substrate but do not directly provide information as to the specific binding interactions of the test compound without subsequent enzymological study. In addition, target screening using a coupled enzyme assay method suffers from the potential generation of false positive leads due to inhibition of the coupling enzymes. The radiometric assay is a robust binding assay but possesses the inherent liability of generating radioactive waste. The assays developed here overcome these shortfalls and will also provide specific binding information by directly measuring binding affinities and dissociation constants of the test compounds.

A fluorescence polarization or TR-FRET assay could measure test compound binding to a SAM-utilizing protein by measuring displacement of a fluorescence-labeled ligand ("detection analyte" or "probe") from the protein. The universal cofactor SAM provides a structural template with which to design a versatile detection analyte. SAM itself is a chemically reactive methyl donor and thus is not a suitable compound for incorporation into a stable detection analyte. A robust, chemically stable SAM mimic possessing steric and electronic characteristics similar to those of SAM is therefore desirable. Such an analyte design would provide a SAM-utilizing protein ligand moiety seeking to take advantage of inherent pan-methyltransferase recruitment of SAM and could thus allow the analyte to be utilized across the SAM-dependent methyltransferase enzyme family. Herein are disclosed fluorescent detection analytes, assays that employ them, and their uses for assessing binding of test compounds.

Sinefungin, a SAM- and SAH-analog nucleoside isolated from *Streptomyces griseolus* and *Streptomyces incarnatus*, exhibits an array of antimicrobial effects due primarily to its inhibition of SAM-utilizing methyltransferases (Malina, H. et al., *Journal of Antibiotics*, 1985, 38(9), 1204-1210; Berry, D. R. and Abbott, B. J., *Journal of Antibiotics*, 1978, 31(3), 185-191; Vedel M. et al., *Biochemical and Biophysical Research Communications*, 1978, 85(1), 371-376). The sinefungin molecular structure may be divided into three subunits: a central ribose ring, an adenine ring connected by its 9-nitrogen position to the 1'-ribose ring carbon atom, and an ornithine side chain connected by its amino acid δ-carbon to the 5'-carbon atom of the ribose ring. Recent reports disclose structures of sinefungin bound in the SET domain of histone PKMTs SET7/9, LSMT, SmyD1 and SmyD3 (Subramanian, K. et al., *Molecular Cell*, 2008, 30(3), 336-47; Couture et al., *The Journal of Biological Chemistry*, 2006, 281(28), 19280-19287; Sirinupong, N. et al., *The Journal of Biological Chemistry*, 2010, 285(52), 40635-40644; Sirinupong, N. et al., *Journal of Molecular Biology*, 2010). Earlier published sinefungin-nucleic acid methyltransferase complex structures wherein sinefungin is shown to bind in the SAM binding site show only minor structural changes in the complex versus the cases in which SAM or SAH are shown bound (Zheng, S. et al., *The Journal of Biological Chemistry*, 2006, 281(47), 35904-35913; Thomas, C. B. et al., *The Journal of Biological Chemistry*, 2003, 278(28), 26094-26101).

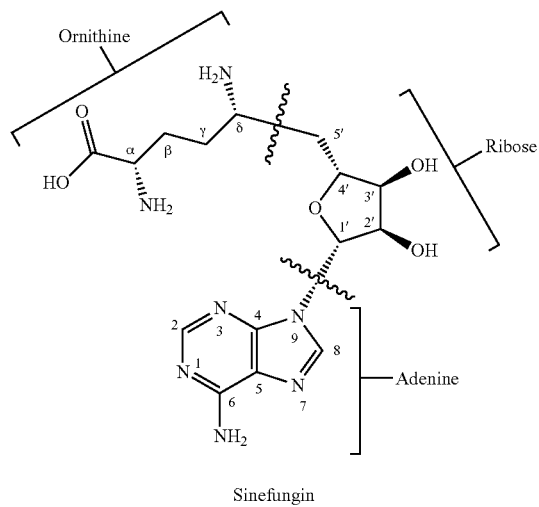

Sinefungin

SAM-like affinity for a wide range of methyltransferases and relative chemical stability make sinefungin a reasonable detection analyte SAM-utilizing protein methyltransferase ligand moiety. For example, sinefungin binds to human SET7/9 with only a six-fold lower affinity than SAM, and sinefungin binds to Arabidopsis LSMT with only a fourteen-fold lower affinity than SAM (Couture et al., *The Journal of Biological Chemistry*, 2006, 281(28), 19280-19287; Horowitz et al., *The Journal of Biological Chemistry*, 2011, Epub jbc.M111.232876). Variations in spatial requirements among different methyltransferase catalytic domains may require that an assortment of sinefungin-based detection analytes be utilized to screen test compounds against a broad panel of these enzymes. Sinefungin-based detection analyte alternatives may vary based on different linker-fluorophore attachment positions on sinefungin. The linker moiety, for example, may be covalently bound to sinefungin at a nitrogen or carboxy oxygen position on the ornithine residue, one of the two ribose hydroxyl oxygen atoms, or to an open carbon or the free amino position on the C-6 carbon atom of the adenine base ring. Sinefungin-based probes may be designed that are selective to SET domain-containing lysine methyltransferases or other classes of methyltransferases, which can use different binding modes to recognize SAM. These differences may necessitate that the linker moieties tethering sinefungin or sinefungin analogs to the fluorophore be attached to sinefungin at different positions to accommodate the varying binding modes.

Fluorescence polarization and TR-FRET assays generally provide advantages in the study of protein-ligand binding over other conventional assay types. These assay formats allow rapid real-time measurements, avoid the use of radioactive materials, are homogeneous requiring minimal additions and no washing steps, and may possess sub-nanomolar detection limits. FP and TR-FRET assays are currently used in drug discovery and are routinely converted to high-throughput screening (HTS) formats (Burke, T. J. et al., *Combinatorial Chemistry and High Throughput Screening*, 2003, 6(3), 183-194). The uses, advantages, and photophysical principles associated with FP and TR-FRET assays have been described and are well known to those ordinarily skilled in the art (Lakowicz, J. R., *Principles of Fluorescence Spectroscopy*, Springer, N.Y., USA, 1999; Owicki, J. C., *Journal of Biomolecular Screening*, 2000, 5(5), 297-306; Nasir, M. S., Jolley, M. E., *Combinatorial Chemistry & High Throughput Screening*, 1999, 2, 177-190; Klostermeier, D. and Millar, D. P., *Biopolymers (Nucleic Acid Sciences)*, 2002, 61, 159-179).

SUMMARY OF THE INVENTION

Assay methods of the exemplary embodiments may generally comprise forming homogeneous assay mixtures comprising target SAM-utilizing protein, fluorescent detection analyte, and test compound, incubating, and measuring FP or TR-FRET signal emitted in order to determine a measure of test compound-SAM-utilizing protein binding.

Assay mixtures of the exemplary embodiments comprise a SAM-utilizing protein, and a fluorescent detection analyte that binds with the SAM-utilizing protein in the absence of test compound. Assay mixtures of the exemplary embodiments may further comprise a test compound. Exemplary assay mixture embodiments may generate FP or TR-FRET fluorescence emissions, such as but not limited to signal intensity, polarization (for FP), or ratio of donor/acceptor emissions (for TR-FRET), that gauge test compound and detection analyte binding with the SAM-utilizing protein.

Fluorescent detection analytes of the exemplary embodiments comprise a fluorophore moiety, a SAM-utilizing protein ligand moiety, and a linker moiety that covalently links the fluorophore moiety with the SAM-utilizing protein ligand moiety, and could be utilized in FP or TR-FRET assays to measure test compound binding.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

BRIEF DESCRIPTION OF THE DRAWINGS

FIG. 4 shows the Z'-factor analysis of the SET7/9 FP assay utilizing Sinefungin Probe 1A.

FIG. 7 illustrates a general synthetic pathway for preparing aza-adenosine fluorescent detection analytes.

DETAILED DESCRIPTION OF THE INVENTION

Figure 1:
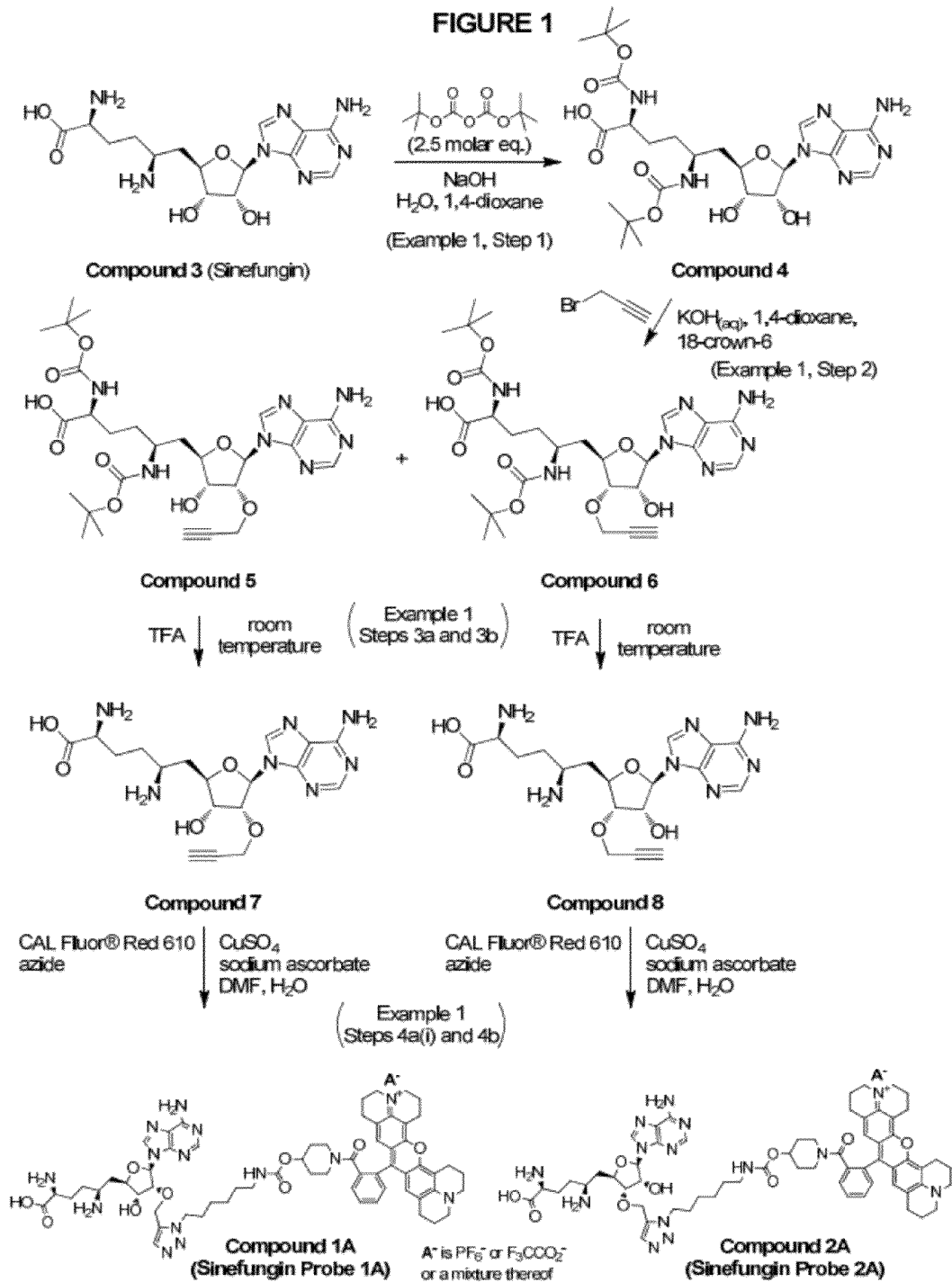
FIG. 1 illustrates a synthetic pathway for preparing the fluorescent detection analytes Compound 1A (Sinefungin Probe 1A) and Compound 2A (Sinefungin Probe 2A).

The exemplary embodiments may be directed to FP or TR-FRET assays, assay mixtures, and fluorescent detection analytes for identifying compounds that bind to SAM-utilizing proteins. Certain embodiments may be directed to FP or TR-FRET assays and assay mixtures wherein the SAM-utilizing proteins are methyltransferases. Certain other embodiments may be directed to FP or TR-FRET assays and assay mixtures wherein the methyltransferases are DNA methyltransferases, histone methyltransferases, methyltransferases for transcription factors and chromatin-associated proteins, or methyltransferases for cellular molecules.

FP signal is typically generated by measuring the polarization of the fluorescence emitted from a detection analyte. As the detection analyte freely tumbles in solution, the polarization signal is low. This signal increases when the analyte is bound by a molecule (e.g. a methyltransferase) that is relatively large as compared to the analyte. Thus, any test compound that displaces the analyte from the methyltransferase will induce a measurable decrease in the FP signal.

TR-FRET signal is typically a function of measured emission of an acceptor fluorophore following excitation of the donor fluorophore. The acceptor fluorophore emission is only generated if the donor fluorophore is in close proximity (generally less than 100 angstroms) to the acceptor fluorophore and energy transfer from donor to acceptor fluorophore occurs. Thus, any test compound that dissociates the acceptor fluorophore from the close proximity of the donor fluorophore-bearing SAM-utilizing protein will induce a measurable decrease in the TR-FRET signal.

Exemplary methods employed for measuring FP and TR-FRET signals are described herein, and are generally known to those skilled in the art. The compounds identified as binding ligands may provide novel therapies for the treatment of diseases or conditions mediated by the SAM-utilizing protein employed in the assay.

As used herein below with respect to the exemplary embodiments and claims, the term "fluorescence signal or property" is meant to describe a property or properties associated with fluorescence emitted by the assay mixture. Such properties comprise those typically found in the art, including but not limited to polarization signal, intensity, or signal decay. Such property or properties can be used to measure and quantify test compound binding to SAM-utilizing proteins as described previously or in the exemplary embodiments or claims.

As used herein, the properties of the FP signal may be described in terms of the measured polarization signal.

As used herein, the properties of the TR-FRET signal may be described in terms of the intensity of the measured fluorescence emission spectrum.

The exemplary embodiments herein may provide a homogeneous, rapid, and consistent assay for high-throughput screening of compounds or agents for binding to a SAM-utilizing protein.

A moiety, as defined herein with respect to the exemplary embodiments and claims, generally refers to a functional group or a particular portion of a molecule. A moiety may be bound to other portions of the molecule, or moieties, by a covalent chemical bond or bonds.

A nucleoside moiety is a portion of a molecule comprising a nucleoside. A nucleoside, as defined herein with respect to the exemplary embodiments and claims, generally refers to a glycosylamine comprising a nucleobase (base) bound to a ribose or deoxyribose (sugar) by way of a β-glycosidic linkage. One nucleoside known to those ordinarily skilled in the art is adenosine, which consists of the base, adenine, bound by a β-glycosidic linkage to the sugar, ribose. Other nucleosides known to those ordinarily skilled in the art include cytidine, guanosine, inosine, thymidine, and uridine.

A nucleoside-type moiety, as defined herein with respect to the exemplary embodiments and claims, is a portion of a molecule comprising a nucleoside or a nucleoside having at least one structural modification. An exemplary structural modification may include, but is not limited to, a stereochemical variation from a naturally-derived molecule or moiety. Another exemplary structural modification may include, but is not limited to, a variation in the position of an atom or functional group, such as is the case for a structural isomer or regioisomer of a naturally-derived molecule or moiety. Another exemplary structural modification may include, but is not limited to, the substitution of an atom or functional group of a naturally-derived molecule or moiety with an alternative atom or functional group. An exemplary nucleoside-type moiety may possess one or more of the same type of exemplary structural modifications described above, or a combination of more than one variety of exemplary structural modifications described above.

An exemplary nucleoside-type moiety that may be utilized is an adenosine moiety. Another exemplary nucleoside-type moiety that may be utilized is a deaza-adenosine moiety, such as a 3-deaza-adenosine moiety, having one adenine-ring nitrogen atom replaced with a carbon atom bearing a hydrogen atom, as illustrated below:

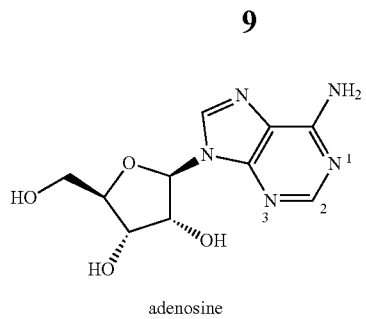
adenosine

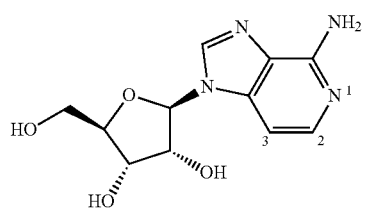
3-deaza-adenosine

Other exemplary nucleoside-type moieties that may be utilized may include, but are not limited to, an adenosine moiety or deaza-adenosine moiety substituted with a functional group (FG) at one of the base ring positions, as illustrated below:

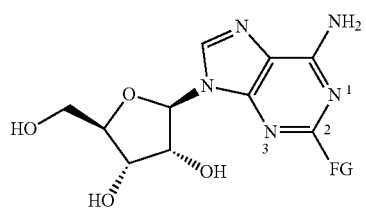
2-functionalized adenosine

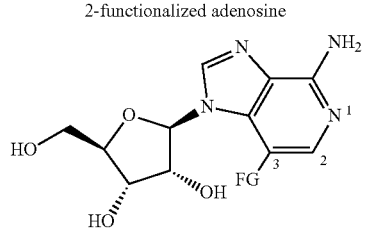
3-functionalized 3-deaza-adenosine

FG = functional group

Further exemplary nucleoside-type moieties that may be utilized include, but are not limited to, a sinefungin moiety, an S-substituted-5'-thioadenosine (also referred to herein as a "sulfur-based," a "thioadenosine," or a "SAM-like") moiety, and a 5'-aza-adenosine (also referred to herein as a "nitrogen-based," an "aza-adenosine," or an "aza-SAM-like") moiety, as illustrated below:

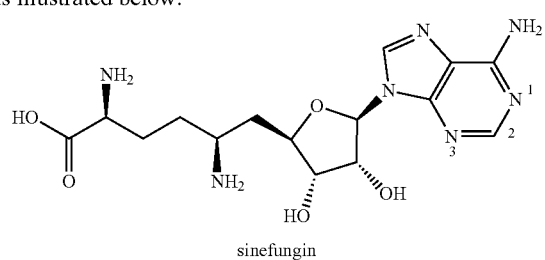
sinefungin

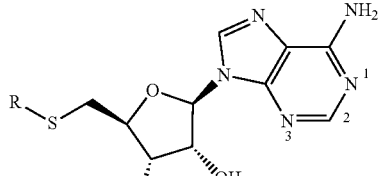
S-substituted-5'-thioadenosine

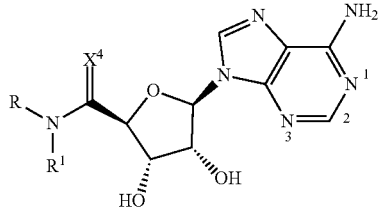
5'-aza-adenosine
$X^4$ is $H_2$ or O

R and $R^1$ are further described in various embodiments below.

A sinefungin moiety, as defined herein, refers to a moiety wherein the molecular structure of that moiety is that of sinefungin, a stereoisomer of sinefungin, or a related analog to sinefungin as described herein. Exemplary sinefungin moieties that may be utilized include, but are not limited to, sinefungin, an N- or O-protected or an N- or O-$C_{1-4}$ alkylated derivative (including alkyl esters of the sinefungin carboxylic acid) of sinefungin, a carboxamide analog (wherein the sinefungin carboxylic acid is instead a carboxamide or N-alkyl-carboxamide or N,N-dialkylcarboxamide) of sinefungin, a deaza-adenine analog of sinefungin, a deoxyribose analog of sinefungin, a sinefungin analog wherein one of the sinefungin-unsubstituted adenine carbon atoms is substituted with a halogen, amino, alkylamino, trifluoromethyl, methoxy, ethoxy, trifluoromethoxy, thiomethyl, cyano, $C_{1-4}$ alkyl, $C_{2-4}$ alkenyl, or $C_{2-4}$ alkynyl, a sinefungin analog wherein the adenine ring is replaced with another heterocyclic ring, or any sinefungin stereoisomer, sinefungin regioisomer, sinefungin analog stereoisomer, or sinefungin analog regioisomer thereof.

Exemplary nucleoside-type moieties may be covalently bonded to linker moieties as described elsewhere herein. Exemplary structural positions at which a nucleoside-type moiety may be covalently bonded to a linker moiety may include, but are not limited to, a base-ring carbon atom position, a base ring functional group that possesses a suitable site for covalent linkage to a linker moiety, a ribose-2'-hydroxyl oxygen atom, or a ribose-3'-hydroxyl oxygen atom.

Exemplary detection analytes may be prepared by methods generally and specifically described herein.

One exemplary embodiment may be directed to a method for identifying compounds that bind to SAM-utilizing proteins comprising:
  (a) forming an assay mixture comprising:
    (1) a fluorescent detection analyte comprising:
      (i) a fluorophore moiety;
      (ii) a SAM-utilizing protein ligand moiety; and
      (iii) a linker moiety that covalently links the fluorophore moiety with the SAM-utilizing protein ligand moiety;
    (2) a SAM-utilizing protein or a SAM-utilizing protein labeled with a donor fluorophore or an acceptor fluorophore; and
    (3) a test compound;

(b) irradiating the assay mixture at a particular excitation wavelength to generate a fluorescence signal or property;

(c) measuring the fluorescence signal or property generated by the assay mixture; and (d) determining the level of binding of the test compound to the SAM-utilizing protein or to the SAM-utilizing protein labeled with the donor fluorophore or the acceptor fluorophore from the measured fluorescence signal or property.

In certain of these embodiments, the SAM-utilizing protein ligand moiety (ii) comprises a nucleoside-type moiety. Exemplary nucleoside-type moieties that may be utilized include those described above, such as, for example, a sinefungin moiety, a sulfur-based moiety, or a nitrogen-based moiety.

In certain other of these embodiments, wherein the SAM-utilizing protein ligand moiety (ii) comprises a sinefungin moiety, the linker moiety that covalently links the fluorophore moiety with the sinefungin moiety (iii) comprises a linker moiety that covalently links the fluorophore moiety with the sinefungin moiety through an atom on the sinefungin moiety selected from the group consisting of a ribose 2'-hydroxy oxygen atom and a ribose 3'-hydroxy oxygen atom.

In certain other of these embodiments, wherein the SAM-utilizing protein ligand moiety (ii) comprises a sinefungin moiety, the linker moiety that covalently links the fluorophore moiety with the sinefungin or sinefungin analog moiety (iii) comprises a linker moiety that covalently links the fluorophore moiety with the sinefungin moiety through an atom on the base ring or base ring replacement portion of the sinefungin moiety.

Another exemplary embodiment may be directed to a method for identifying compounds that bind to SET domain-containing lysine methyltransferase enzymes comprising:

(a) forming an assay mixture comprising:
  (1) a fluorescent detection analyte comprising:
    (i) a fluorophore moiety;
    (ii) a sinefungin moiety; and
    (iii) a linker moiety that covalently links the fluorophore moiety with the sinefungin moiety through an atom on the sinefungin moiety selected from the group consisting of the ribose 2'-hydroxy oxygen atom, the ribose 3'-hydroxy oxygen atom, and the adenine 2-carbon atom;
  (2) a SET domain-containing lysine methyltransferase enzyme or a SET domain-containing lysine methyltransferase enzyme labeled with a donor fluorophore; and
  (3) a test compound;

(b) irradiating the assay mixture at a particular excitation wavelength to generate a fluorescence signal or property;

(c) measuring the fluorescence signal or property emitted by the assay mixture; and (d) determining the level of binding of the test compound to the SET domain-containing lysine methyltransferase enzyme or to the SET domain-containing lysine methyltransferase enzyme labeled with the donor fluorophore or the acceptor fluorophore from the measured fluorescence signal or property.

In certain of these embodiments, the SET domain-containing lysine methyltransferase enzyme (2) is selected from the group consisting of SET7/9, GLP, MLL, and G9a.

In certain of these embodiments, wherein the SET domain-containing lysine methyltransferase enzyme (2) is selected from the group consisting of SET7/9, GLP, MLL, and G9a, the detection analyte (1) is selected from the group consisting of Sinefungin Probe 1A, Sinefungin Probe 1B, Sinefungin Probe 2A, Sinefungin Probe 3 and Sinefungin Probe 4. Sinefungin Probe 1A, Sinefungin Probe 1B, Sinefungin Probe 2A, Sinefungin Probe 3 and Sinefungin Probe 4 are each illustrated and described in the Examples below.

Another exemplary embodiment may be directed to a method for identifying compounds that bind to lysine methyltransferase enzyme SET7/9 comprising:

(a) measuring a fluorescence signal or property of an irradiated assay mixture, wherein the assay mixture comprises:
  (1) a fluorescent detection analyte comprising:
    (i) a fluorophore moiety;
    (ii) a sinefungin moiety; and
    (iii) a linker moiety that covalently links the fluorophore moiety with the sinefungin moiety through an atom on the sinefungin moiety selected from the group consisting of a ribose 2'-hydroxy oxygen atom and a ribose 3'-hydroxy oxygen atom;
  (2) a lysine methyltransferase enzyme SET7/9 or a lysine methyltransferase enzyme SET7/9 labeled with a donor fluorophore or an acceptor fluorophore; and
  (3) a test compound;

(b) irradiating the assay mixture at a particular excitation wavelength to generate a fluorescence signal or property;

(c) measuring the fluorescence signal or property generated by the assay mixture; and (d) determining the level of binding of the test compound to the lysine methyltransferase enzyme SET7/9 or to the lysine methyltransferase enzyme SET7/9 labeled with the donor fluorophore or the acceptor fluorophore from the measured fluorescence signal or property.

In certain of these embodiments, the fluorescent detection analyte (1) is selected from the group consisting of Sinefungin Probe 1A, Sinefungin Probe 1B, Sinefungin Probe 2A, Sinefungin Probe 3 and Sinefungin Probe 4.

Another exemplary embodiment may be directed to a method for identifying compounds that bind to lysine methyltransferase enzyme G9a comprising:

(a) measuring a fluorescence signal or property of an irradiated assay mixture, wherein the assay mixture comprises:
  (1) a fluorescent detection analyte comprising:
    (i) a fluorophore moiety;
    (ii) a sinefungin moiety; and
    (iii) a linker moiety that covalently links the fluorophore moiety with the sinefungin moiety through an atom on the sinefungin moiety selected from the group consisting of a ribose 2'-hydroxy oxygen atom and a ribose 3'-hydroxy oxygen atom;
  (2) a lysine methyltransferase enzyme G9a or a lysine methyltransferase enzyme G9a labeled with a donor fluorophore or an acceptor fluorophore; and
  (3) a test compound;

(b) irradiating the assay mixture at a particular excitation wavelength to generate a fluorescence signal or property;

(c) measuring the fluorescence signal or property generated by the assay mixture; and (d) determining the level of binding of the test compound to the lysine methyltransferase enzyme G9a or to the lysine methyltransferase enzyme G9a labeled with the donor fluorophore or the acceptor fluorophore from the measured fluorescence signal or property.

In certain exemplary embodiments, the fluorescent detection analyte (1) is selected from the group consisting of Sinefungin Probe 1A, Sinefungin Probe 1B, Sinefungin Probe 2A, Sinefungin Probe 3 and Sinefungin Probe 4.

Another exemplary embodiment may be directed to a method for identifying compounds that bind to lysine methyltransferase enzyme GLP comprising:
- (a) measuring a fluorescence signal or property of an irradiated assay mixture, wherein the assay mixture comprises:
  - (1) a fluorescent detection analyte comprising:
    - (i) a fluorophore moiety;
    - (ii) a sinefungin moiety; and
    - (iii) a linker moiety that covalently links the fluorophore moiety with the sinefungin moiety through an atom on the sinefungin moiety selected from the group consisting of a ribose 2'-hydroxy oxygen atom and a ribose 3'-hydroxy oxygen atom;
  - (2) a lysine methyltransferase enzyme GLP or a lysine methyltransferase enzyme GLP labeled with a donor fluorophore or an acceptor fluorophore; and
  - (3) a test compound;
- (b) irradiating the assay mixture at a particular excitation wavelength to generate a fluorescence signal or property;
- (c) measuring the fluorescence signal or property generated by the assay mixture; and
- (d) determining the level of binding of the test compound to the lysine methyltransferase enzyme GLP or to the lysine methyltransferase enzyme GLP labeled with the donor fluorophore or the acceptor fluorophore from the measured fluorescence signal or property.

In certain exemplary embodiments, the fluorescent detection analyte (1) is selected from the group consisting of Sinefungin Probe 1A, Sinefungin Probe 1B, Sinefungin Probe 2A, Sinefungin Probe 3 and Sinefungin Probe 4.

Another exemplary embodiment may be directed to a method for identifying compounds that bind to lysine methyltransferase enzyme MLL comprising:
- (a) measuring a fluorescence signal or property of an irradiated assay mixture, wherein the assay mixture comprises:
  - (1) a fluorescent detection analyte comprising:
    - (i) a fluorophore moiety;
    - (ii) a sinefungin moiety; and
    - (iii) a linker moiety that covalently links the fluorophore moiety with the sinefungin moiety through an atom on the sinefungin moiety selected from the group consisting of a ribose 2'-hydroxy oxygen atom and a ribose 3'-hydroxy oxygen atom;
  - (2) a lysine methyltransferase enzyme MLL or a lysine methyltransferase enzyme MLL labeled with a donor fluorophore or an acceptor fluorophore; and
  - (3) a test compound;
- (b) irradiating the assay mixture at a particular excitation wavelength to generate a fluorescence signal or property;
- (c) measuring the fluorescence signal or property generated by the assay mixture; and
- (d) determining the level of binding of the test compound to the lysine methyltransferase enzyme MLL or to the lysine methyltransferase enzyme MLL labeled with the donor fluorophore or the acceptor fluorophore from the measured fluorescence signal or property.

In certain exemplary embodiments, the fluorescent detection analyte (1) is selected from the group consisting of Sinefungin Probe 1A, Sinefungin Probe 1B, Sinefungin Probe 2A, Sinefungin Probe 3 and Sinefungin Probe 4.

Another exemplary embodiment may be directed to a method for identifying compounds that bind to SET domain-containing lysine methyltransferase enzymes comprising:
- (a) forming an assay mixture comprising:
  - (1) a fluorescent detection analyte comprising
    - (i) a fluorophore moiety;
    - (ii) an S-substituted-5'-thioadenosine moiety; and
    - (iii) a linker moiety that covalently links the fluorophore moiety with the S-substituted-5'-thioadenosine moiety;
  - (2) a SET domain-containing lysine methyltransferase enzyme or a SET domain-containing lysine methyltransferase enzyme labeled with a donor fluorophore; and
  - (3) a test compound;
- (b) irradiating the assay mixture at a particular excitation wavelength to generate a fluorescence signal or property;
- (c) measuring the fluorescence signal or property generated by the assay mixture; and
- (d) determining the level of binding of the test compound to the SET domain-containing lysine methyltransferase enzyme or to the SET domain-containing lysine methyltransferase enzyme labeled with the donor fluorophore or the acceptor fluorophore from the measured fluorescence signal or property.

Another exemplary embodiment may be directed to a method for identifying compounds that bind to the SET domain-containing lysine methyltransferase enzyme PRDM9 comprising:
- (a) forming an assay mixture comprising:
  - (1) a fluorescent detection analyte comprising
    - (i) a fluorophore moiety;
    - (ii) an S-substituted-5'-thioadenosine moiety; and
    - (iii) a linker moiety that covalently links the fluorophore moiety with the S-substituted-5'-thioadenosine moiety;
  - (2) the SET domain-containing lysine methyltransferase enzyme PRDM9 or PRDM9 labeled with a donor fluorophore; and
  - (3) a test compound;
- (b) irradiating the assay mixture at a particular excitation wavelength to generate a fluorescence signal or property;
- (c) measuring the fluorescence signal or property generated by the assay mixture; and
- (d) determining the level of binding of the test compound to PRDM9 or to the PRDM9 labeled with the donor fluorophore or the acceptor fluorophore from the measured fluorescence signal or property.

In certain of these embodiments, the fluorescent detection analyte (1) comprises Thioadenosine Probe 1, which is described and illustrated below in the Examples.

Another exemplary embodiment may be directed to a method for identifying compounds that bind to arginine methyltransferase enzymes comprising:
- (a) forming an assay mixture comprising:
  - (1) a fluorescent detection analyte comprising
    - (i) a fluorophore moiety;
    - (ii) an S-substituted-5'-thioadenosine moiety; and
    - (iii) a linker moiety that covalently links the fluorophore moiety with the S-substituted-5'-thioadenosine moiety;

(2) a protein arginine methyltransferase (PRMT) enzyme or PRMT enzyme labeled with a donor fluorophore; and (3) a test compound;

(b) irradiating the assay mixture at a particular excitation wavelength to generate a fluorescence signal or property;

(c) measuring the fluorescence signal or property generated by the assay mixture; and (d) determining the level of binding of the test compound to the PRMT enzyme or to the PRMT enzyme labeled with the donor fluorophore or the acceptor fluorophore from the measured fluorescence signal or property.

In certain of these embodiments, the PRMT enzyme (2) is selected from the group consisting of PRMT1 and PRMT4 (CARM1).

In certain of these embodiments, the fluorescent detection analyte (1) comprises Thioadenosine Probe 1.

Another exemplary embodiment may be directed to an assay mixture for identifying compounds that bind to a SAM-utilizing protein comprising:

(a) a detection analyte comprising:
(1) a fluorophore moiety;
(2) a SAM-utilizing protein ligand moiety; and
(3) a linker moiety that covalently links the fluorophore moiety with the SAM-utilizing protein ligand moiety;

(b) a SAM-utilizing protein or a SAM-utilizing protein labeled with a donor fluorophore or an acceptor fluorophore; and (c) a test compound.

In certain of these embodiments, the SAM-utilizing protein ligand moiety used in the assay mixture comprises a nucleoside-type moiety. Exemplary nucleoside-type moieties that may be utilized include those described above, such as, for example, a sinefungin moiety, a sulfur-based moiety, or a nitrogen-based moiety.

In certain other of these embodiments, wherein the SAM-utilizing protein ligand moiety (ii) used in the assay mixture comprises a sinefungin moiety, the linker moiety that covalently links the fluorophore moiety with the sinefungin moiety (iii) comprises a linker moiety that covalently links the fluorophore moiety with the sinefungin moiety through an atom on the sinefungin moiety selected from the group consisting of a ribose 2'-hydroxy oxygen atom and a ribose 3'-hydroxy oxygen atom.

In certain other of these embodiments, wherein the SAM-utilizing protein ligand moiety (ii) used in the assay mixture comprises a sinefungin moiety, the linker moiety that covalently links the fluorophore moiety with the sinefungin or sinefungin analog moiety (iii) comprises a linker moiety that covalently links the fluorophore moiety with the sinefungin moiety through an atom on the base ring or base ring replacement portion of the sinefungin moiety.

Another exemplary embodiment may be directed to an assay mixture for identifying compounds that bind to a SAM-utilizing methyltransferase enzyme comprising:

(a) a detection analyte comprising:
(1) a fluorophore moiety;
(2) a sinefungin moiety; and
(3) a linker moiety that covalently links the fluorophore moiety with the sinefungin moiety;

(b) a SAM-utilizing methyltransferase enzyme or a SAM-utilizing methyltransferase enzyme labeled with a donor fluorophore or an acceptor fluorophore; and (c) a test compound.

Another exemplary embodiment may be directed to an assay mixture for identifying compounds that bind to a SAM-utilizing methyltransferase enzyme comprising:

(a) a detection analyte comprising:
(1) a fluorophore moiety;
(2) a sinefungin moiety; and
(3) a linker moiety that covalently links the fluorophore moiety with the sinefungin moiety through an atom on the sinefungin moiety selected from the group consisting of the ribose 2'-hydroxy oxygen atom, the ribose 3'-hydroxy oxygen atom, and the adenine 2-carbon atom;

(b) a SAM-utilizing methyltransferase enzyme or a SAM-utilizing methyltransferase enzyme labeled with a donor fluorophore or an acceptor fluorophore; and (c) a test compound.

Another exemplary embodiment may be directed to an assay mixture for identifying compounds that bind to a SET domain-containing methyltransferase enzyme comprising:

(a) a detection analyte comprising:
(1) a fluorophore moiety;
(2) a sinefungin moiety; and
(3) a linker moiety that covalently links the fluorophore moiety with the sinefungin moiety through an atom on the sinefungin moiety selected from the group consisting of the ribose 2'-hydroxy oxygen atom, the ribose 3'-hydroxy oxygen atom, and the adenine 2-carbon atom;

(b) a SET domain-containing lysine methyltransferase enzyme or a SET domain-containing lysine methyltransferase enzyme labeled with a donor fluorophore or an acceptor fluorophore; and (c) a test compound.

In certain of these embodiments, the SET domain-containing lysine methyltransferase enzyme (2) of the assay mixture is selected from the group consisting of SET7/9, GLP, MLL, and G9a.

In certain of these embodiments, wherein the SET domain-containing lysine methyltransferase enzyme (2) of the assay mixture is selected from the group consisting of SET7/9, GLP, MLL, and G9a, the detection analyte (1) is selected from the group consisting of Sinefungin Probe 1A, Sinefungin Probe 1B, Sinefungin Probe 2A, Sinefungin Probe 3 and Sinefungin Probe 4.

Another exemplary embodiment may be directed to an assay mixture for identifying compounds that bind to a SET domain-containing methyltransferase enzyme comprising:

(a) a detection analyte selected from the group consisting of Sinefungin Probe 1A, Sinefungin Probe 1B, Sinefungin Probe 2A, Sinefungin Probe 3, and Sinefungin Probe 4;

(b) a SET domain-containing lysine methyltransferase enzyme or a SET domain-containing lysine methyltransferase enzyme labeled with a donor fluorophore or an acceptor fluorophore, the SET domain-containing lysine methyltransferase enzyme selected from the group consisting of SET7/9, GLP, MLL, and G9a; and (c) a test compound.

Another exemplary embodiment may be directed to an assay mixture for identifying compounds that bind to lysine methyltransferase enzyme SET7/9 comprising:

(a) a detection analyte selected from the group consisting of Sinefungin Probe 1A, Sinefungin Probe 1B, Sinefungin Probe 2A, Sinefungin Probe 3, and Sinefungin Probe 4;

(b) SET7/9 or SET7/9 labeled with a donor fluorophore or an acceptor fluorophore; and (c) a test compound.

Another exemplary embodiment may be directed to an assay mixture for identifying compounds that bind to lysine methyltransferase enzyme G9a comprising:
(a) a detection analyte selected from the group consisting of Sinefungin Probe 1A, Sinefungin Probe 1B, Sinefungin Probe 2A, Sinefungin Probe 3, and Sinefungin Probe 4;
(b) G9a or G9a labeled with a donor fluorophore or an acceptor fluorophore; and
(c) a test compound.

Another exemplary embodiment may be directed to an assay mixture for identifying compounds that bind to lysine methyltransferase enzyme GLP comprising:
(a) a detection analyte selected from the group consisting of Sinefungin Probe 1A, Sinefungin Probe 1B, Sinefungin Probe 2A, Sinefungin Probe 3, and Sinefungin Probe 4;
(b) GLP or GLP labeled with a donor fluorophore or an acceptor fluorophore; and
(c) a test compound.

Another exemplary embodiment may be directed to an assay mixture for identifying compounds that bind to lysine methyltransferase enzyme MLL comprising:
(a) a detection analyte selected from the group consisting of Sinefungin Probe 1A, Sinefungin Probe 1B, Sinefungin Probe 2A, Sinefungin Probe 3, and Sinefungin Probe 4;
(b) MLL or MLL labeled with a donor fluorophore or an acceptor fluorophore; and
(c) a test compound.

Another exemplary embodiment may be directed to an assay mixture for identifying compounds that bind to SET domain-containing lysine methyltransferase enzymes comprising:
(a) a detection analyte comprising:
 (1) a fluorophore moiety;
 (2) an S-substituted-5'-thioadenosine moiety; and
 (3) a linker moiety that covalently links the fluorophore moiety with the S-substituted-5'-thioadenosine moiety;
(b) a SET domain-containing lysine methyltransferase enzyme or a SET domain-containing lysine methyltransferase enzyme labeled with a donor fluorophore; and
(c) a test compound.

Another exemplary embodiment may be directed to an assay mixture for identifying compounds that bind to SET domain-containing lysine methyltransferase enzyme PRDM9 comprising:
(a) a detection analyte comprising:
 (1) a fluorophore moiety;
 (2) an S-substituted-5'-thioadenosine moiety; and
 (3) a linker moiety that covalently links the fluorophore moiety with the S-substituted-5'-thioadenosine moiety;
(b) the SET domain-containing lysine methyltransferase enzyme PRDM9 or PRDM9 labeled with a donor fluorophore; and
(c) a test compound.

In certain of these embodiments, the detection analyte (a) of the assay mixture comprises the fluorescent detection analyte Thioadenosine Probe 1.

Another exemplary embodiment may be directed to an assay mixture for identifying compounds that bind to arginine methyltransferase enzymes comprising:
(a) a detection analyte comprising:
 (1) a fluorophore moiety;
 (2) an S-substituted-5'-thioadenosine moiety; and
 (3) a linker moiety that covalently links the fluorophore moiety with the S-substituted-5'-thioadenosine moiety;
(b) an arginine methyltransferase enzyme or an arginine methyltransferase enzyme labeled with a donor fluorophore; and
(c) a test compound.

In certain of these embodiments, the arginine methyltransferase enzyme of the assay mixture is selected from the group consisting of PRMT1 and PRMT4 (CARM1).

In certain of these embodiments, the detection analyte (a) of the assay mixture comprises the fluorescent detection analyte Thioadenosine Probe 1.

Another exemplary embodiment may be directed to a fluorescent detection analyte having the structure of Formula (I):

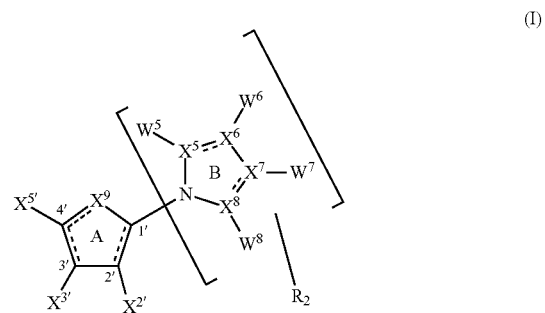

(I)

wherein the ----- between two atoms in either the A ring or the B ring represents the bond involving the two atoms is either a single or a double bond, and it may only represent a double bond between the 4'-carbon and $X^9$ when $X^9$ is CH;

wherein $X^9$ is O, $NR^7$, S, CH (allowed when its bond to the 4'-carbon is a carbon-carbon double bond), or $CH_2$ (allowed when its bond to the 4'-carbon is a carbon-carbon single bond);

wherein $R^7$ is hydrogen or methyl;

wherein each of $X^5$, $X^6$, $X^7$, and $X^8$ is independently a carbon or a nitrogen;

wherein no more than three of $X^5$, $X^6$, $X^7$, and $X^8$ is nitrogen;

wherein when any $X^5$, $X^6$, $X^7$, or $X^8$ is nitrogen, the associated $W^5$, $W^6$, $W^7$, and $W^8$, respectively, is not present;

wherein when $X^5$ is carbon, $W^5$ may be hydrogen, methyl, amino, or chloro;

wherein when $X^6$ is carbon, $W^6$ may be hydrogen, methyl, amino, acetyl, carboxy, carboxamide, or hydroxy;

wherein when $X^7$ or $X^8$ is carbon, $W^7$ or $W^8$, respectively, may independently be hydrogen, $C_{1-6}$ alkyl, $C_{2-6}$ alkenyl, $C_{2-6}$ alkynyl, $C_{3-6}$ cycloalkyl, ($C_{3-6}$ cycloalkyl)methyl, phenyl, benzyl, five- or six-membered heterocyclyl, five- or six-membered heteroaryl, cyano, amino, acetyl, carboxy, hydroxy or $CONR^8R^9$;

wherein each of $R^8$ and $R^9$ is independently hydrogen, $C_{1-6}$ alkyl, $C_{2-6}$ alkenyl, $C_{2-6}$ alkynyl, $C_{3-6}$ cycloalkyl, ($C_{3-6}$ cycloalkyl)methyl, phenyl, benzyl, five- or six-membered heterocyclyl, five- or six-membered heteroaryl, or $OR^{10}$, or together with the nitrogen atom form a pyrrolidine, piperidine, morpholine, or pyrazine ring;

wherein $R^{10}$ is hydrogen, $C_{1-6}$ alkyl, $C_{2-6}$ alkenyl, $C_{2-6}$ alkynyl, $C_{3-6}$ cycloalkyl, ($C_{3-6}$ cycloalkyl)methyl, phenyl, benzyl, five- or six-membered heterocyclyl, or five- or six-membered heteroaryl;

or wherein $W^7$ or $W^8$ together form a five- or six-membered aryl, carbocyclic, heterocyclic, or heteroaryl ring fused with the B ring;

wherein $X^{2'}$ is hydrogen, hydroxy, or $OR^{2'}$;
wherein $X^{3'}$ is hydrogen, hydroxy, or $OR^{3'}$;
wherein $X^{5'}$ is $C(=X^4)X^{10}R$;
  wherein $X^4$ is O or $H_2$;
  wherein $X^{10}$ is $C(H)NR^{11}R^{12}$, $NR^1$, or S;
    wherein $R^{11}$ and $R^{12}$ each is independently hydrogen, $C_{1-4}$ alkyl, $C_2$-$C_{2-3}$ alkenyl, $C_{2-3}$ alkynyl, $C_{3-6}$ cycloalkyl, phenyl, benzyl, or acetyl, or together with the nitrogen atom form an aziridine, azetidine, pyrrolidine, piperidine, morpholine, or pyrazine ring;
    wherein R and $R^1$ each is independently hydrogen, $C_{1-8}$ alkyl, $C_{2-6}$ alkenyl, $C_{2-6}$ alkynyl, $C_{3-6}$ cycloalkyl, $C_{6-10}$ aryl, five-to-ten-membered heteroaryl, five- to ten-membered heterocyclyl, $C_{1-8}$ acyl, or [(S)-2-aminobutanoic acid]-4-yl,
wherein any alkyl, alkenyl, alkynyl, cycloalkyl, heterocyclyl, aryl or heteroaryl ring is optionally substituted with one or more of fluoro, chloro, bromo, iodo, $C_{1-6}$ alkyl, $C_{2-6}$ alkenyl, $C_{2-6}$ alkynyl, methoxy, ethoxy, trifluoromethoxy, trifluoromethyl, hydroxy, thiomethyl, cyano, $NR^8R^9$, —$N(H)C(=O)X^{11}$, acetyl, carboxy, carboxy($C_{1-4}$ alkyl), or $CONR^8R^9$;
  wherein $X^{11}$ is $C_{1-6}$ alkyl, $C_{2-6}$ alkenyl, $C_{2-6}$ alkynyl, $C_{3-6}$ cycloalkyl, ($C_{3-6}$ cycloalkyl)methyl, phenyl, benzyl, $OR^{10}$, or $NR^8R^9$; and
wherein one of $R^2$, $R^{2'}$ (if it exists), and $R^{3'}$ (if it exists), comprises a linker component, wherein the linker component comprises a linker moiety bonded to a fluorophore moiety, and the other existing of $R^2$, $R^{2'}$, and $R^{3'}$ are hydrogen, and wherein $R^2$, when not hydrogen, substitutes a hydrogen atom of the B ring or a ring fused to the B ring or a functional group covalently bound to the B ring or a ring fused to the B ring.

Another exemplary embodiment may be directed to a fluorescent detection analyte having the structure of Formula (II):

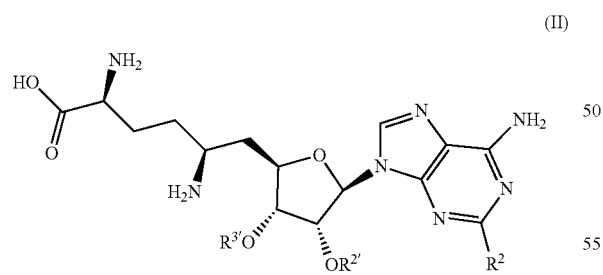

(II)

wherein any two of $R^2$, $R^{2'}$, and $R^{3'}$ comprises hydrogen and the third comprises a linker component, wherein the linker component comprises a linker moiety bonded to a fluorophore moiety;

Another exemplary embodiment may be directed to a fluorescent detection analyte having the structure of Formula (III):

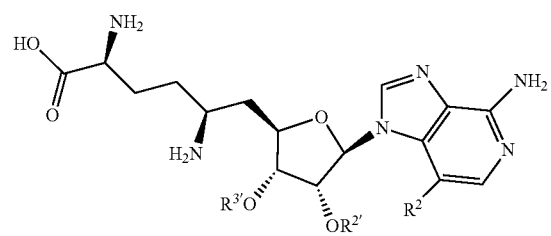

(III)

wherein any two of $R^2$, $R^{2'}$, and $R^{3'}$ comprises hydrogen and the third comprises a linker component, wherein the linker component comprises a linker moiety bonded to a fluorophore moiety.

Another exemplary embodiment may be directed to a fluorescent detection analyte having the structure of Formula (IV):

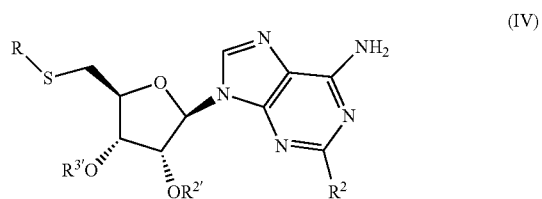

(IV)

wherein any two of $R^2$, $R^{2'}$, and $R^{3'}$ comprises hydrogen and the third comprises a linker component, wherein the linker component comprises a linker moiety bonded to a fluorophore moiety and wherein R is hydrogen, $C_{1-8}$ alkyl, $C_{2-6}$ alkenyl, $C_{2-6}$ alkynyl, $C_{3-6}$ cycloalkyl, $C_{6-10}$ aryl, five-to-ten-membered heteroaryl, five- to ten-membered heterocyclyl, $C_{1-8}$ acyl, or [(S)-2-aminobutanoic acid]-4-yl.

Another exemplary embodiment may be directed to a fluorescent detection analyte having the structure of Formula (V):

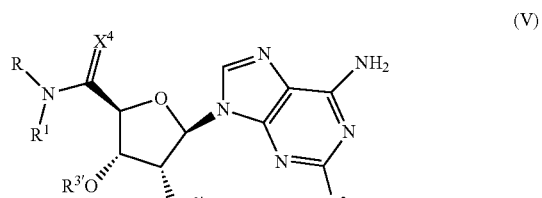

(V)

wherein any two of $R^2$, $R^{2'}$, and $R^{3'}$ comprises hydrogen and the third comprises a linker component, wherein the linker component comprises a linker moiety bonded to a fluorophore moiety;

wherein R and $R^1$ are each independently hydrogen, $C_{1-8}$ alkyl, $C_{2-6}$ alkenyl, $C_{2-6}$ alkynyl, $C_{3-6}$ cycloalkyl, $C_{6-10}$ aryl, five-to-ten-membered heteroaryl, five- to ten-membered heterocyclyl, $C_{1-8}$ acyl, or [(S)-2-aminobutanoic acid]-4-yl; and wherein $X^4$ is O or $H_2$.

As noted above, each of the detection analytes according to Formulas (I)-(V) includes a linker moiety. In certain embodiments associated with Formulas (I)-(V), the linker moiety comprises a structure as illustrated in Formula (VI) or Formula (VII):

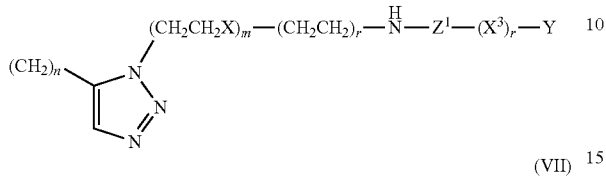
(VI)

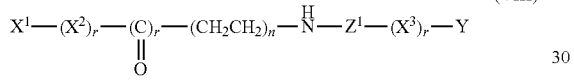
(VII)

wherein when $R^2$ comprises the linker component, the linker moiety may alternatively comprise a structure as illustrated in Formula (VIII):

(VIII)
$$X^1—(X^2)_r—(C)_r—(CH_2CH_2)_n—\overset{H}{N}—Z^1—(X^3)_r—Y$$
$$\overset{\|}{O}$$

wherein the $(CH_2)_n$ group of Formula (IV) or the $(CH_2)_s$ group of Formula (V) comprises the site of covalent attachment at one of $R^2$, $R^{2'}$, and $R^{3'}$ of Formulas (I), (II), and (III);
wherein X is $CH_2$ or O;
wherein $X^1$ is N—H, N—$CH_3$, O, or S;
wherein $X^2$ is N—H, N—$CH_3$, or, when r is 0 and $X^1$ is N—H or N-Me, $X^2$ may alternatively be O;
wherein $X^3$ is NH or O;
wherein $Z^1$ is a carbonyl, thiocarbonyl, or sulfonyl group;
wherein Y is a covalent bond that binds the linker moiety to the fluorophore moiety, or $(CH_2)_n$ wherein the last $CH_2$ group in the chain (when n is not 0) is farthest from $Z^1$ is covalently bound to the fluorophore moiety, or
$(CH_2)_n$—N(H)—$Z^2$, or is of the chemical structure:

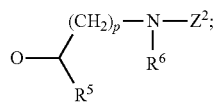

wherein the oxygen atom end is covalently bound to $Z^1$;
wherein each $R^5$ and $R^6$ is independently H, methyl, or together are $(CH_2)_q$;
wherein q is 1, 2, or 3;
wherein p is 1 or 2; and
wherein $Z^2$ is a carbonyl or thiocarbonyl group covalently bound by its carbon atom to the fluorophore moiety, or a sulfonyl group covalently bound by sulfur atom to the fluorophore moiety;
wherein each n is independently 0, 1, 2, 3, 4, or 5;
wherein s is 1, 2, or 3;
wherein m is 1, 2, or 3;
wherein each r is independently 0 or 1;
wherein the fluorophore moiety is a structure selected from the group of chemical structures consisting of:

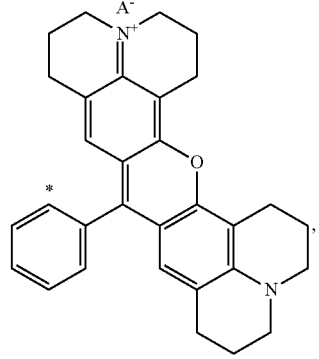
(a)

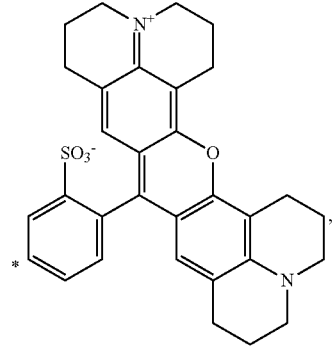
(b)

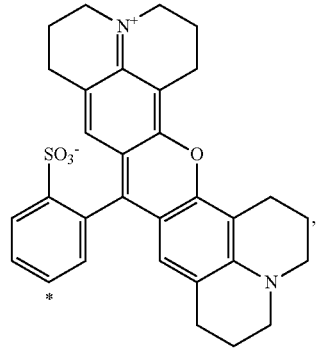
(c)

(d)
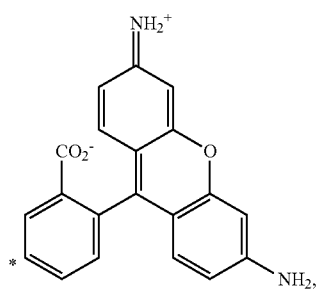
(e)
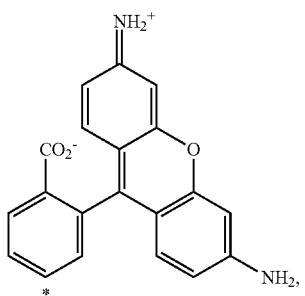
(f)
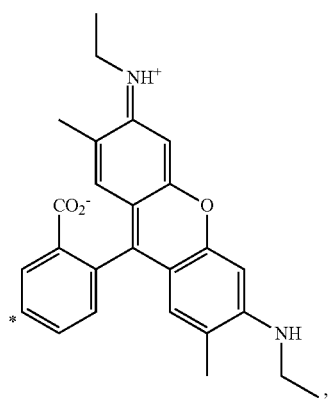
(g)
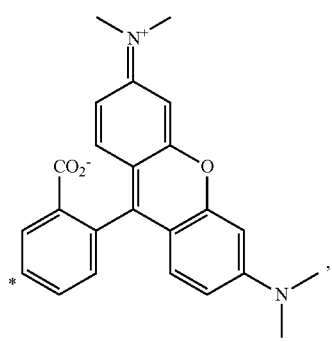
(h)
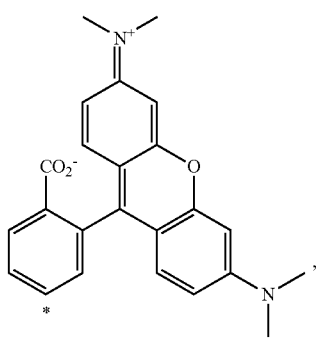
(i)
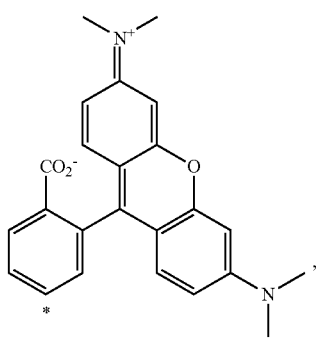
(j)
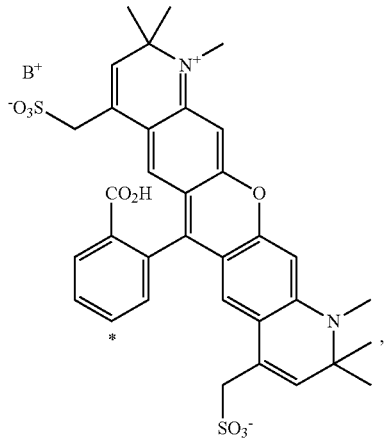

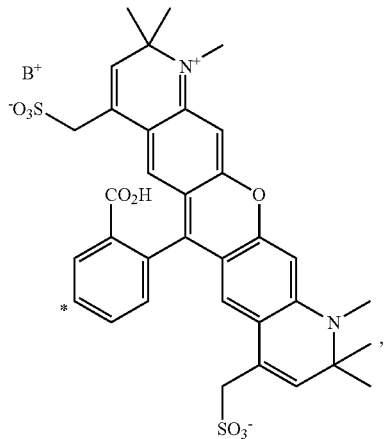

(k)

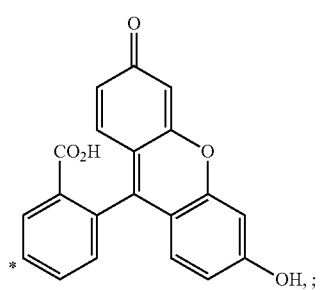

(l)

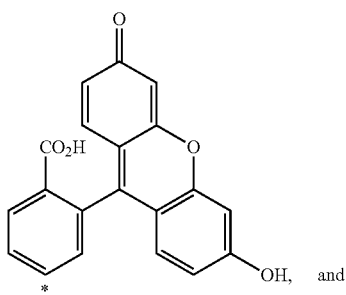

(m)

(n)

wherein * represents the position at which the linker moiety is covalently bound to the fluorophore moiety;

wherein A⁻ is a $PF_6^-$, trifluoroacetate, acetate, or halide anion;

wherein B⁺ is a sodium, potassium, cesium, ammonium, or ⁺$N(R^4)_4$ cation; and wherein each $R^4$ is independently H or $C_{1-4}$ alkyl.

An exemplary detection analyte embodiment of any of Formulas (I)-(V) comprises a fluorophore moiety mixture that is a fluorophore regioisomer pair, such as one of the pairs (b) and (c); (b) and (n); (d) and (e); (f) and (g); (h) and (i); and (j) and (k).

An exemplary detection analyte embodiment of any of Formulas (I)-(V) comprises a fluorophore moiety that is a salt mixture having more than one kind of anion A⁻ or cation B⁺; for example, an exemplary detection analyte embodiment may comprise a fluorophore moiety (a) salt mixture wherein A⁻ is a $PF_6^-$ and trifluoroacetate anion mixture.

Another exemplary embodiment may be directed to a fluorescent detection analyte selected from the group consisting of:

Sinefungin Probe 1A, Sinefungin Probe 1B, Sinefungin Probe 2A,

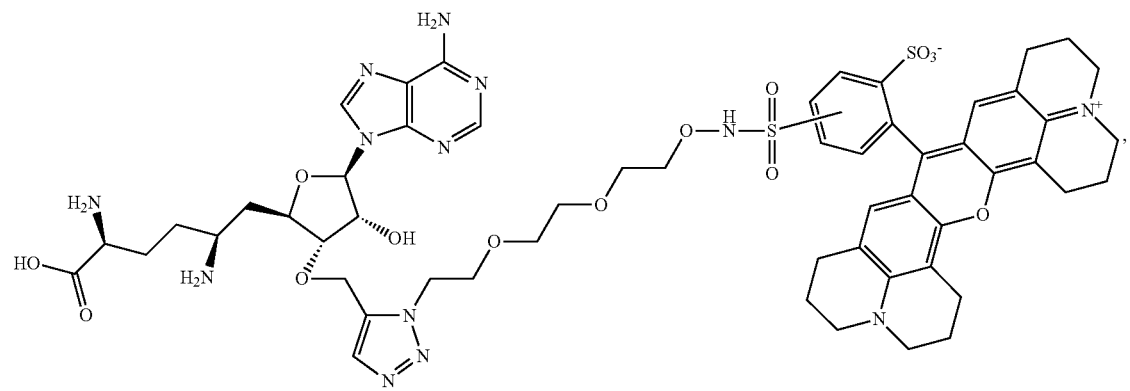

(Sinefungin Probe 2B)

-continued
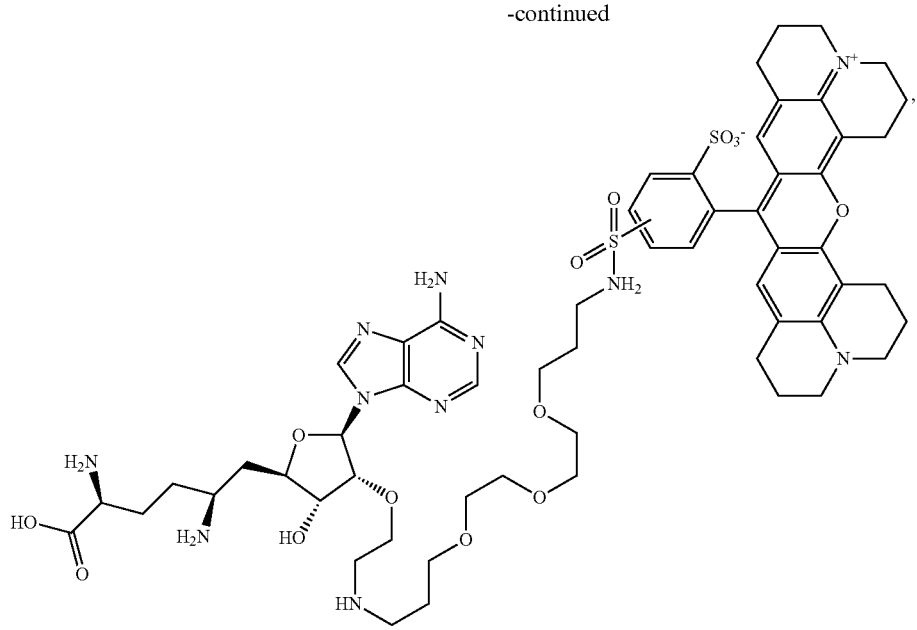
(Sinefungin Probe 3)
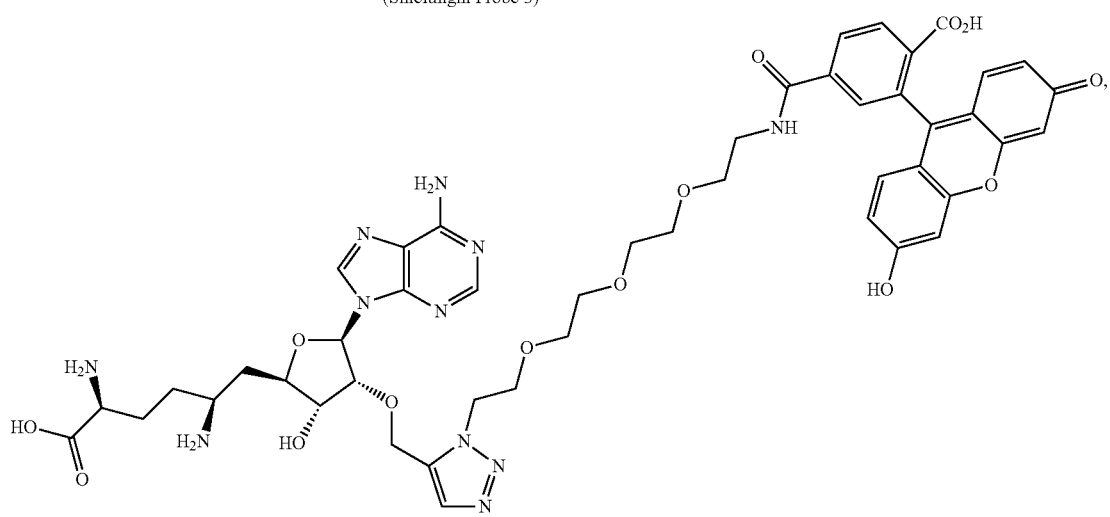
(Sinefungin Probe 4)
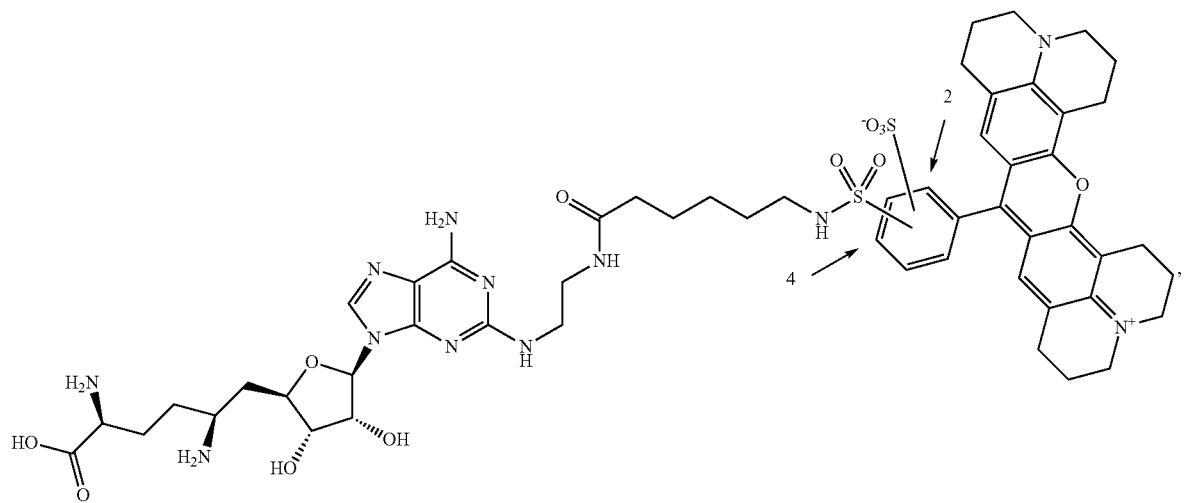
(Sinefungin Probe 5)

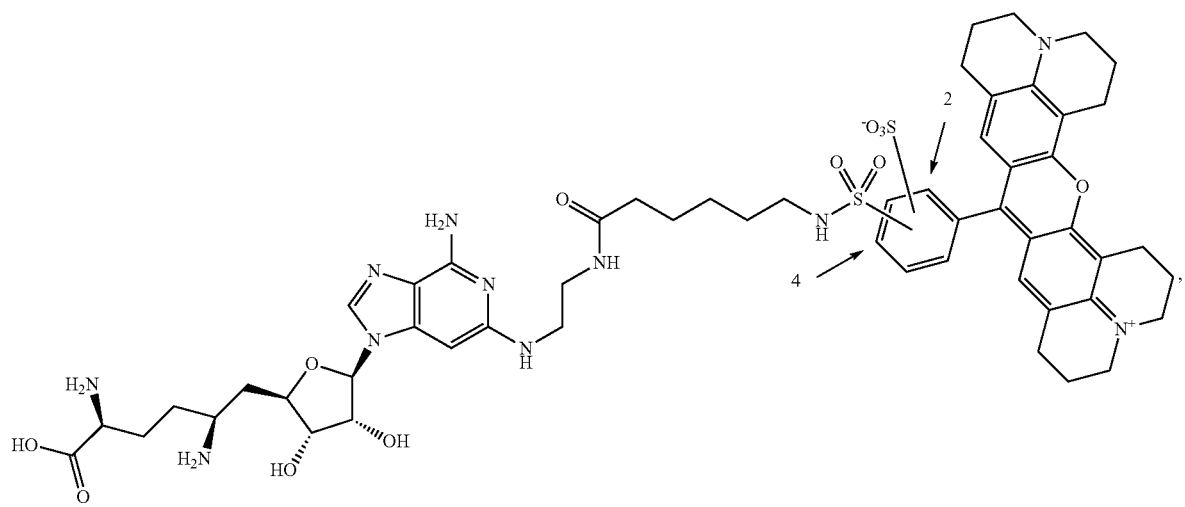
(Sinefungin Probe 6)
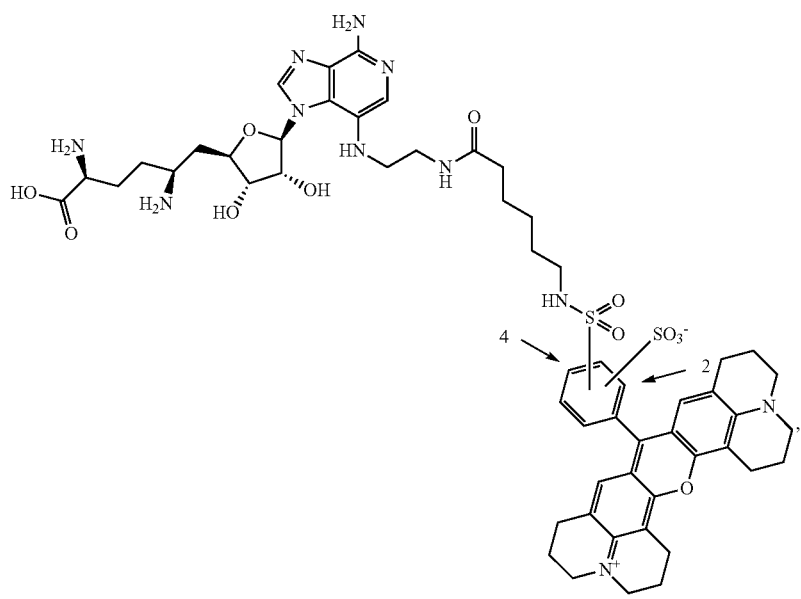
(Sinefungin Probe 7)
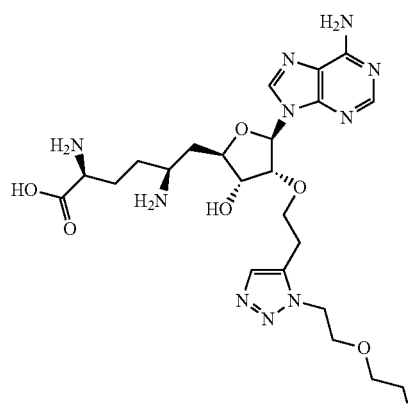

-continued
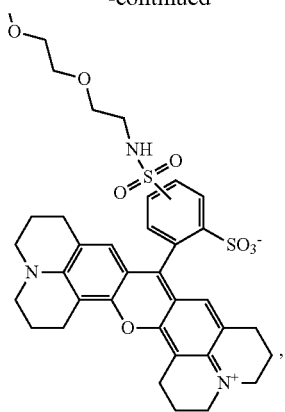
(Sinefungin Probe 8)
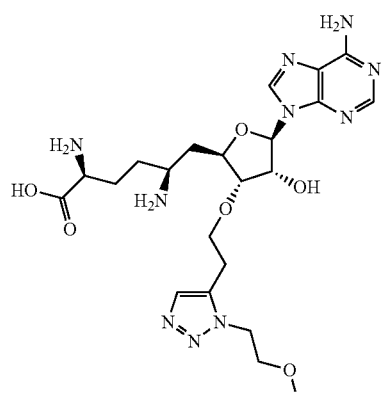
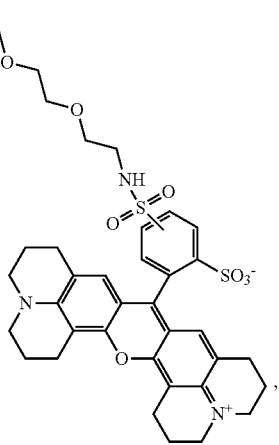
(Sinefungin Probe 9)

-continued
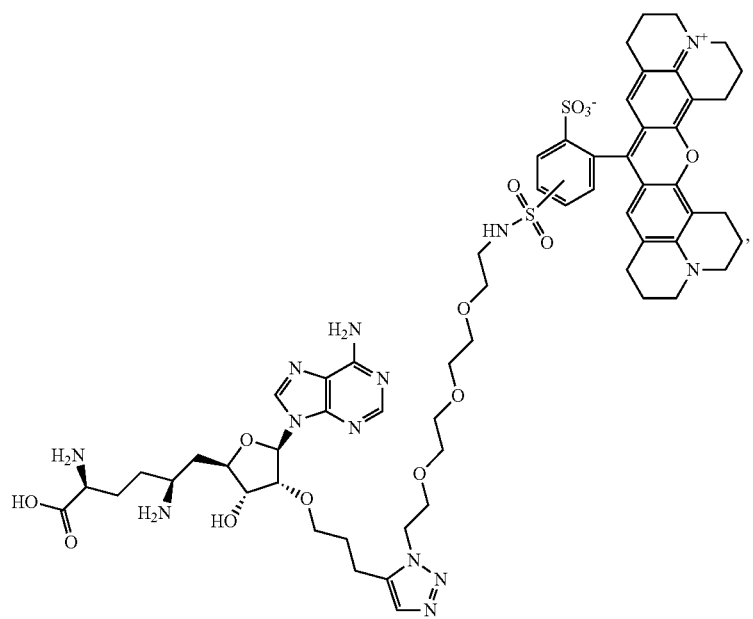
(Sinefungin Probe 10)
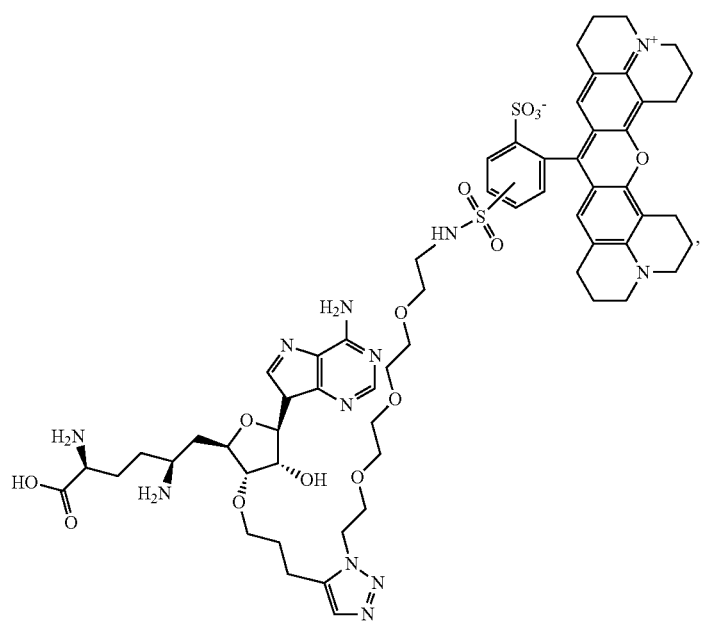
(Sinefungin Probe 11)

-continued
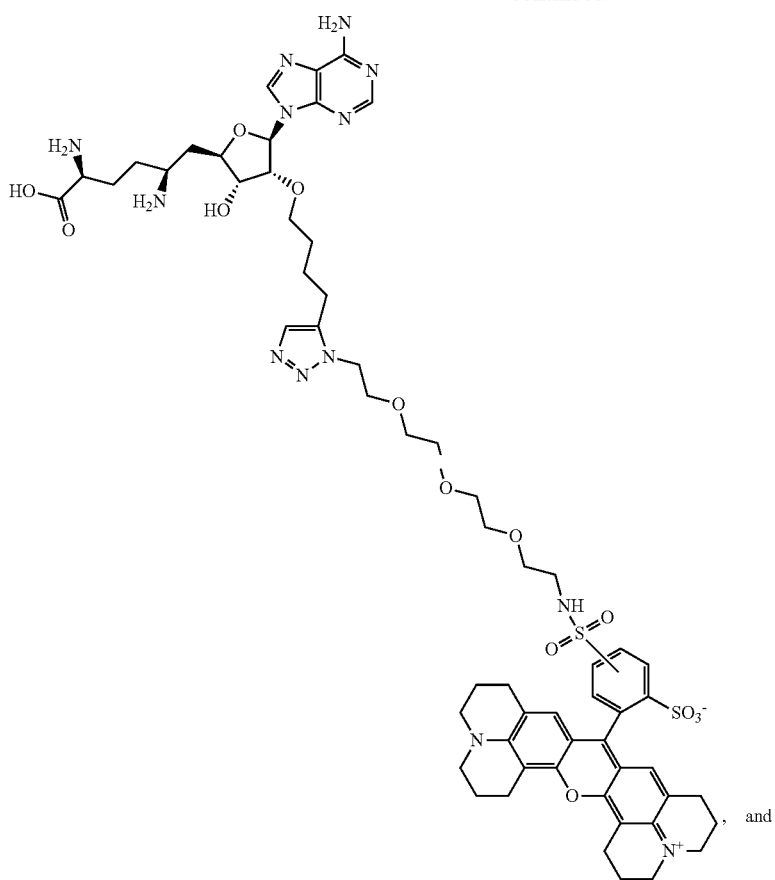
(Sinfungin Probe 12)
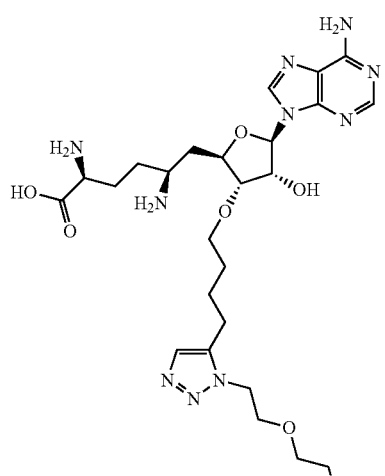

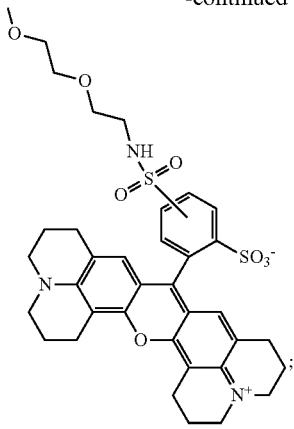

(Sinefungin Probe 13)

wherein any A⁻ is $PF_6^-$, halide, acetate, or trifluoroacetate, or a mixture thereof.

Another exemplary embodiment may be directed to a fluorescent detection analyte selected from the group consisting of:
Thioadenosine Probe 1 and

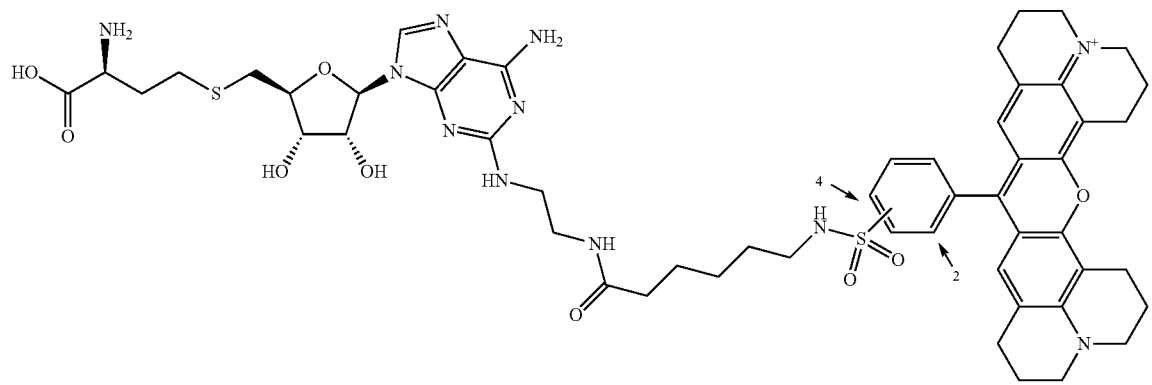

(Thioadenosine Probe 2)

For all exemplary embodiments herein, the drawings that include "4→" and "2→" elements represent a regioisomeric mixture wherein each of the two groups with undefined covalent attachment to the phenyl ring may be covalently bound at either the "2-" or "4-" position as indicated, with the other of the two groups is covalently bound at the other of the "2-" or "4-" positions of the phenyl ring. The regioisomers may or may not be present in equal amounts in the mixture.

Another exemplary embodiment may be directed to a fluorescent detection analyte selected from the group consisting of:

Aza-adenosine Probe 1, Aza-adenosine Probe 3,
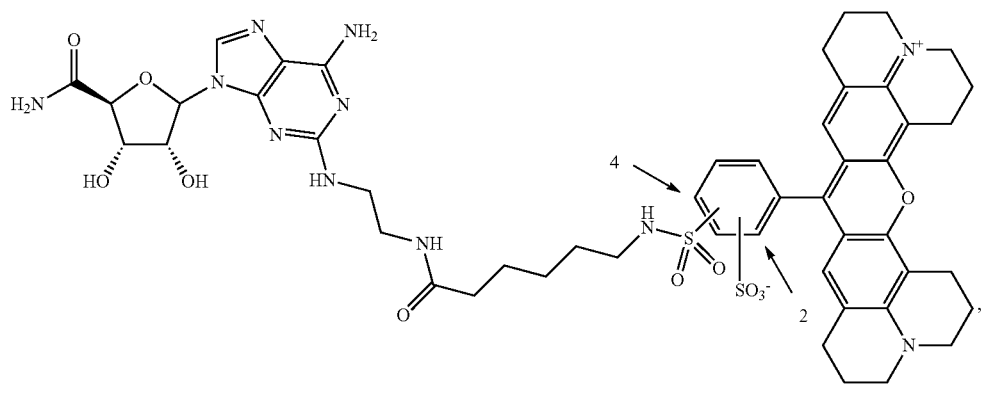
(Aza-adenosine Probe 5)
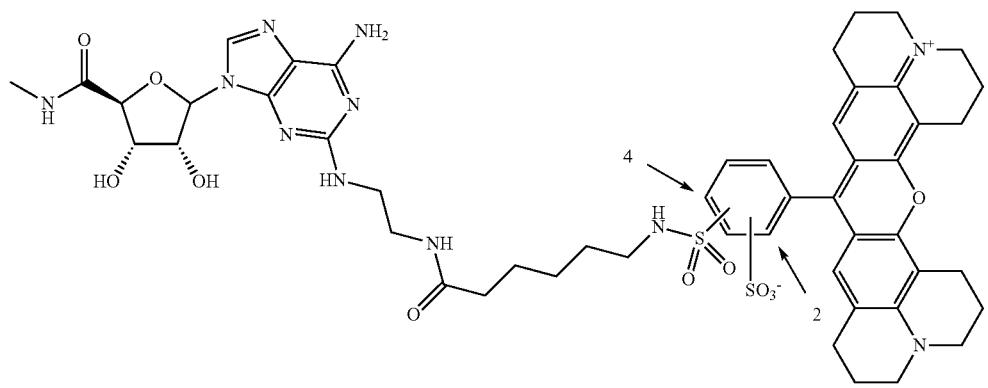
(Aza-adenosine Probe 6)
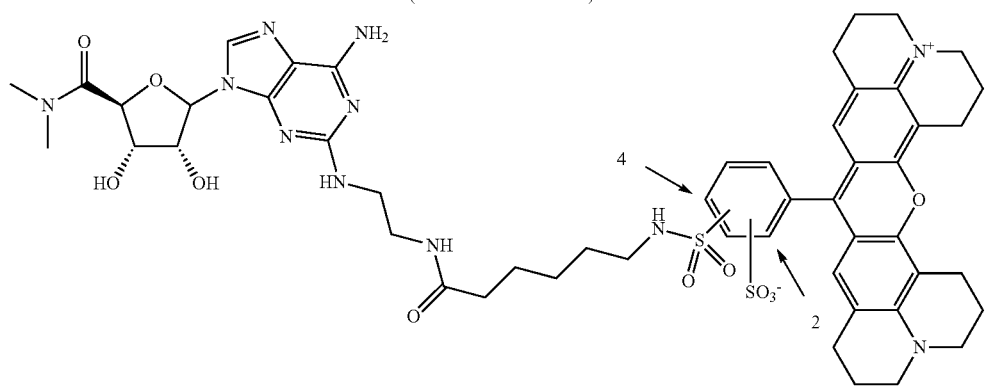
(Aza-adenosine Probe 7)
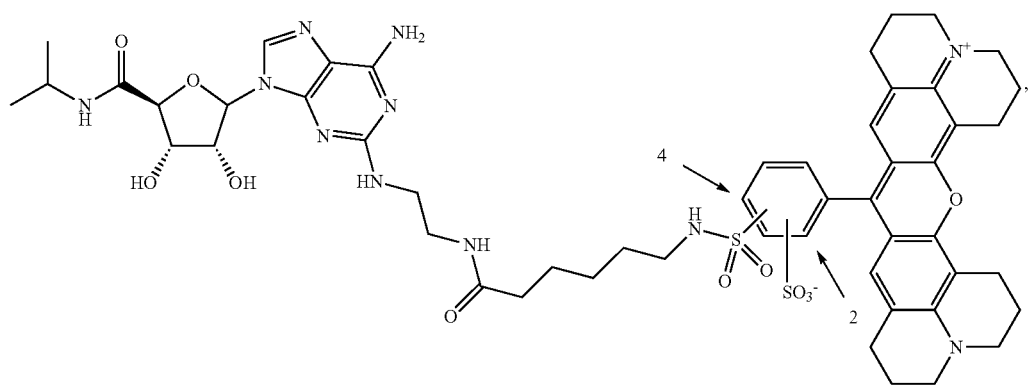
(Aza-adenosine Probe 8)

-continued
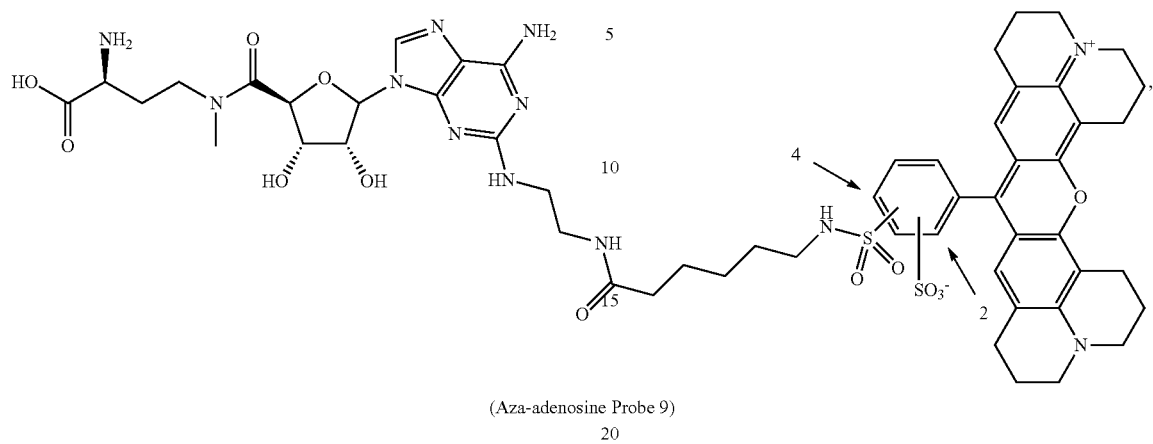
(Aza-adenosine Probe 9)
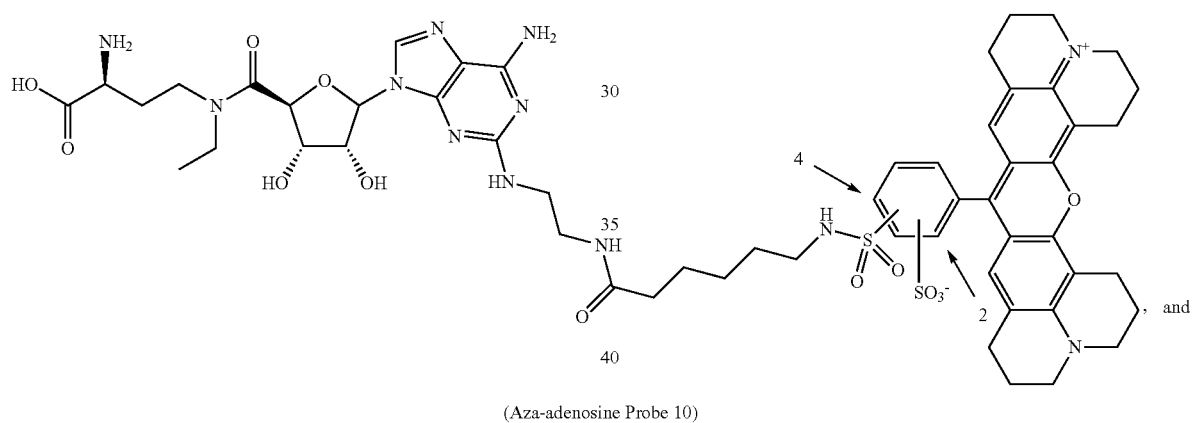
, and
(Aza-adenosine Probe 10)
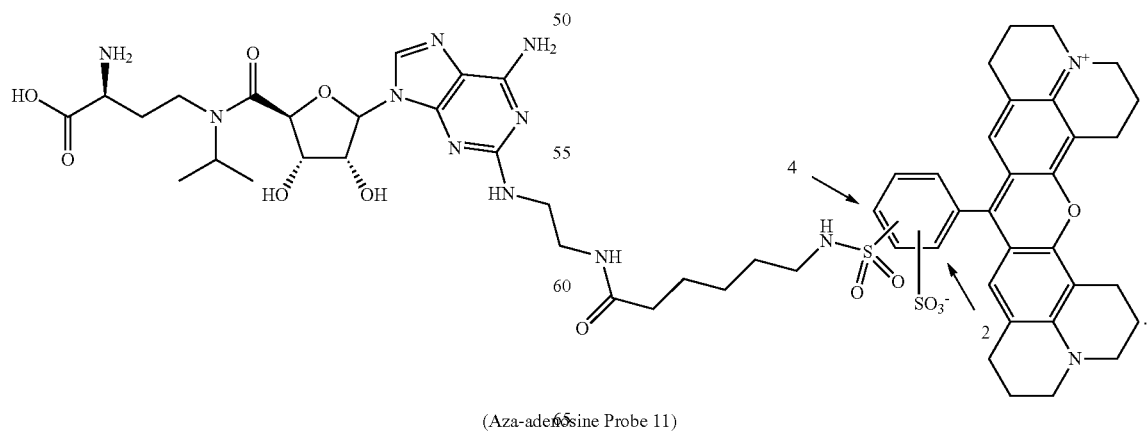
(Aza-adenosine Probe 11)

Another exemplary embodiment may be directed to a fluorescent detection analyte selected from the group consisting of:
(Aza-adenosine Probe 2), (Aza-adenosine Probe 4),
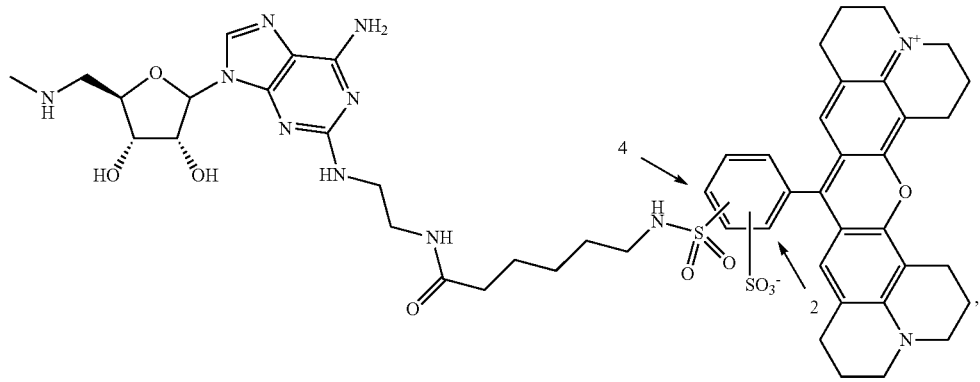
(Aza-adenosine Probe 12)
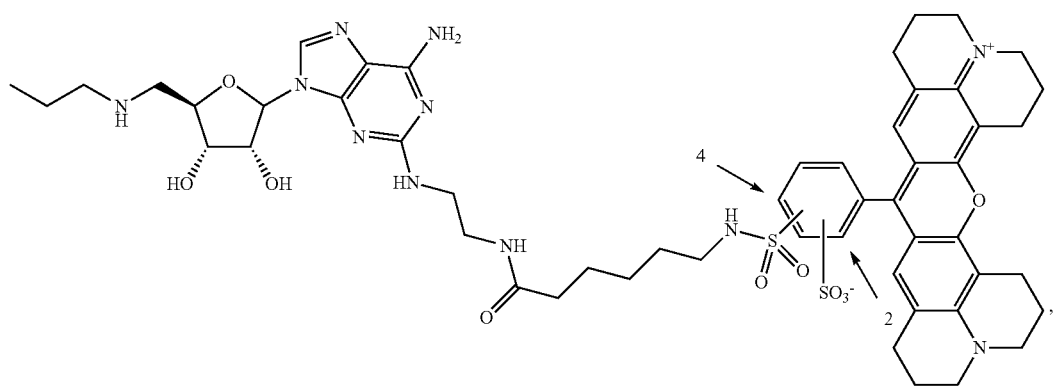
(Aza-adenosine Probe 13)
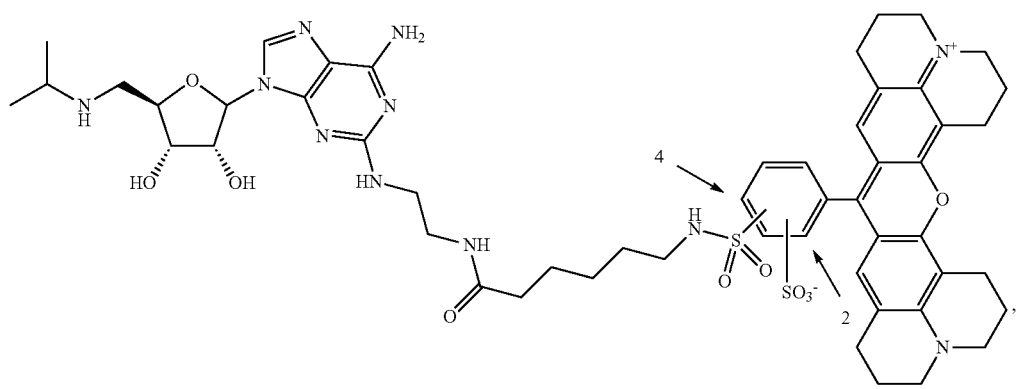
(Aza-adenosine Probe 14)

-continued
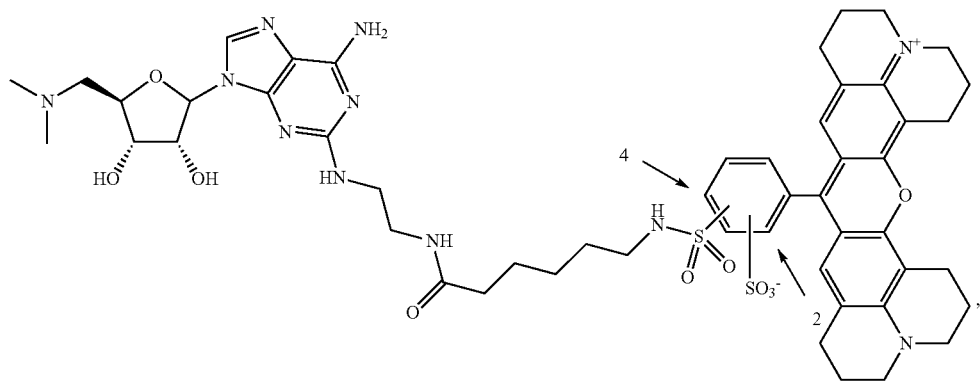
(Aza-adenosine Probe 15)
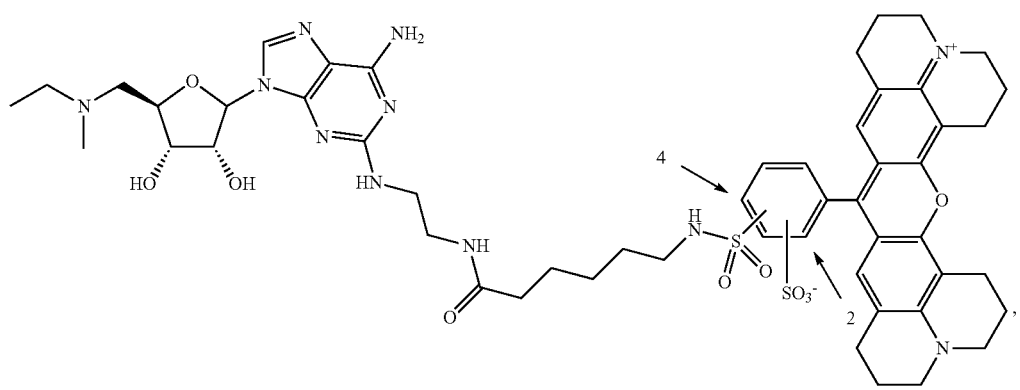
(Aza-adenosine Probe 16)
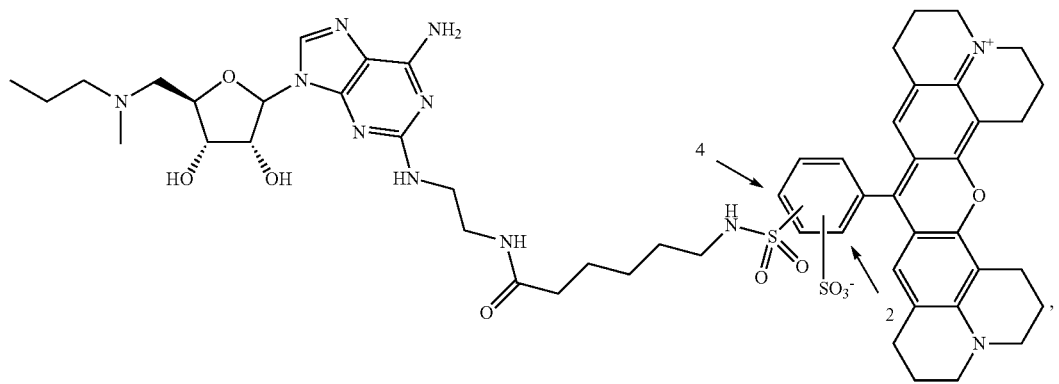
(Aza-adenosine Probe 17)
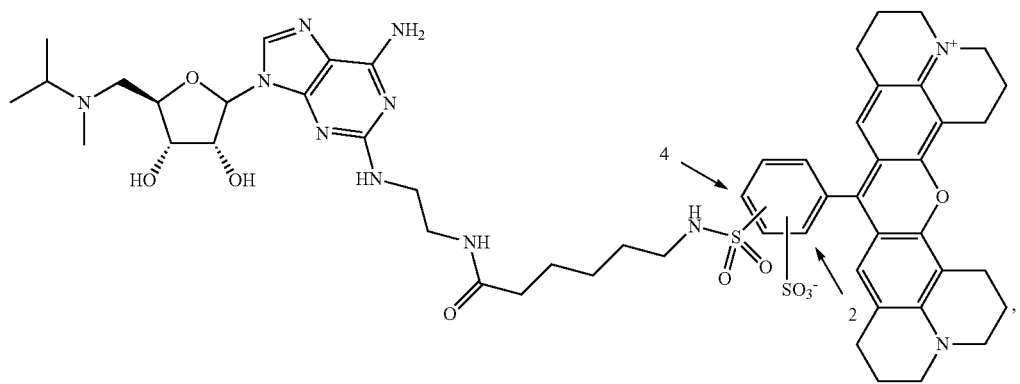
(Aza-adenosine Probe 18)

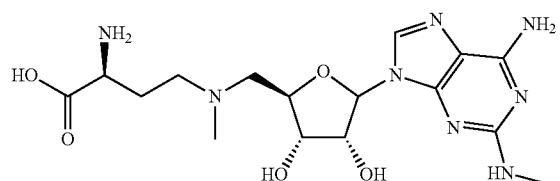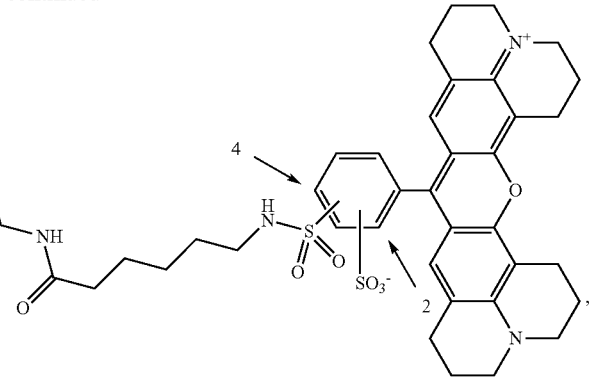

(Aza-adenosine Probe 19)

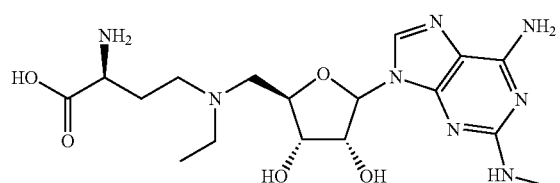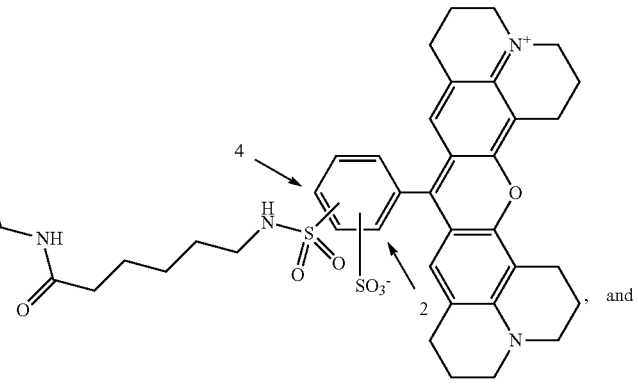

(Aza-adenosine Probe 20)

, and

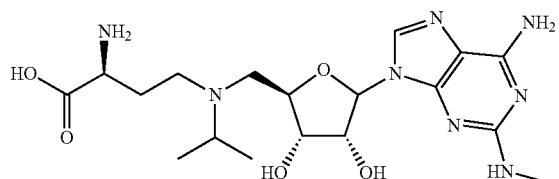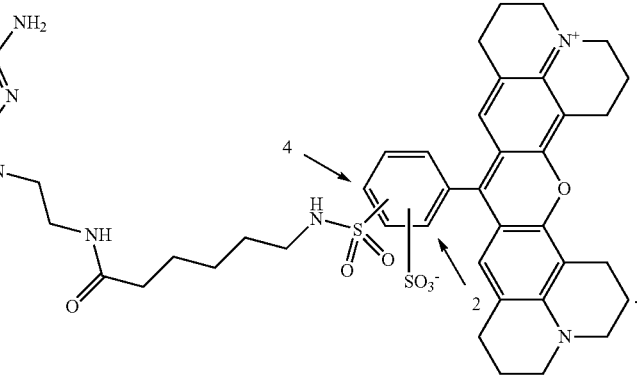

(Aza-adenosine Probe 21)

.

Detection analytes of the exemplary embodiments comprising a sinefungin moiety covalently bound to the linker moiety at its 2'- or 3'-hydroxy oxygen were prepared generally according to the synthetic scheme described in FIG. 1, wherein the N-protection reaction of Step 1, the O-derivatization reaction of Step 2, the deprotection reaction of Step 3, and the fluorophore moiety attachment reaction of Step 4 are carried out by methods known in the art to provide a fluorescent detection analyte product mixture comprising at least one compound selected from the group consisting of a Compound 1A, a Compound Regioisomer Mixture 1B, and a Compound 2. The N-protection reactions of Step 1 include but are not limited to tert-butoxycarbonyl (Boc) protections that are carried out by contacting sinefungin (Compound 3)

with suitable amounts of di-tert-butyl dicarbonate (Boc$_2$O) and a suitable base such as sodium hydroxide in a solvent or solvent mixture such as water-dioxane. The O-derivatization reactions of Step 2 may take place by contacting an intermediate Compound 4 with an appropriate acetylene electrophile and a suitable base in a suitable solvent or solvent mixture to provide an intermediate comprising at least one compound selected from the group consisting of a Compound 5 and a Compound 6. The deprotection reactions of Step 3 may be carried out with known conditions suitable for removal of the nitrogen-protecting groups to provide an intermediate comprising at least one compound selected from the group consisting of a Compound 7 and a Compound 8. For example, Boc protecting groups may be removed by contacting an appropriately-protected intermediate prepared by Step 2 with a suitable amount of an acid such as trifluoroacetic acid (TFA). The fluorophore moiety attachment reactions of Step 4 may subsequently be carried out by contacting an intermediate prepared by Step 3 with a reagent comprising an appropriate fluorophore covalently linked to an azide group in a reaction mixture further comprising suitable amounts of copper(II) sulfate, sodium ascorbate, and a suitable solvent or solvent system such as water-DMF to provide a fluorescent detection analyte product comprising at least one compound selected from the group consisting of a Compound 1A, a Compound Regioisomer Mixture 1B, and a Compound 2.

Figure 9:
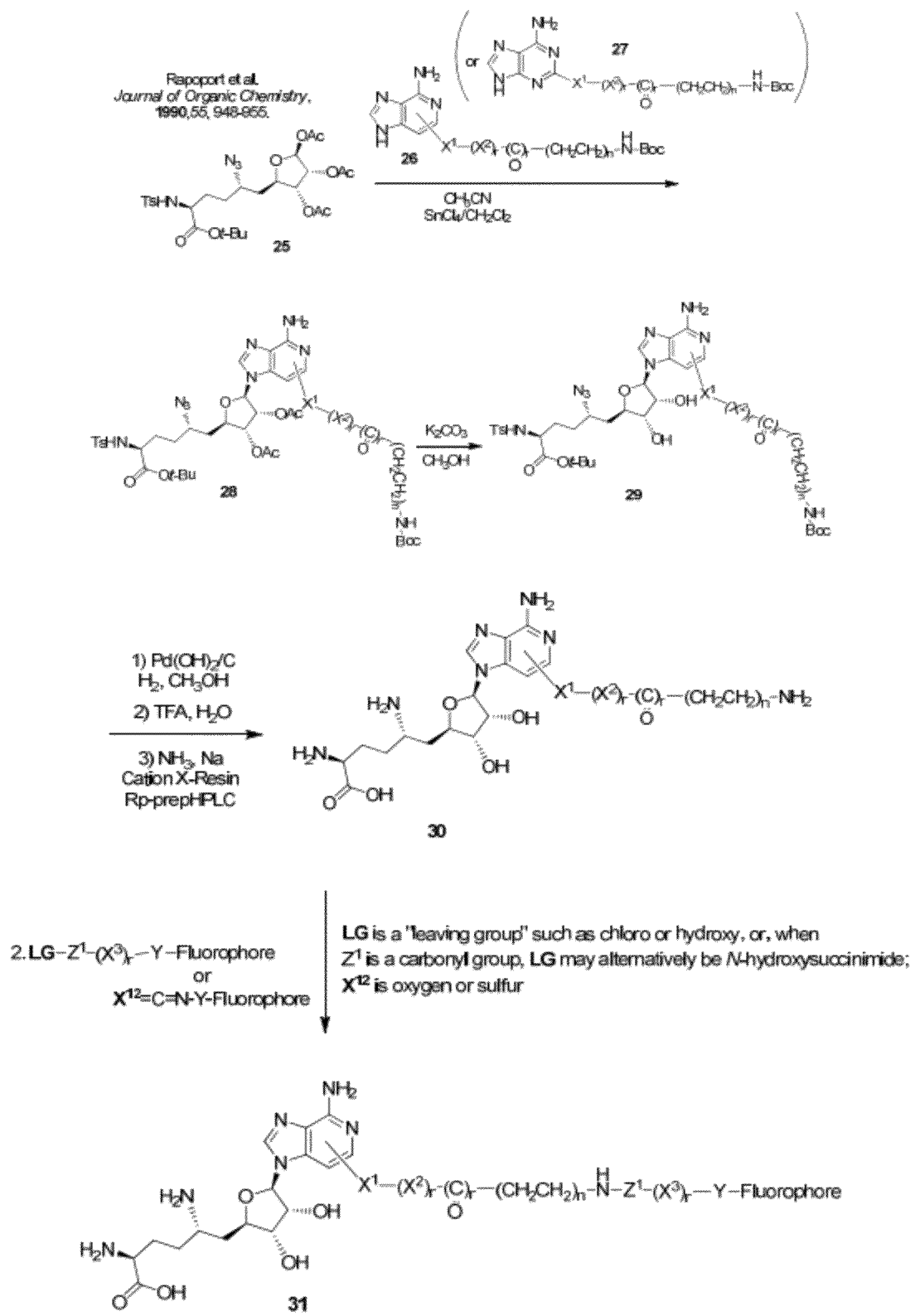
FIG. 9 illustrates a general synthetic pathway for preparing sinefungin fluorescent detection analytes and sinefungin analog fluorescent detection analytes wherein the linker moiety is attached to the adenine ring or adenine ring replacement portion.
Figure 9A:
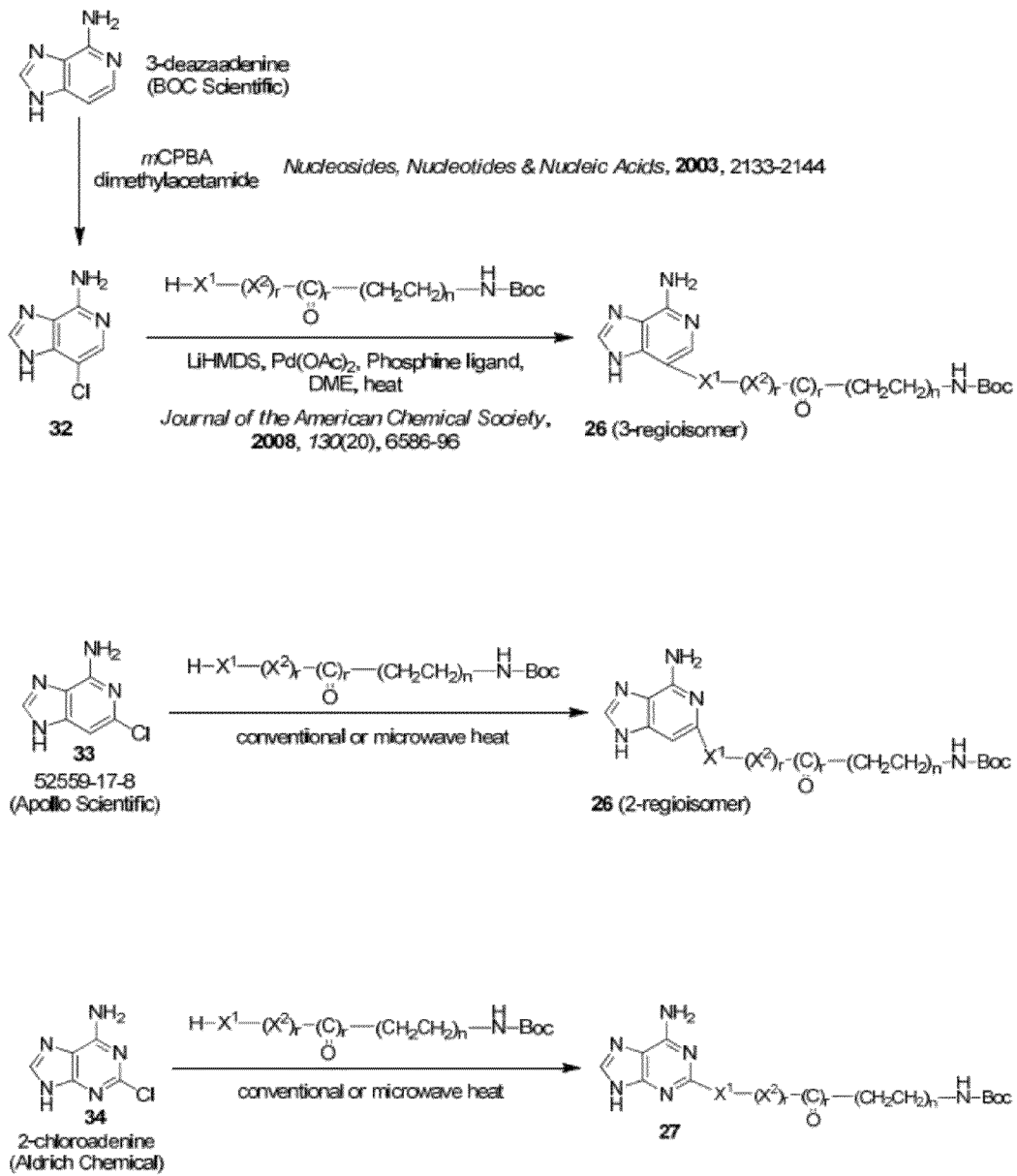
FIG. 9A illustrates general synthetic pathways for obtaining various sinefungin base ring portions covalently bound to linker moieties or linker moiety precursors.

Detection analytes of the exemplary embodiments comprising a sinefungin moiety covalently bound to the linker moiety at its base ring are prepared generally according to the synthetic scheme illustrated in FIG. 9, wherein the syntheses proceed through Compound 25. The synthesis of Compound 25 is described by Rapoport et al in the *Journal of Organic Chemistry*, 1990, 55, 948-955. Preparation of various base ring portions of the sinefungin moiety wherein various linker moieties or a linker moiety precursors are covalently bound to the base ring portion are generally illustrated in FIG. 9A.

Detection analytes of the exemplary embodiments comprising a sinefungin moiety are alternatively prepared using other methods known in the art, including those that comprise the assembly of sinefungin probes comprising linker moieties having the general structures represented by Formulas (VI), (VII), and (VIII).

Figure 5:
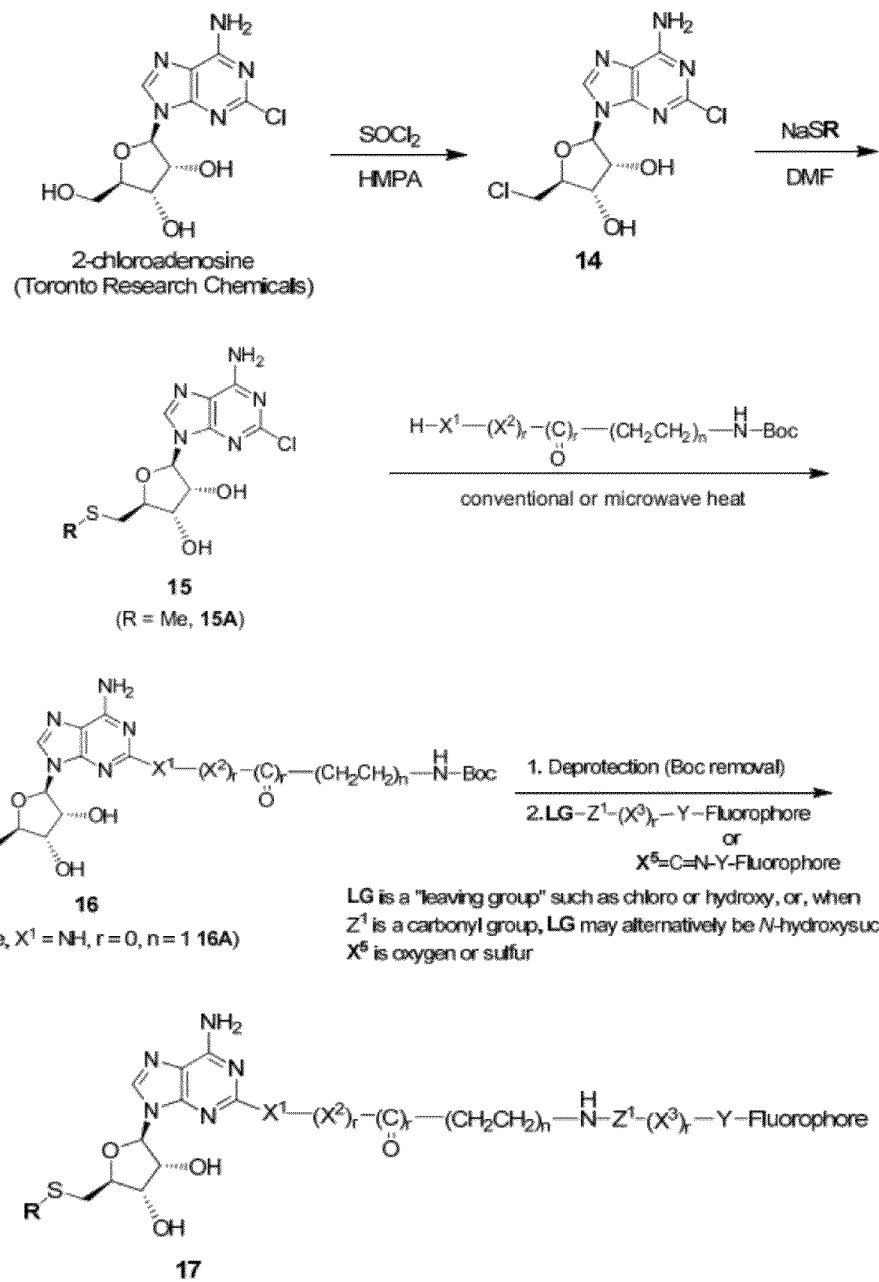
FIG. 5 illustrates a general synthetic pathway for preparing thioadenosine fluorescent detection analytes.

Detection analytes of the exemplary embodiments comprising a thioadenosine moiety were prepared generally according to the synthetic scheme illustrated in FIG. 5. Commercially-available 2-chloroadenosine may be subjected to chlorination conditions to provide the 2,5'-dichloro-5'-deoxy-adenosine (Compound 14), which may be subsequently reacted with a thiol or thiolate anion to provide the corresponding S-substituted-2-chloro-5'-thioadenosine intermediate (Compound 15). The S-substituted-2-chloro-5'-thioadenosine intermediate was treated with a reagent comprising a linker moiety or a linker moiety precursor of Formula (VIII), the nucleophilic end ($X^1-$) of which reacts with the S-substituted-2-chloro-5'-thioadenosine intermediate at the adenine-2-carbon position of the adenine portion of the nucleoside moiety, displacing the 2-chloro group, forming the Boc-protected intermediate of the general structure represented as Compound 16. Deprotection and subsequent addition of the fluorophore reagent under appropriate conditions afforded thioadenosine detection analytes of the general structure represented as Compound 17.

Figure 6:
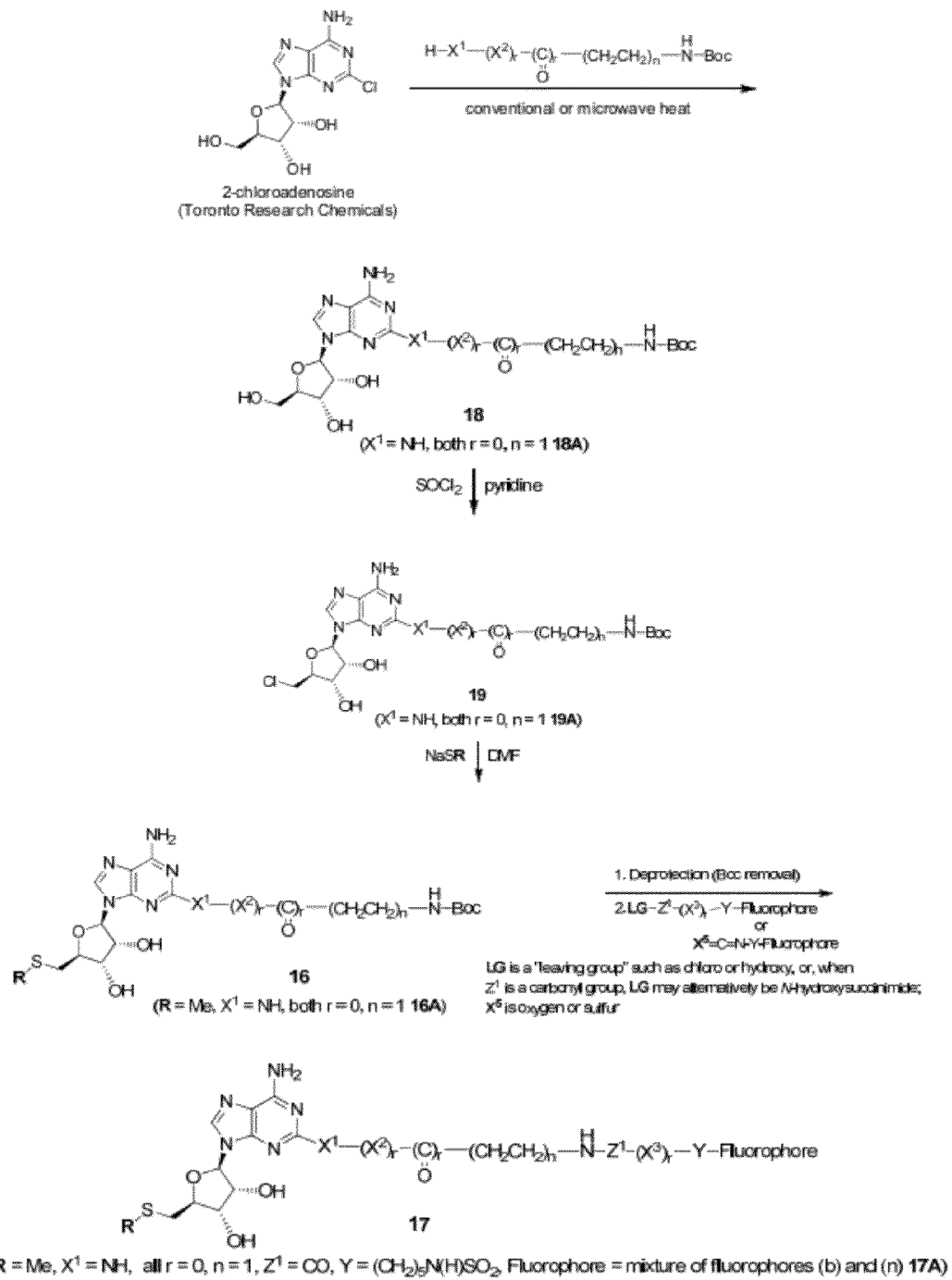
FIG. 6 illustrates an alternative general synthetic pathway for preparing thioadenosine fluorescent detection analytes.

Detection analytes of the exemplary embodiments comprising a thioadenosine moiety are alternatively prepared generally according to the synthetic scheme illustrated in FIG. 6. 2-Chloroadenosine is treated with a reagent comprising a linker moiety or a linker moiety precursor of Formula (VIII), the nucleophilic end ($X^1-$) of which reacts with 2-chloroadenosine at the adenine-2-carbon position, displacing the 2-chloro group, forming the Boc-protected intermediate of the general structure represented as Compound 18. Subjection of intermediates of the general structure represented as Compound 18 to chlorination conditions afford the 5'-chloro intermediates of the general structure represented as Compound 19. Addition of the appropriate thiol or thiolate provides intermediates of the general structure represented as Compound 16, which may be carried forward to the corresponding detection analytes according to the general route described above.

Detection analytes of the exemplary embodiments comprising a thioadenosine moiety are alternatively prepared using other methods known in the art, including those that comprise the assembly of thioadenosine probes comprising linker moieties having the general structures represented by Formulas (VI), (VII), and (VIII).

Figure 8:
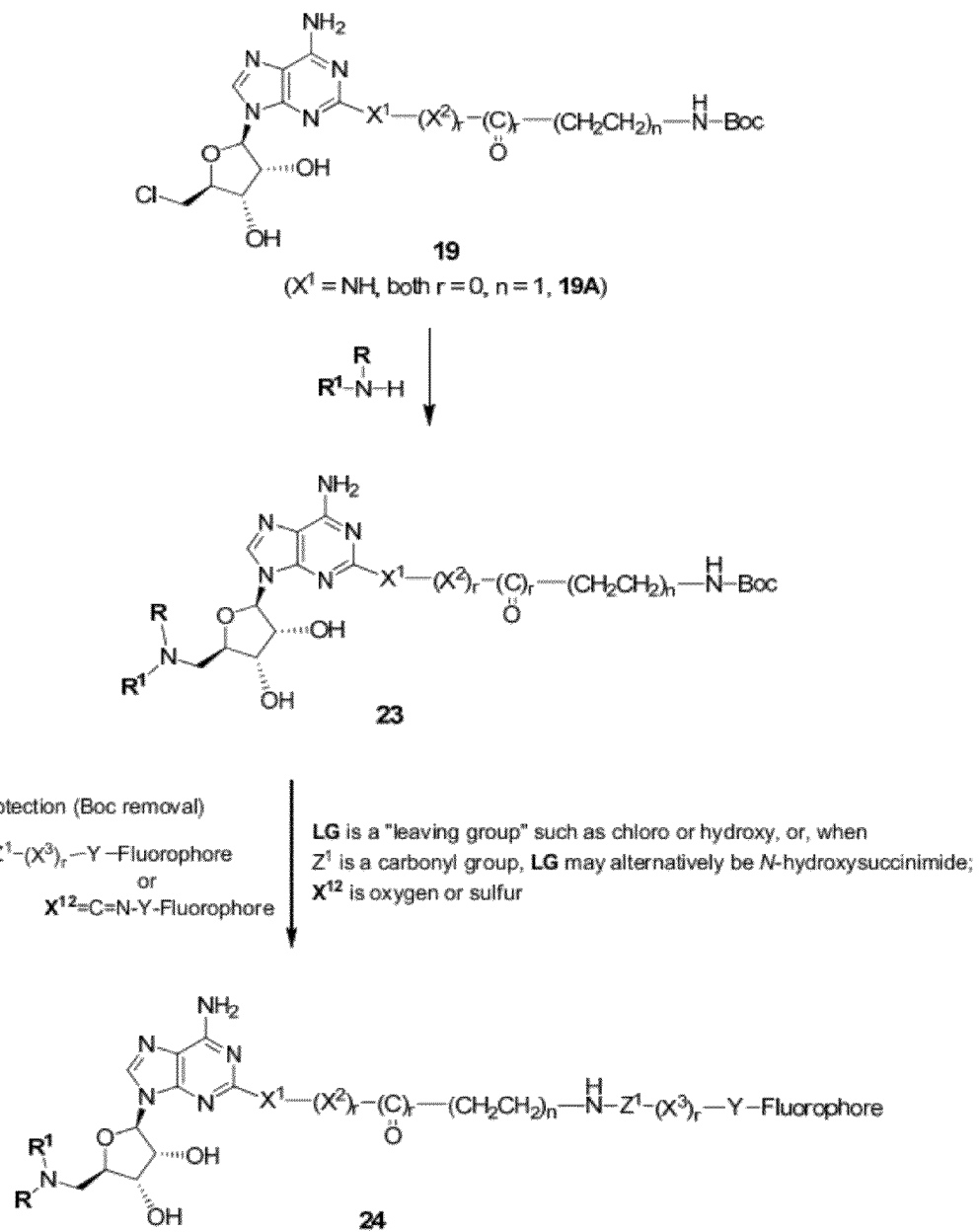
FIG. 8 illustrates an alternative general synthetic pathway for preparing aza-adenosine fluorescent detection analytes.

Detection analytes of the exemplary embodiments comprising an aza-adenosine moiety are prepared generally according to the synthetic schemes illustrated in FIGS. 7 and 8.

Detection analytes of the exemplary embodiments comprising an aza-adenosine moiety are alternatively prepared using other methods known in the art, including those that comprise the assembly of aza-adenosine probes comprising linker moieties having the general structures represented by Formulas (VI), (VII), and (VIII).

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well known and commonly used in the art.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

EXAMPLES

Liquid chromatography—mass spectra (LC/MS) were obtained using an Agilent LC/MSD G1946D or an Agilent 1100 Series LC/MSD Trap G1311A. Quantifications were obtained on a Cary 50 Bio UV-visible spectrophotometer.

Nuclear magnetic resonance (NMR) spectra were obtained using a Varian INOVA (400 MHz) nuclear magnetic resonance spectrometer.

High performance liquid chromatography (HPLC) analytical separations were performed on an Agilent 1200 HPLC and followed by an Agilent Technologies G1315B Diode Array Detector with $UV_{max}$ @ 260 nm or 585 nm.

High performance liquid chromatography (HPLC) preparatory separations were performed on an Agilent 1100 HPLC G1361A and followed by an Agilent Technologies G1315B Diode Array Detector with $UV_{max}$ @ 260 nm or 585 nm.

Example 1
Preparation of Sinefungin Probe 1A, Sinefungin Probe 2A, and Sinefungin Probe 1B
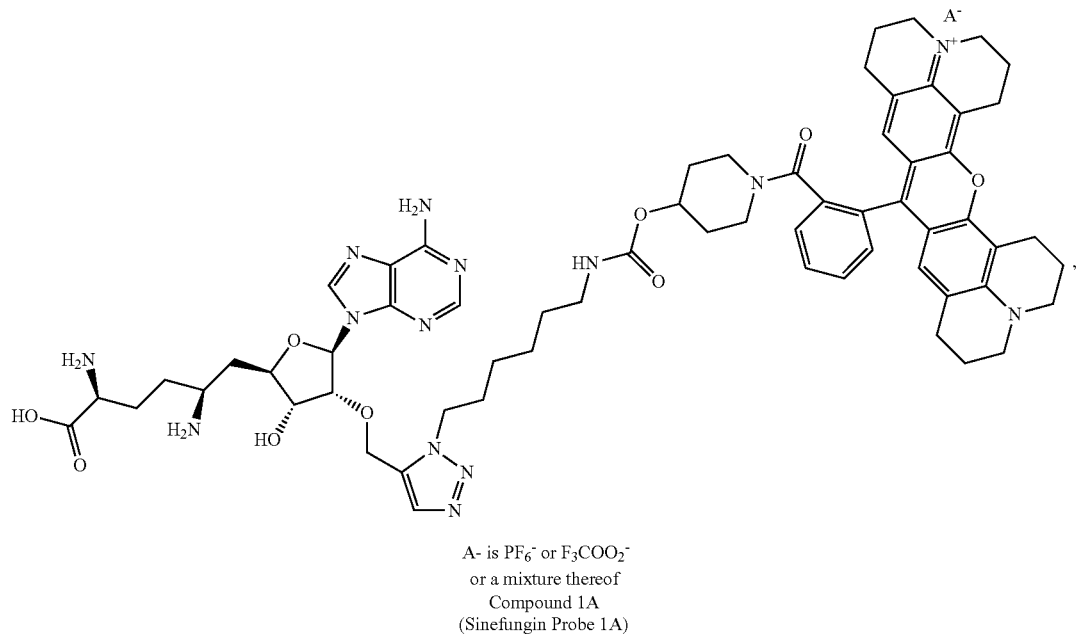
A- is PF$_6^-$ or F$_3$COO$_2^-$
or a mixture thereof
Compound 1A
(Sinefungin Probe 1A)
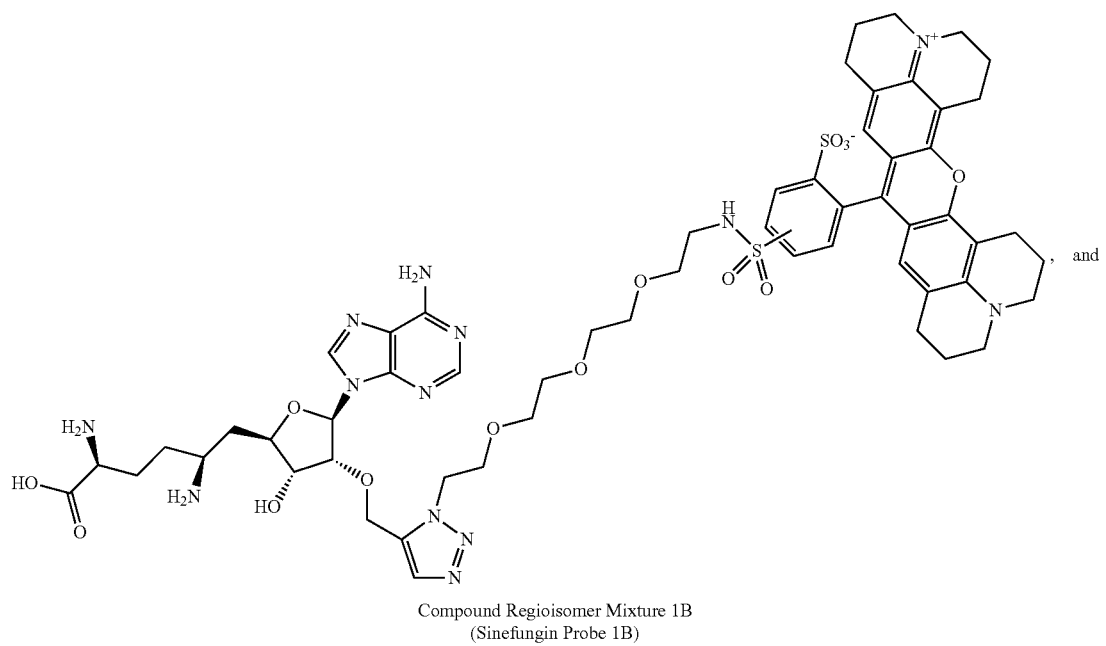
, and
Compound Regioisomer Mixture 1B
(Sinefungin Probe 1B)

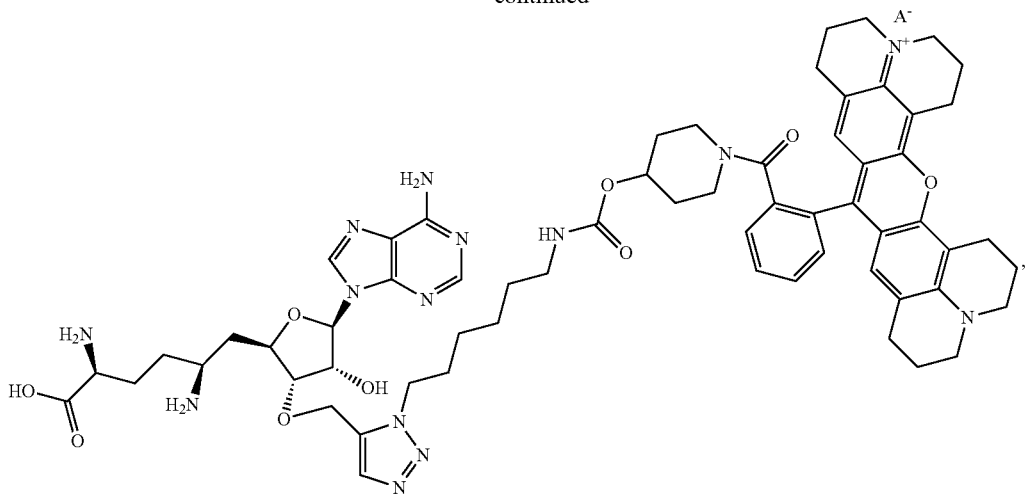

A- is PF$_6^-$ or F$_3$COO$_2^-$
or a mixture thereof
Compound 2A
(Sinefungin Probe 2A)

The synthetic route including the divergence at Step 3 upon separation of the regioisomers isolated in Step 2 is illustrated in FIG. 1.

Step 1: Preparation of (2S,5S)-6-(2R,3S,4R,5R)-5-(6-amino-9H-purin-9-yl)-3,4-dihydroxytetrahydrofuran-2-yl)-2,5-bis((tert-butoxycarbonyl)amino)hexanoic acid (Compound 4)

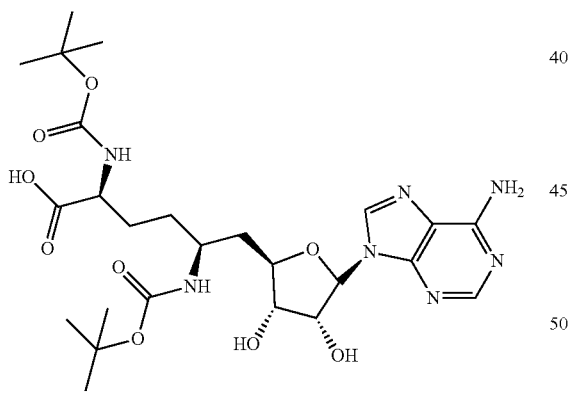

The title intermediate Compound 4 was prepared by reacting sinefungin (Compound 3, 5 mg, 0.013 mmol) in 1M NaOH (32 μL, 0.032 mmol) and water (268 μL) with di-tert-butyl dicarbonate (7 mg, 0.032 mmol) in 1,4-dioxane (300 μL). The reaction was stirred at room temperature overnight. LC/MS (Gemini C18, 3μ, 2.0×50 mm, 400 μL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) showed mostly desired intermediate (retention time 7.7 min, ESI$^+$ m/z 582, ESI$^-$ m/z 580) with a small amount of mono-protected intermediate (retention time 4.4 min, ESI$^-$ m/z 482, ESI$^-$ m/z 480). All solvent was removed, water was added and the pH was found to be about 8. 1M HCl was added to bring the pH to about 7. An extraction was done with ethyl acetate to remove impurities. Water was removed to give the title intermediate 4 (6 mg, 79% yield) as a white solid.

Step 2: Preparation and separation of a product mixture comprising (2S,5S)-6-((2R,3R,4R,5R)-5-(6-amino-9H-purin-9-yl)-3-hydroxy-4-(prop-2-yn-1-yloxy)tetrahydrofuran-2-yl)-2,5-bis((tert-butoxycarbonyl)amino)hexanoic acid (Compound 5) and (2S,5S)-6-((2R,3S,4R,5R)-5-(6-amino-9H-purin-9-yl)-4-hydroxy-3-(prop-2-yn-1-yloxy)tetrahydrofuran-2-yl)-2,5-bis((tert-butoxycarbonyl)amino) hexanoic acid (Compound 6)

Compound 5

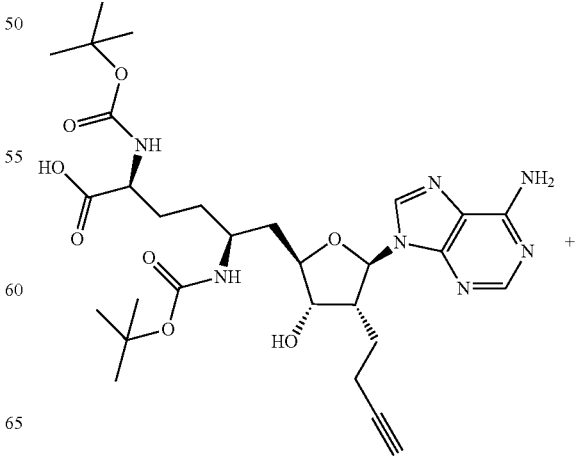

Compound 6

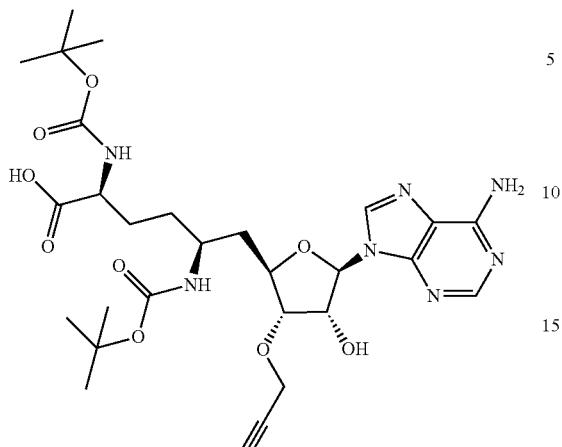

To a mixture consisting of (2S,5S)-6-((2R,3S,4R,5R)-5-(6-amino-9H-purin-9-yl)-3,4-dihydroxytetrahydrofuran-2-yl)-2,5-bis((tert-butoxycarbonyl)amino)hexanoic acid (Compound 4, 6 mg, 0.010 mmol) in 0.6 M KOH (83 μL, 0.050 mmol) was added 18-crown-6 (7 mg, 0.026 mmol) in 1,4-dioxane (83 μL) followed by propargyl bromide (80% in toluene, 2.2 μL, 0.020 mmol). The reaction mixture was stirred at room temperature overnight. HPLC (Gemini C18, 110 Å, 5μ, 250×4.6 mm, 1 mL/min, 5/95/0.05→50/50/0.05 ACN/H$_2$O/TFA) showed a mixture of mostly starting material (20.2 min, 35%), and two products possessing the mass of the desired mono-propargylated reaction product (21.9 min, 29%; 22.6 min, 6%) and undesired di-propargyl product (25.0 min, 14%). LC/MS (Gemini C18, 3μ, 2.0×50 mm, 400 μL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) confirmed the peak identities of starting Compound 4 (7.4 min, ESI$^+$ m/z 582), Compound 5/6 mixture (7.6 min, ESI$^+$ m/z 620), di-propargyl (7.9 min, ESI$^+$ m/z 658). Prep HPLC (Gemini C18, 110 Å, 10μ, 250×21.2 mm, 20 mL/min, 15/85/0.05→90/10/0.05 ACN/H$_2$O/TFA) was done to isolate the 4 aforementioned materials (starting material and three products). The major mono-propargyl product solution was concentrated to remove the ACN and then lyophilized to afford its purified isomer (Compound 5, 2 mg, 32% yield) as a white powder; LC/MS (same conditions as above) 7.5 min, ESI$^+$ m/z 620. The minor mono-propargyl product solution was concentrated to remove the ACN and then lyophilized to afford its purified isomer (Compound 6, <1 mg, <16% yield) as a white powder; LC/MS (same conditions as above) 7.0 min, ESI$^+$ m/z 620, ESI$^-$ m/z 618.

Step 3a: Preparation of (2S,5S)-2,5-diamino-6-((2R,3R,4R,5R)-5-(6-amino-9H-purin-9-yl)-3-hydroxy-4-(prop-2-yn-1-yloxy)tetrahydrofuran-2-yl)hexanoic acid (Compound 7)

Compound 7

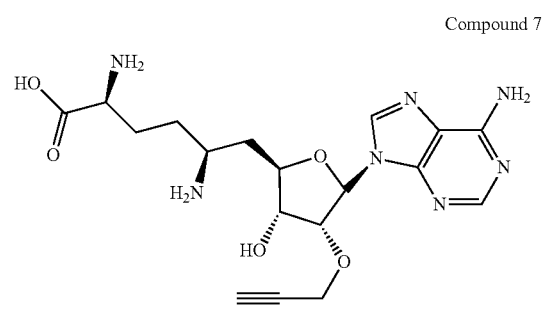

Compound 5 (1.0 mg, 0.0016 mmol) was deprotected using trifluoroacetic acid (TFA, 500 μL, 6.5 mmol) by stirring at room temperature for 30 min. The TFA was removed and the deprotected product was carried onto the next reaction step without further purification or characterization.

Step 3b: Preparation of (2S,5S)-2,5-diamino-6-((2R,3S,4R,5R)-5-(6-amino-9H-purin-9-yl)-4-hydroxy-3-(prop-2-yn-1-yloxy)tetrahydrofuran-2-yl)hexanoic acid (Compound 8)

Compound 8

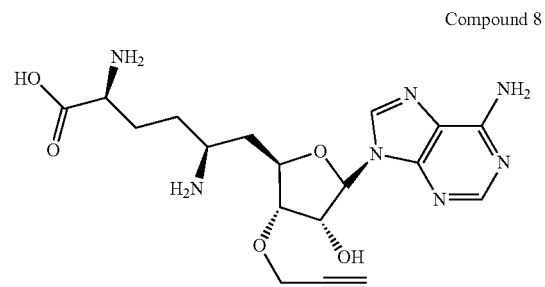

Compound 6 (<1.0 mg, <0.0016 mmol) was deprotected using trifluoroacetic acid (TFA, 500 μL, 6.5 mmol) by stifling at room temperature for 30 min. The TFA was removed and the deprotected product was carried onto the next reaction step without further purification or characterization.

Step 4a(i): Preparation of Sinefungin Probe 1A (Compound 1A)

To a mixture consisting of Compound 7 (~671 μg, 0.0016 mmol) in water (100 μL) with sodium ascorbate (1 mg, 0.005 mmol) in water (200 μL) was added copper(II) sulfate (500 μg, 0.0031 mmol) in water (100 μL) and CAL Fluor® Red 610 azide (Biosearch Technologies, Inc. Lot #MVR1716, 1.4 mg, 0.0016 mmol) in DMF (400 μL). The reaction mixture was stirred at room temperature overnight. HPLC (Gemini C18, 110 Å, 5μ, 250×4.6 mm, 1 mL/min, 5/95/0.05→90/10/0.05 ACN/H$_2$O/TFA) showed mainly one product (13.2 min, 21%) and starting fluorophore azide (19.6 min, 60%). Prep HPLC (Gemini C18, 110 Å, 10μ, 250×21.2 mm, 20 mL/min, 15/85/0.05→90/10/0.05 ACN/H$_2$O/TFA) was done to purify the product which eluted from the column at around 9 min. The product solution was concentrated to remove the ACN and then lyophilized to afford the title detection analyte compound (248 μg as quantified by UV (MeOH, extinction coefficient 91,000), 13% yield) as a dark purple solid; LC/MS (Gemini C18, 3μ, 2.0×50 mm, 400 μL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) consistent with that expected for pure title detection analyte compound (5.2 min, ESI$^+$ m/z=1162/2=581).

Step 4a(ii): Preparation of Sinefungin Probe 1B (Compound Regioisomer Mixture 1B)

To a mixture consisting of Compound 7 (~1 mg, 0.0016 mmol) in water (100 μL) with sodium ascorbate (1 mg, 0.005 mmol) in water (200 μL) was added copper(II) sulfate (500 μg, 0.0031 mmol) in water (100 μL) and Azide-Fluor585 (Click Chemistry Tools, Catalog #AZ110, 1.3 mg, 0.0016 mmol) in DMF (600 μL). The reaction mixture was stirred at room temperature overnight. HPLC (Gemini C18, 110 Å, 5μ, 250×4.6 mm, 1 mL/min, 5/95/0.05→90/10/0.05 ACN/H$_2$O/TFA) showed mainly one product mixture (12.3 min and 13 min, 40%) and starting fluorophore azide mixture (18.7 min and 20.5 min, 50%). The reaction mixture was allowed to continue stifling a second night. Prep HPLC (Gemini C18, 110 Å, 10μ, 250×21.2 mm, 20 mL/min, 15/85/0.05→90/10/0.05 ACN/H$_2$O/TFA) was done to purify the product which eluted from the column at around 8-9 min. The product solution was concentrated to remove the ACN and then lyophilized to afford the title detection analyte compound, which was taken up in methanol (500 μL) and quantified by UV (895 μg/mL, or 448 μg); LC/MS (Gemini C18, 3μ, 2.0×50 mm, 400 μL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) consistent with that expected for pure title detection analyte compound regioisomer mixture (5.4 min, ESI+ m/z=1226/2=613).

Step 4b: Preparation of Sinefungin Probe 2A (Compound 2A)

To a mixture consisting of Compound 8 (<671 μg, <0.0016 mmol) in water (100 μL) with sodium ascorbate (1 mg, 0.005 mmol) in water (200 μL) was added copper(II) sulfate (500 μg, 0.0031 mmol) in water (100 μL) and CAL Fluor® Red 610 azide (Biosearch Technologies, Inc. Lot #MVR1716, 1.4 mg, 0.0016 mmol) in DMF (400 μL). The reaction mixture was stirred at room temperature overnight. HPLC (Gemini C18, 110 Å, 5 Å, 250×4.6 mm, 1 mL/min, 5/95/0.05→90/10/0.05 ACN/H$_2$O/TFA) showed mainly one product (13.1 min, 3%) and starting fluorophore azide (19.4 min, 75%). Prep HPLC (Gemini C18, 110 Å, 10μ, 250×21.2 mm, 20 mL/min, 15/85/0.05→90/10/0.05 ACN/H$_2$O/TFA) was done to purify the product which eluted from the column at around 8.6 min. The product solution was concentrated to remove the ACN and then lyophilized to afford the title detection analyte compound (12 μg as quantified by UV (MeOH, extinction coefficient 91,000), ~0.6% yield) as a dark purple solid; LC/MS (Gemini C18, 3μ, 2.0×50 mm, 400 μL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) consistent with that expected for pure title detection analyte compound (5.1 min, ESI$^+$ m/z=1162/2=581).

Example 2

Preparation of Sinefungin Probe 3

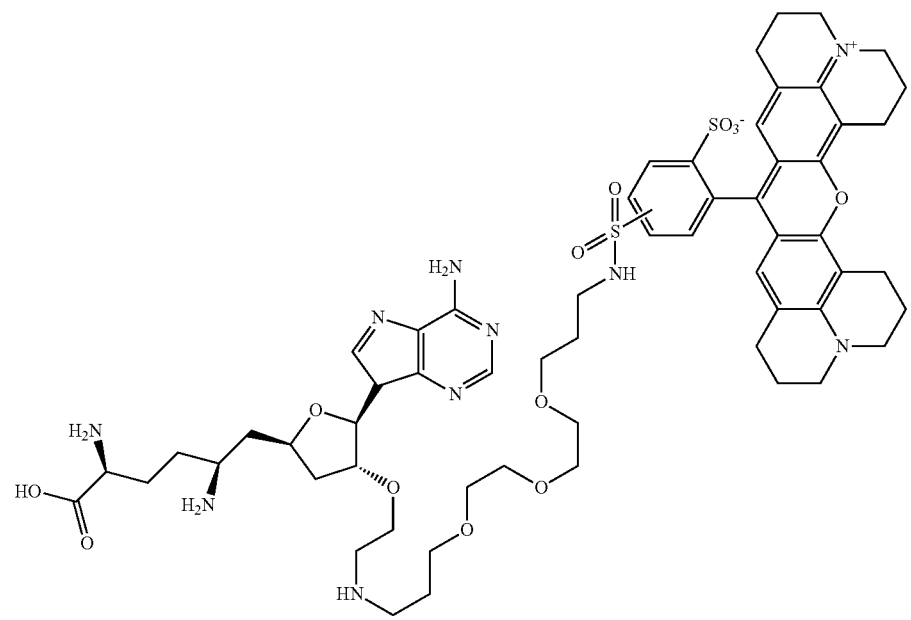

Compound Regioisomer Mixture 9
(Sinefungin Probe 3)

Step 1: Preparation of (2S,5S)-6-((2R,3R,4R,5R)-4-(allyloxy)-5-(6-amino-9H-purin-9-yl)-3-hydroxytetrahydrofuran-2-yl)-2,5-bis((tert-butoxycarbonyl)amino)hexanoic acid (Compound 10)

Compound 10

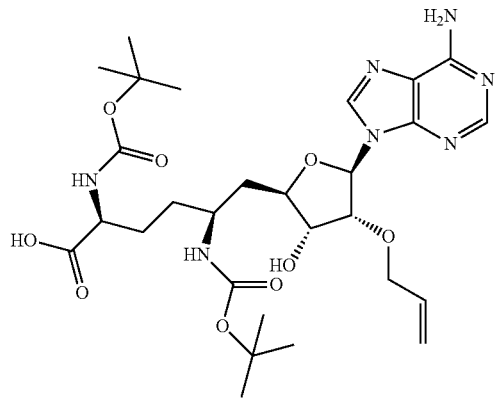

To a mixture consisting of (2S,5S)-6-((2R,3S,4R,5R)-5-(6-amino-9H-purin-9-yl)-3,4-dihydroxytetrahydrofuran-2-yl)-2,5-bis((tert-butoxycarbonyl)amino)hexanoic acid (Compound 4, 5 mg, 0.0086 mmol) in 0.6 M KOH (72 µL, 0.043 mmol) was added 18-crown-6 (9 mg, 0.034 mmol) in 1,4-dioxane (72 µL) followed by allyl bromide (1.7 µL, 0.020 mmol). The reaction mixture was stirred at room temperature over the weekend. HPLC (Gemini C18, 110 Å, 5µ, 250×4.6 mm, 1 mL/min, 5/95/0.05→50/50/0.05 ACN/H$_2$O/TFA) showed a mixture of mostly starting material (19.7 min, 45%), and two products possessing the mass of the desired mono-allylated reaction product (21.9 min, 34%; 22.6 min, 9%) and undesired di-allyl product (25.6 min, 7%). The desired (major) mono-allyl ether product was isolated by prep HPLC (Gemini C18, 110 Å, 10µ, 250×21.2 mm, 20 mL/min, 5/95/0.05→50/50/0.05 ACN/H$_2$O/TFA)—peak collected at about 13.5 min. The major mono-allyl ether product solution was concentrated to afford the title intermediate (Compound 10, 2.3 mg, 43% yield) as a colorless solid; LC/MS (Gemini C18, 3µ, 2.0×50 mm, 400 µL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) 6.2 min, ESI$^+$ m/z 622, ESI$^-$ m/z 620.

Step 2: Preparation of (2S,5S)-6-((2R,3R,4R,5R)-5-(6-amino-9H-purin-9-yl)-3-hydroxy-4-(2-oxoethoxy)tetrahydrofuran-2-yl)-2,5-bis((tert-butoxycarbonyl)amino)hexanoic acid (Compound 11)

Compound 11

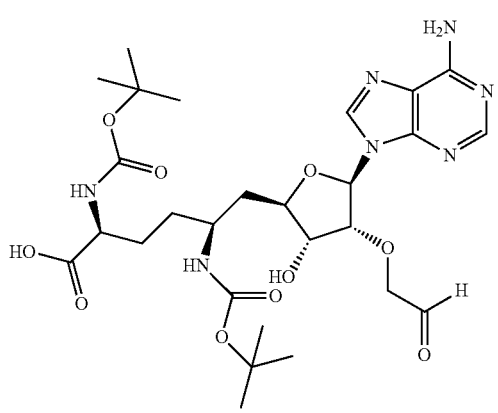

To a 7-mL scintillation vial containing Compound 10 (2.0 mg, 0.0032 mmol) was added sequentially tetrahydrofuran (200 µL), water (132 µL), sodium periodate (3.3 mg, 0.015 mmol), and a mixture consisting of potassium osmium tetroxide dihydrate (68 µg, 0.00018 mmol) and water (68 µL). The reaction mixture was stirred overnight in the dark at room temperature. HPLC (Gemini C18, 110 Å, 5µ, 250×4.6 mm, 1 mL/min, 5/95/0.05→50/50/0.05 ACN/H$_2$O/TFA) showed complete disappearance of starting material. The reaction mixture was placed in the freezer overnight and the desired product isolated the following day by prep HPLC (Gemini C18, 110 Å, 10µ, 250×21.2 mm, 20 mL/min, 5/95/0.05→50/50/0.05 ACN/H$_2$O/TFA)—split peak collected at about 20.5 min. The relevant fractions were combined and concentrated to afford the title intermediate (1 mg, 50% yield) as a clear solid; LC/MS ESI$^+$ m/z 624, ESI$^-$ m/z 622.

Step 3: Preparation of bis-BOC-protected sinefungin-2'-O-(amine-PEG$_3$-aminosulfonyl linker)-Fluor585 (Compound Regioisomer Mixture 12)

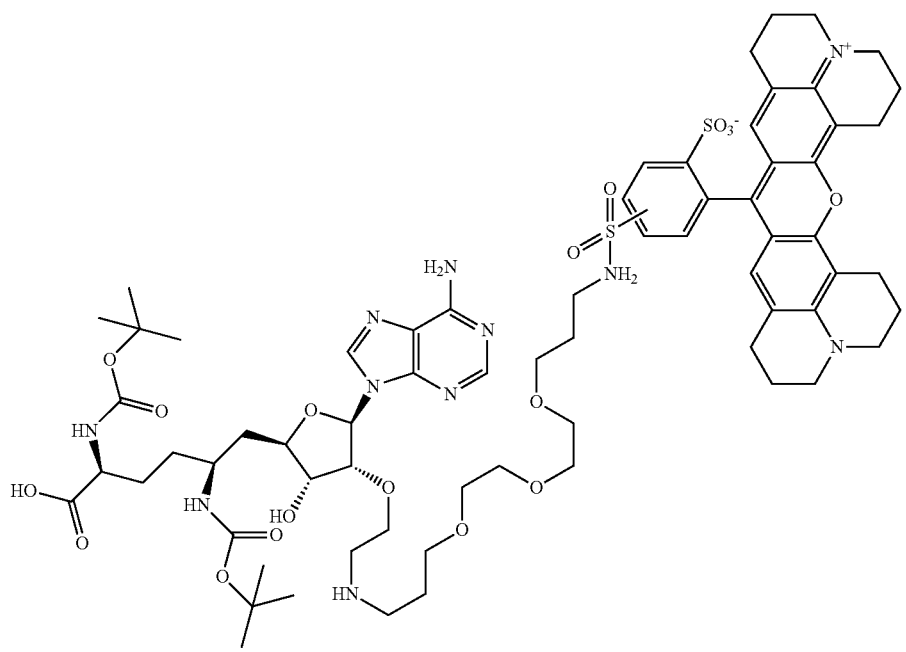

Compound Regioisomer Mixture 12

To a 7-mL scintillation vial containing Compound 11 (500 µg, 0.00080 mmol) was added a mixture consisting of Sulforhodamine 101-PEG$_3$-amine (Biotium, 675 µg, 0.00084 mmol) and methanol (135 µL). The reaction mixture was stirred in the dark at room temperature for 4.5 hours. HPLC (Gemini C18, 110 Å, 5µ, 250×4.6 mm, 1 mL/min, 5/95/0.05→90/10/0.05 ACN/H$_2$O/TFA) showed only starting materials present. The reaction mixture was subsequently treated with a mixture consisting of sodium cyanoborohydride (1 mg, 0.016 mmol) in pH 5.5 sodium acetate buffer (50 µL) followed by additional buffer rinse (50 µL). The reaction mixture was stirred in the dark at room temperature overnight. Analysis by HPLC (same method as above) showed a product peak. Prep HPLC (Gemini C18, 110 Å, 10µ, 250×21.2 mm, 20 mL/min, 30/70/0.05→90/10/0.05 ACN/H$_2$O/TFA) resulted the collection of two products, one eluting at about 8 minutes, and another at about 9 minutes. The combined products were concentrated and lyophilized to afford the title intermediate (<1 mg); LC/MS ESI$^+$ m/z=1416/2=708).

Step 4: Preparation of Sinefungin Probe 3 (Compound Regioisomer Mixture 9)

To an ice-chilled 2-mL amber vial containing Compound Regioisomer Mixture 12 (<1 mg) was added a mixture consisting of 1:1 v/v trifluoroacetic acid-dichloromethane (50 µL). The reaction mixture was allowed to stand cold for five minutes and was subsequently concentrated by blowing off the solvent mixture with a nitrogen stream. The concentrate was taken up into methanol and was purified by prep HPLC (Gemini C18, 110 Å, 10µ, 250×21.2 mm, 20 mL/min, 5/95/0.05→90/10/0.05 ACN/H$_2$O/TFA over 20 min). The two major (product regioisomers—LC/MS ESI$^+$ m/z 608 for both peaks) peaks were collected, concentrated, and lyophilized to afford the title compound (138 µg—quantified by UV in methanol using 80,000 extinction coefficient) as a dark purple solid.

Example 3

Preparation of Sinefungin Probe 4 (Compound 13)

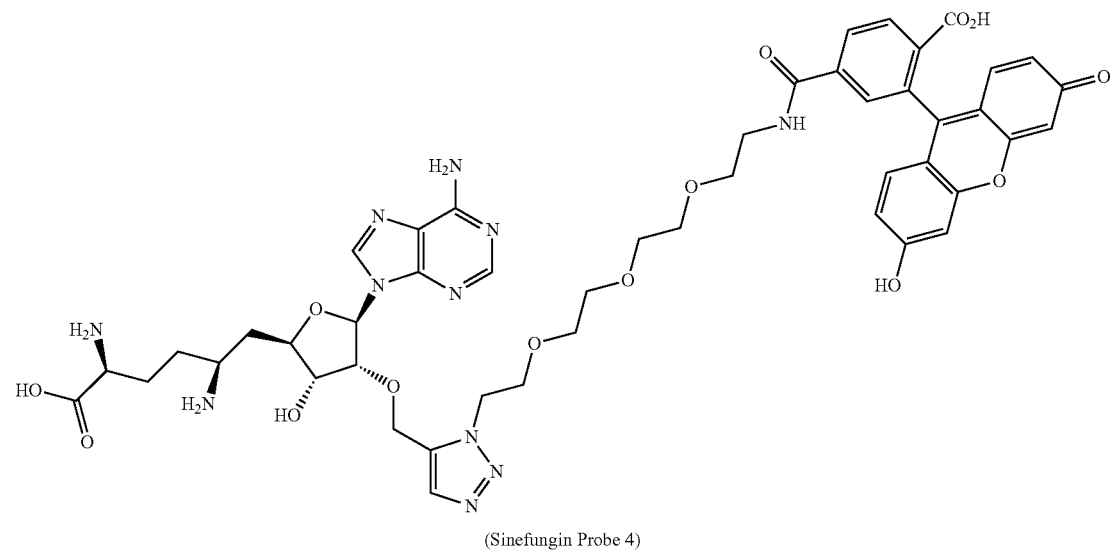

(Sinefungin Probe 4)

The title detection analyte compound was prepared from Compound 7 (Example 1, Step 3a) by coupling with 6-carboxyfluorescein-PEG$_3$ azide (Berry & Associates, CAS #412319-45-0, Catalog No. FF6110) using the click chemistry methods reported herein; LC/MS (Gemini C18, 3μ, 2.0× 50 mm, 400 μL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) 4.3 min (100% purity), ESI$^+$ m/z 498 (z=2; expected molecular mass: 996).

Example 4

Preparation of Thioadenosine Probe 1

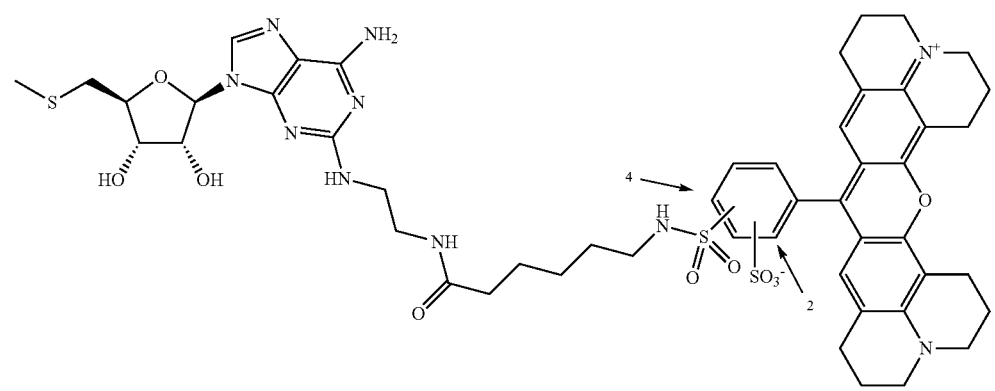

Thioadenosine Probe 1

Route 1

Step 1: Preparation of (2R,3R,4S,5S)-2-(6-amino-2-chloro-9H-purin-9-yl)-5-(chloromethyl)tetrahydrofuran-3,4-diol, also called 5'-deoxy-5'-(chloro)-2-chloroadenosine (Compound 14)

Compound 14

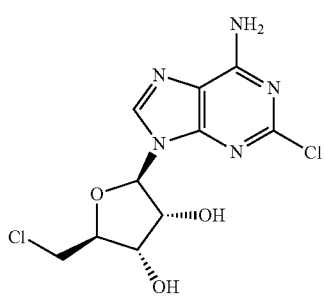

To a flask containing hexamethylphosphoramide (10 mL) was added thionyl chloride (1.5 mL, 2.4 g, 21 mmol) at 0° C. with stifling. The solution was allowed to reach room temperature before 2-chloroadenosine (Toronto Research Chemicals, 1.0 g, 3.3 mmol) was added portionwise. The orange suspension was stirred under nitrogen at room temperature overnight. The mixture was poured into water (90 mL) and the resulting mixture was subsequently filtered. The yellow solids were washed with water then stirred in 1N NH$_4$OH (50 mL) for two hours. The mixture was filtered then washed with cold water. The white solid was dried under high vacuum to obtain the title intermediate (0.80 g, 76% yield); $^1$H NMR (400 MHz, DMSO-d$_6$) δ 3.83 (dd, 1 H), 3.91 (dd, 1 H), 4.07 (dd, 1 H), 4.16 (dd, 1 H), 4.65 (dd, 1 H), 5.46 (d, 1 H), 5.60 (d, 1 H), 5.84 (d, 1 H), 7.84 (br s, 2 H), 8.35 (s, 1 H); MS (ESI$^+$): m/z 291, 293 (M+1).

Step 2: Preparation of (2R,3R,4S,5S)-2-(6-amino-2-chloro-9H-purin-9-yl)-5-((methylthio)methyl)tetrahydrofuran-3,4-diol, also called 5'-deoxy-5'-(methylthio)-2-chloroadenosine (Compound 15A)

Compound 15A

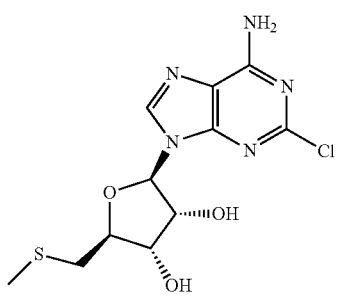

Compound 14 (320 mg, 1.0 mmol) was stirred under nitrogen in DMF (3 mL) at 0° C. Sodium methanethiolate (77 mg, 1.1 mmol) was added portionwise and the mixture allowed to reach room temperature with stifling overnight. The mixture was poured into saturated aqueous NaCl (30 mL). The pH of the solution was adjusted to ~7 with 6N HCl. The solution was diluted with more saturated NaCl to precipitate a gummy solid. The aqueous portion was decanted and the remaining solid purified by silica chromatography (2 to 10% methanol in chloroform). Appropriate fractions were collected, solvent removed and the title intermediate obtained as a white solid (0.80 g, 36% yield); MS (ESI$^+$): m/z 332.0, 334.0 (M+1) and (ESI$^−$): m/z 330.0 (M−1).

Step 3: Preparation of tert-butyl (2-((6-amino-9-((2R,3R,4S,5S)-3,4-dihydroxy-5-((methylthio)methyl)tetrahydrofuran-2-yl)-9H-purin-2-yl)amino)ethyl)carbamate, also called 5'-deoxy-5'-(methylthio)-2-(ethylamino-tert-butylcarbamate)-adenosine (Compound 16A)

Compound 16A

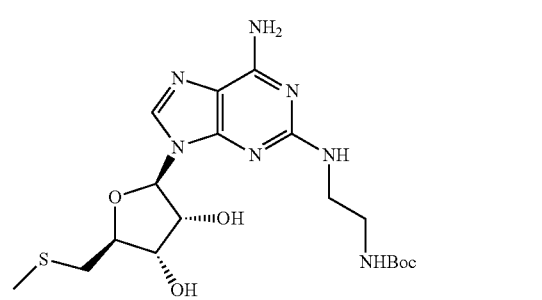

To a microwave tube containing compound 15A (120 mg, 0.36 mmol) was added tert-butyl N-(2-aminoethyl)carbamate (580 mg, 3.62 mmol). The mixture was heated in a microwave for 20 min. at 120° C. under nitrogen. After cooling to room temperature the mixture was dissolved in dichloromethane and the crude reaction mixture was loaded on a 12 g Silicycle column. The residue was then purified by silica chromatography (0 to 11% 2 to 10% methanol in dichloromethane). Appropriate fractions were collected, solvent removed and the title intermediate obtained as a white solid (0.017 g, 11% yield); MS (ESI$^+$): m/z 456.1 (M+1), 478.0 (M+Na).

Step 4: Preparation of Thioadenosine Probe 1 (Compound 17A)

Deprotection of Compound 16A to Produce Boc-Deprotected Compound 16A Trifluoroacetate Salt: Compound 16A (11 mg, 0.024 mmol) was treated with an excess of trifluoroacetic acid (500 μL, 6.5 mmol) at room temperature in a 7-mL scintillation vial. The resulting cloudy mixture was clarified partially by the addition of a few drops of methanol followed by a few drops of dichloromethane, and the reaction was allowed to carry on for 30 minutes. The solvent was subsequently blown off and the 5'-deoxy-5'-(methylthio)-2-(1,2-diaminoethyl-1-yl)-adenosine residue taken up into dichloromethane with a slight methanol additive to aid in dissolution, and the mixture analyzed by thin layer chromatography (TLC) and LCMS. TLC: 10:90:0.5 v/v methanol-dichloromethane-conc. NH$_4$OH, no starting material present, product spot R$_f$=0; LCMS (ESI+) m/z 356 (M+1). Analysis by HPLC (gradient: 5:95:0.05 to 90:10:0.05 acetonitrile-water-TFA) showed the product comprised two major entities: 5.8 min (21%), 6.1 min (70%).

Conjugation of Boc-deprotected Compound 16A trifluoroacetate salt with Texas Red-X, succinimidyl ester (Life Technologies Catalog #T-6134) to produce Thioadenosine Probe 1: The Boc-deprotected Compound 16A trifluoroacetate salt (500 µg, 0.00086 mmol) was dissolved in DMF in a 2-mL amber vial, to which diisopropylethylamine (50 µL, 0.24 mmol) was added followed by the Texas Red-X, succinimidyl ester (Invitrogen) solution (1.5 mg in 100 µL DMF) and 2×50 µL DMF rinses. The reaction mixture was stirred overnight. The crude product was purified by prep HPLC (5:95:0.05 to 90:10:0.05 acetonitrile-water-TFA afforded separation of the desired material as shown by a major peak elution at 12.5 minutes. The purest fraction was concentrated and the residue taken up in methanol for quantification after the usual manner. The methanol solution (0.78 mL) concentration was measured and calculated to be 184 µg/mL, affording the purified Thioadenosine Probe 1 (free form) with 15.8% yield; HPLC-UV purity: 96.9%; LCMS (ESI$^+$) m/z 1057.

Route 2

Step 1: Preparation of tert-butyl (2-((6-amino-9-((2R,3R,4S,5R)-3,4-dihydroxy-5-(hydroxymethyl)tetrahydrofuran-2-yl)-9H-purin-2-yl)amino)ethyl)carbamate (Compound 18)

Compound 18

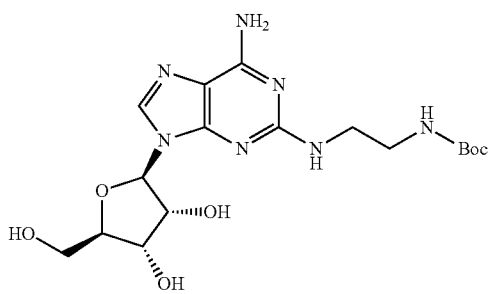

A NEAT mixture of 2-chloroadenosine (1.15 g, 8.81 mmol) and tert-butyl N-(2-aminoethyl)carbamate (3.2 g, 20 mmol) under a nitrogen stream in a 250-mL round bottom flask was heated to 150° C. for two hours, over which time turned the mixture to a red oil. The mixture was subsequently cooled to room temperature and was treated with 9:1 v/v dichloromethane-methanol (about 60 mL) with stifling, generating an orange precipitate. The precipitate was collected by filtration and dried to afford the title intermediate (1.48 g, 91.4% yield) as a white solid; TLC R$_f$ (9:1 v/v dichloromethane-methanol) 0.26; LC/MS (ESI+) m/z 426.

Step 2: Preparation of tert-butyl (2-((6-amino-9-((2R,3R,4S,5S)-5-(chloromethyl)-3,4-dihydroxytetrahydrofuran-2-yl)-9H-purin-2-yl)amino)ethyl)carbamate (Compound 19)

Compound 19

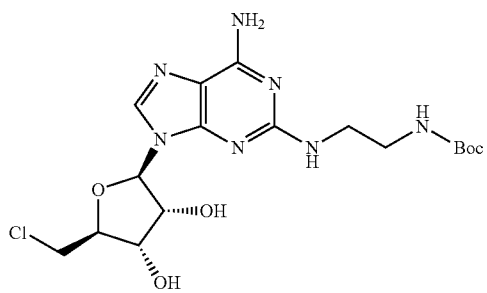

To a stifling mixture consisting of Compound 18 (1.03 g, 2.42 mmol) and acetonitrile (80 mL) under a nitrogen atmosphere and cooled over an ice-acetone bath was added thionyl chloride (0.53 mL, 7.3 mmol). The reaction mixture continued stirring cold for 15 minutes and was subsequently treated with pyridine (0.469 g, 4.84 mmol) with dropwise addition. An immediate color change was observed, and the mixture was stirred cold for another 45 minutes. The cold bath was removed and the mixture was allowed to stir overnight at room temperature. The reaction mixture was concentrated under reduced pressure, and the residue was dissolved in methanol. The ice bath-cooled mixture under a nitrogen atmosphere was treated with ammonium hydroxide solution to pH 10. The resulting mixture was stirred for 1.5 hours, as it was allowed to warm to room temperature. The mixture was concentrated under reduced pressure, and the residue was purified by silica column (80 g) chromatography. Elution with a gradient (100% dichloromethane to 10% methanol in dichloromethane), combination of fractions containing separated desired product, and concentration under reduced pressure afforded the title intermediate (0.175 g, 16.4% yield) as a white solid; $^1$H NMR (400 MHz, DMSO-d$_6$) δ 7.87 (s, 1 H), 6.81 (t, 1H, J=5.5 Hz), 6.73 (s, 2H), 6.26 (t, 1H, J=5.5 Hz), 5.73 (d, 1H, J=5.5 Hz), 5.47 (d, 1H, J=5.9 Hz), 5.36 (d, 1H, J=5.1 Hz), 4.75 (broad m, 1 H), 4.20 (m, 1H), 4.01 (m, 1H), 3.90 (dd, 1H, 11.4, 5.2 Hz), 3.79 (m, 1H), 3.23 (m, 2H), 3.08 (m, 2H), 2.06 (s, 2H), 1.34 (s, 9H); LC/MS (ESI+) m/z 444.

Step 3: Preparation of Compound 16A

Compound 19 (limiting reagent) is stirred under nitrogen in DMF at 0° C. Sodium methanethiolate (1.1 molar equivalent) is added portionwise and the mixture allowed to reach room temperature with stirring overnight. The reaction mixture is worked up and the product purified and isolated in a manner similar to that described for Compound 15A, Route 1, Step 2 above.

Step 4: Preparation of Thioadenosine Probe 1 (Compound 17A)

The title detection analyte is prepared from Compound 16A according to the manner described in Route 1, Step 4 above.

Example 5

Preparation of Aza-Adenosine Probes 1 and 2

(Compound 22A-iii)

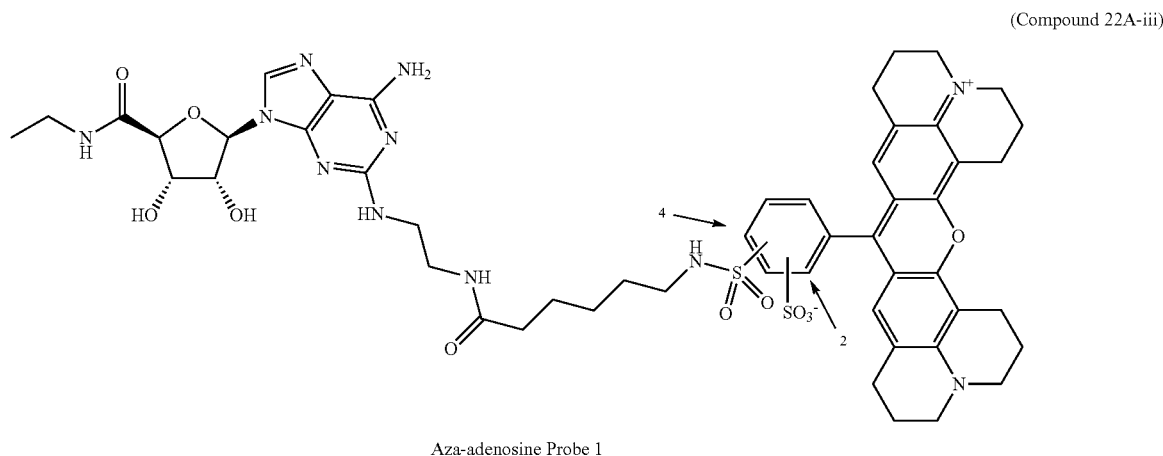

Aza-adenosine Probe 1

(Compound 22A-iv)

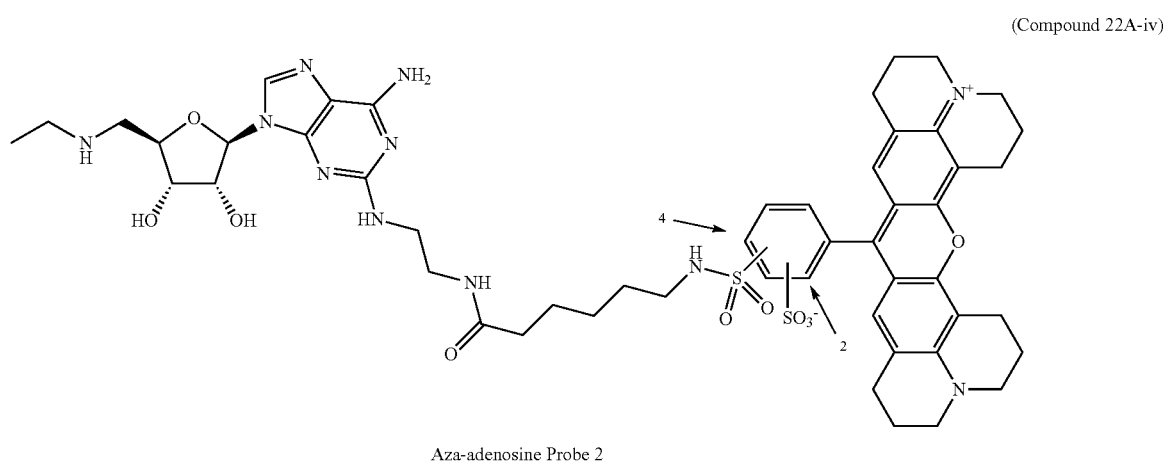

Aza-adenosine Probe 2

A. Preparation of Aza-adenosine Probe 1

Step 1: Preparation of 2-chloroadenosine-5'-N-ethylcarboxamide (Compound 20A-iii)

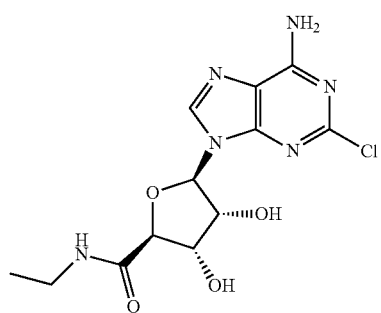 [SMILES: CCNC(=O)[C@H]1O[C@@H](n2cnc3c(N)nc(Cl)nc32)[C@H](O)[C@@H]1O]

To a mixture consisting of 2-chloro-2',3'-O-isopropylideneadenosine-5'-N-ethylcarboxamide (CAS #120225-75-4, Toronto Research Chemicals, Catalog #C367370, 2 mg, 0.0052 mmol) in methanol (250 μL) was added 0.1M HCl (250 μL). The reaction was stirred at room temperature overnight. TLC (5:95 MeOH:$CH_2Cl_2$) still showed starting material. The reaction was heated to 50° C. and allowed to react overnight. TLC showed the starting material was gone. Upon cooling to room temperature, white solid precipitated. Water was added to rinse away excess acid followed by a second rinse checking to make sure the water was neutral. The product was a white solid (1.2 mg, 60% yield as the HCl salt). HPLC (Gemini C18, 110 Å, 5μ, 250×4.6 mm, 1 mL/min, 5/95/0.05→50/50/0.05 ACN/$H_2O$/TFA) showed the purity to be ≥99%. LC/MS (Gemini C18, 3μ, 2.0×50 mm, 400 μL/min, A: 90/10/0.01 $H_2O$/MeOH/HOAc, B 90/10/0.01 MeOH/$H_2O$/HOAc 0-6 min 0-100% B, 6-9 hold at 100% B, 9.1-15 min re-equilibrate at 0% B) confirmed the peak identity as product (6.3 min, ESI$^+$ m/z 343, ESI$^-$ m/z 342).

Step 2: Preparation of tert-butyl (2-((6-amino-9-((2R,3R,4S,5S)-5-(ethylcarbamoyl)-3,4-dihydroxytetrahydrofuran-2-yl)-9H-purin-2-yl)amino)ethyl)carbamate (Compound 21A-iii)

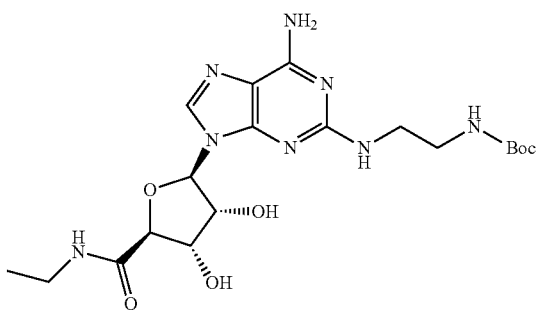 [SMILES: CCNC(=O)[C@H]1O[C@@H](n2cnc3c(N)nc(NCCNC(=O)OC(C)(C)C)nc32)[C@H](O)[C@@H]1O]

To a microwave tube containing Compound 20A-iii is added tert-butyl N-(2-aminoethyl)carbamate (10-fold molar excess). The mixture is heated in a microwave for 20 min. at 120° C. under nitrogen. Workup of the reaction mixture, purification, and isolation of the title intermediate is carried out in a manner similar to that of Example 4, ROUTE 1, Step 3 used for Compound 16A.

Step 3: Preparation of Aza-adenosine Probe 1 (Compound 22A-iii)

Boc-deprotection of Compound 21A-iii and subsequent conjugation with Texas Red-X, succinimidyl ester is carried out in a manner similar to that of Example 4, ROUTE 1, Step 4 for Compound 17A (Thioadenosine Probe 1).

B. Preparation of Aza-adenosine Probe 2

Step 1: Preparation of 2-chloro-2',3'-O-isopropylideneadenosine-5'-N-ethylamine (Compound 20A-ii)

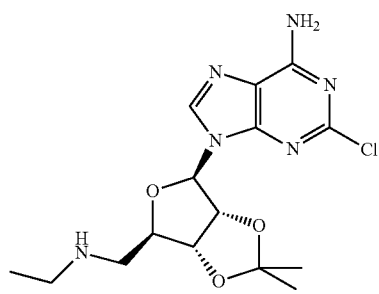 [SMILES: CCNC[C@H]1O[C@@H](n2cnc3c(N)nc(Cl)nc32)[C@@H]2OC(C)(C)O[C@@H]21]

To a mixture consisting of 2-chloro-2',3'-O-isopropylideneadenosine-5'-N-ethylcarboxamide (2 mg, 0.0052 mmol) in THF (400 µL) cooled to 0° C. was added borane dimethyl sulfide complex (2 M in THF, 50 µL, 0.1 mmol). The reaction was allowed to slowly warm to room temperature overnight. The reaction was worked up by cooling it in an ice bath and adding methanol (1 mL) and stirred for one hour. The reaction mixture was concentrated, cooled to 0° C. followed by addition of methanolic HCl (8 µL acetyl chloride, 2 mL MeOH). The reaction was stirred and allowed to come to room temperature over two hours. The reaction mixture was concentrated and then triturated with ether to give an off-white solid (2.3 mg, quantitative crude yield). HPLC (Gemini C18, 110 Å, 5µ, 250×4.6 mm, 1 mL/min, 5/95/0.05→50/50/0.05 ACN/H$_2$O/TFA) showed starting material was mostly gone and 3 new peaks (6 min, 34%; 8.1 min, 12%; 9 min, 21%). LC/MS (Gemini C18, 3µ, 2.0×50 mm, 400 µL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) confirmed the presence of product (0.5 min, 4.2 min ESI$^+$ m/z 369).

Step 2: Preparation of 2-chloroadenosine-5'-N-ethylamine (Compound 20A-iv)

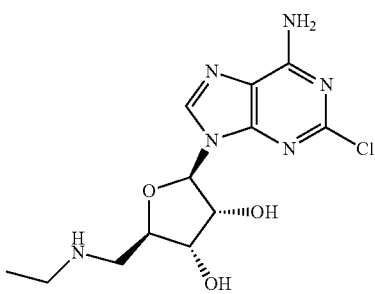 [SMILES: CCNC[C@H]1O[C@@H](n2cnc3c(N)nc(Cl)nc32)[C@H](O)[C@@H]1O]

To a mixture consisting of Compound 20A-ii (400 µg, 0.0011 mmol) in methanol (200 µL) was added 0.1 M HCl (200 µL). The reaction was heated to 50° C. and allowed to proceed overnight. TLC showed the starting material was gone. HPLC (Gemini C18, 110 Å, 5µ, 250×4.6 mm, 1 mL/min, 5/95/0.05→90/10/0.05 ACN/H$_2$O/TFA) showed mostly one peak (6.1 min, 72%). Prep HPLC (Gemini C18, 110 Å, 10µ, 250×21.2 mm, 20 mL/min, 5/95/0.05→50/50/0.05 ACN/H$_2$O/TFA) was done to isolate the product peak. Evaporation of solvents yielded the product as a white solid (400 µg, 66% yield as the TFA salt). LC/MS (Gemini C18, 3µ, 2.0×50 mm, 400 µL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) confirmed the peak identity as product (ESI$^+$ m/z 329).

Aza-adenosine Probe 2 is prepared from Compound 20A-iv in a manner similar to that described in Steps 2 and 3 used for preparation of Aza-adenine Probe 1.

Example 6

Preparation of Aza-Adenosine Probes 3 and 4

(Compound 22B-iii)

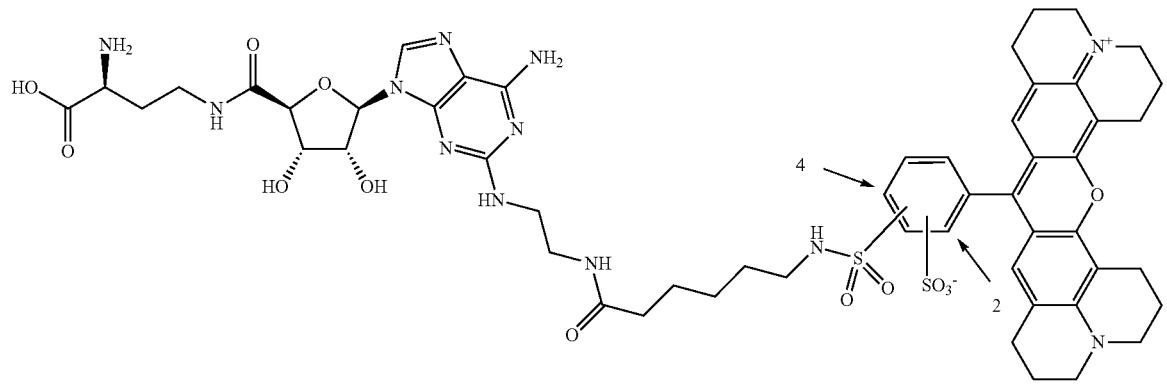

Aza-adenosine Probe 3

(Compound 22B-iv)

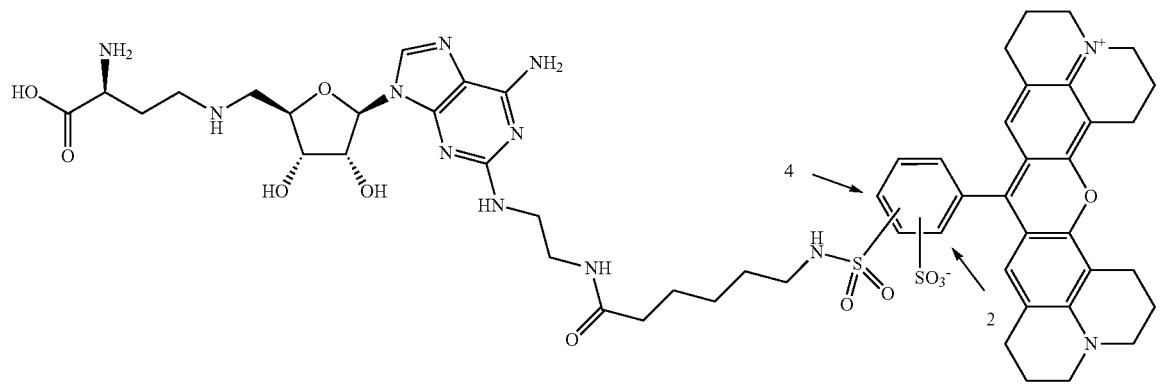

Aza-adenosine Probe 4

A. Preparation of Aza-Adenosine Probe 3

Step 1: Preparation of 2-chloro-2',3'-O-isopropylideneadenosine-5'-N-Boc-ornithineamide t-butyl ester (Compound 20B-i)

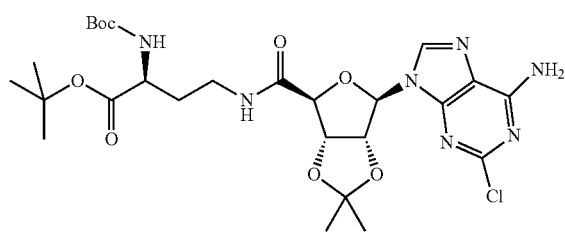 [SMILES: CC(C)(C)OC(=O)N[C@@H](CCNC(=O)[C@H]1O[C@@H](n2cnc3c(N)nc(Cl)nc32)[C@@H]2OC(C)(C)O[C@@H]21)C(=O)OC(C)(C)C]

2-Chloroadenosine-5'-carboxy-2',3'-O-isopropylidene (CAS #72209-19-9, 10 mg, 0.028 mmol), Boc-L-Dab-OtBu hydrochloride (17 mg, 0.055 mmol), N-(3-dimethylaminopropyl)-N'-ethylcarbodiimide hydrochloride (11 mg, 0.057 mmol) and N,N-diisopropylethylamine (10 µL, 0.057 mmol) were combined in DMF (300 µL). The reaction was allowed to proceed overnight at room temperature. HPLC (Gemini C18, 110 Å, 5µ, 250×4.6 mm, 1 mL/min, 5/95/0.05→90/10/0.05 ACN/H$_2$O/TFA) showed 3 new peaks (9.9 min, 24%; 10.1 min, 16%; 17.3, 52%). Prep HPLC (Gemini C18, 110 Å, 10µ, 250×21.2 mm, 20 mL/min, 5/95/0.05→50/50/0.05 ACN/H$_2$O/TFA) was done to isolate the 2 pks close to 10 min together and the 17.3 min pk. LC/MS (Gemini C18, 3µ, 2.0×50 mm, 400 µL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) showed the 2 earlier pks were EDC adducts of the starting materials and confirmed the latter pk as product (ESI$^+$ m/z 612). The product solution was concentrated to give the title intermediate (10 mg, 59% yield) as a white solid.

Step 2: Preparation of 2-chloroadenosine-5'-N-ornithineamide (Compound 20C-iii)

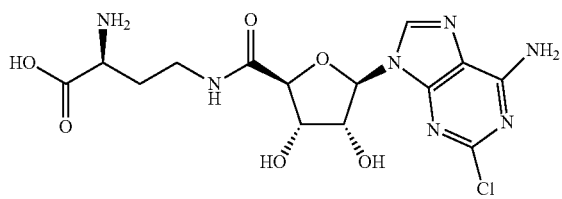 [SMILES: Nc1nc(Cl)nc2c1ncn2[C@@H]1O[C@H](C(=O)NCC[C@H](N)C(=O)O)[C@@H](O)[C@H]1O]

To Compound 20B-i (2 mg, 0.0033 mmol) was added 3 M HCl (500 µL, 1.5 mmol) and a few drops methanol for solubility. The reaction mixture was stirred at room temperature overnight. TLC (5:95 MeOH:CH$_2$Cl$_2$) showed that starting material was gone and that a new baseline spot had appeared. HPLC (Gemini C18, 110 Å, 5µ, 250×4.6 mm, 1 mL/min, 5/95/0.05→90/10/0.05 ACN/H$_2$O/TFA) showed mostly one new peak (6.5 min, 78%). LC/MS (Gemini C18, 3µ, 2.0×50 mm, 400 µL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) confirmed the peak identity as product (ESI$^+$ m/z 416).

Aza-adenosine Probe 3 is prepared from Compound 20A-iv in a manner similar to that described in Steps 2 and 3 used for preparation of Aza-adenine Probe 1.

B. Preparation of Aza-Adenosine Probe 4

Step 1: Preparation of 2-chloro-2',3'-O-isopropylideneadenosine-5'-N-Boc-ornithineamine t-butyl ester (Compound 20B-ii)

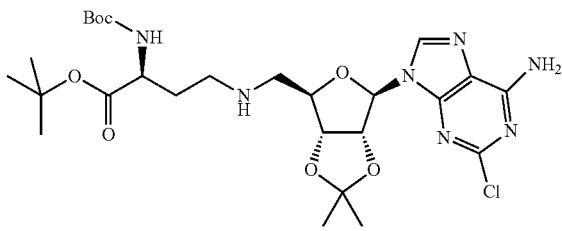 [SMILES: CC(C)(C)OC(=O)N[C@@H](CCNC[C@H]1O[C@@H](n2cnc3c(N)nc(Cl)nc32)[C@@H]2OC(C)(C)O[C@@H]21)C(=O)OC(C)(C)C]

Following a procedure similar to that described in Example 5 (Aza-adenosine Probe 2, Step 1), borane dimethyl sulfide complex (2 M in THF, 30 µL, 0.1 mmol) was added to a 0° C. solution of Compound 20B-i (2 mg, 0.0033 mmol) in THF (400 µL). The reaction mixture was allowed to slowly warm to room temperature overnight. The same work up was done to afford the crude title intermediate (1.6 mg, 80% yield) as a white solid. HPLC (Gemini C18, 110 Å, 5µ, 250×4.6 mm, 1 mL/min, 5/95/0.05→90/10/0.05 ACN/H$_2$O/TFA) showed some starting material and other peaks. LC/MS (Gemini C18, 3µ, 2.0×50 mm, 400 µL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) confirmed the presence of product (ESI$^+$ m/z 598).

Step 2: Preparation of 2-chloroadenosine-5'-N-ornithineamine (Compound 20C-iv)

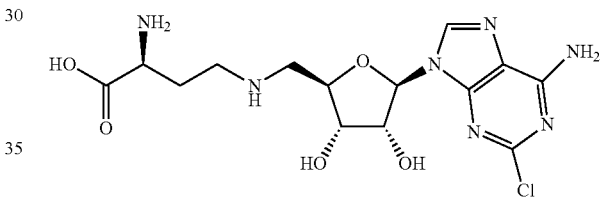

A mixture consisting of Compound 20B-ii (1.6 mg, 0.0027 mmol) and methanol (100 µL) was treated with 3 M HCl (300 µL). The reaction mixture was stirred at room temperature overnight. HPLC (Gemini C18, 110 Å, 5µ, 250×4.6 mm, 1 mL/min, 5/95/0.05→90/10/0.05 ACN/H$_2$O/TFA) showed mostly 2 peaks—deprotected starting material (6.5 min, 31%) and a new peak (4.3 min, 23%). LC/MS (Gemini C18, 3µ, 2.0×50 mm, 400 µL/min, A: 90/10/0.01 H$_2$O/MeOH/HOAc, B 90/10/0.01 MeOH/H$_2$O/HOAc 0-6 min 0-100% B, 6-9 hold at 100% B, 9.1-15 min re-equilibrate at 0% B) confirmed the presence of product (ESI$^+$ m/z 402).

Aza-adenosine Probe 4 is prepared from Compound 20C-iv in a manner similar to that described in Steps 2 and 3 used for preparation of Aza-adenine Probe 1.

Example 7

Preparation of Sinefungin Probe 5

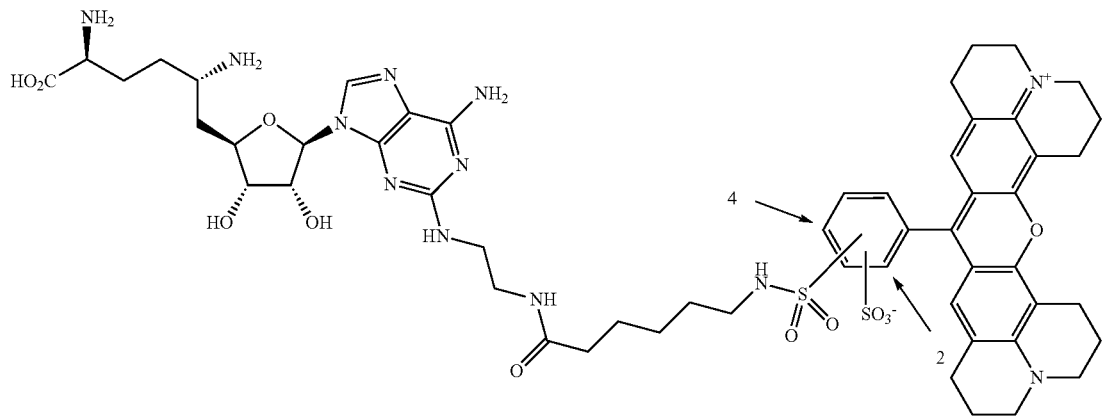

(Compound 31A)

Sinefungin Probe 5

Step 1: Preparation of tert-butyl (2-((6-amino-9H-purin-2-yl)amino)ethyl)carbamate (Compound 27A)

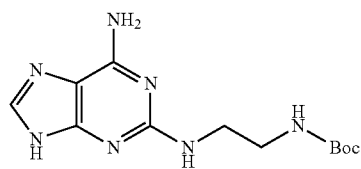 [SMILES: CC(C)(C)OC(=O)NCCNc1nc(N)c2nc[nH]c2n1]

To a microwave tube containing 2-chloroadenosine (Aldrich Chemical) is added tert-butyl N-(2-aminoethyl)carbamate (AK Scientific, 10-fold molar excess). The mixture is heated in a microwave for 20 minutes at 120° C. under nitrogen. Workup of the reaction mixture, purification, and isolation of the title intermediate is carried out in a manner similar to that of Example 4, ROUTE 1, Step 3 used for Compound 16A.

Step 2: Preparation of (2R,3R,4R,5R)-2-(6-amino-2-((2-((tert-butoxycarbonyl)amino)ethyl)amino)-9H-purin-9-yl)-5-((2S,5S)-2-azido-6-(tert-butoxy)-5-(4-methylphenylsulfonamido)-6-oxohexyl)tetrahydrofuran-3,4-diyl diacetate (Compound 28A)

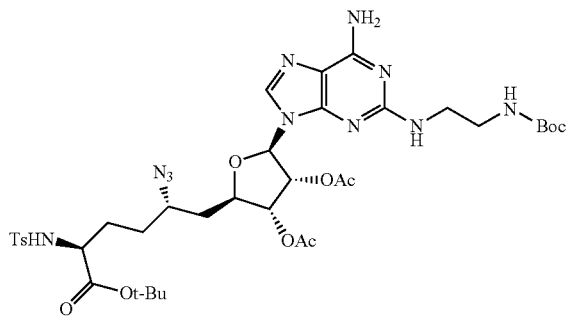

To a mixture consisting of Compound 27A (10 molar equivalents) in an appropriate solvent is added SnCl$_4$ (equimolar) in dichloroethane. A mixture consisting of (2S, 3R,4R,5R)-5-((2S,5S)-2-azido-6-(tert-butoxy)-5-(4-methylphenylsulfonamido)-6-oxohexyl)tetrahydrofuran-2,3,4-triyl triacetate (limiting reagent, prepared in the manner of Rapoport et. al. as 25β) is added and the mixture stirred at room temperature for 16 hours. The mixture is partitioned between ethyl acetate and 0.5N Na$_2$HPO$_4$ and the organics washed with brine, dried and evaporated. The residue is chromatographed on silica gel to obtain the title intermediate.

Step 3: Preparation of (2S,5S)-tert-butyl 6-((2R,3S, 4R,5R)-5-(6-amino-2-((2-((tert-butoxycarbonyl)amino)ethyl)amino)-9H-purin-9-yl)-3,4-dihydroxytetrahydrofuran-2-yl)-5-azido-2-(4-methylphenylsulfonamido)hexanoate (Compound 29A)

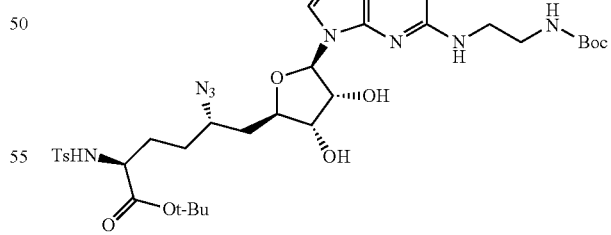

To a mixture consisting of Compound 28A in methanol is added potassium carbonate (10 molar equivalents) and the mixture stirred for 30 minutes at room temperature. Acetic acid is added to neutral pH and the solution is stirred 30 minutes. Solvent is evaporated and the mixture is partitioned between ethyl acetate and water. The organics are washed with brine, dried and evaporated. The residue is chromatographed on silica gel to obtain the title intermediate.

Step 4: Preparation of (2S,5S)-2,5-diamino-6-((2R, 3S,4R,5R)-5-(6-amino-2-((2-aminoethyl)amino)-9H-purin-9-yl)-3,4-dihydroxytetrahydrofuran-2-yl)hexanoic acid (Compound 30A)

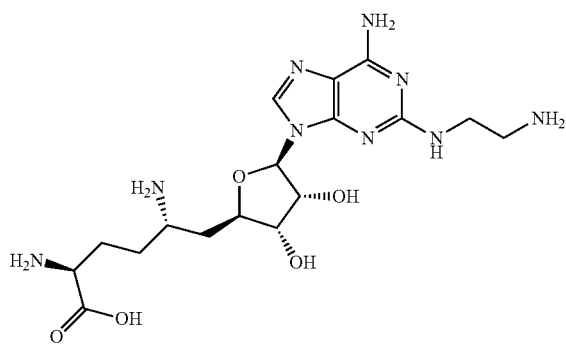 [SMILES: NCCNc1nc(N)c2ncn([C@@H]3O[C@H](C[C@@H](N)CC[C@H](N)C(=O)O)[C@@H](O)[C@H]3O)c2n1]

To a mixture consisting of Compound 29A in methanol is added Pd(OH)$_2$ on carbon. The mixture is shaken under hydrogen for two days and is subsequently diluted with methanol and ammonium hydroxide. The mixture is filtered through Celite and solvent evaporated to give intermediate amine. The material is dissolved into trifluoroacetic acid/water (9/1) and stirred for one hour. Solvent is evaporated and the residue is stirred in liquid ammonia at −78° C. Sodium is added (10 molar equivalents) and the solution is stirred for about one minute. Excess solid ammonium chloride is added and the ammonia is evaporated to give crude Compound 30A. This material is either used without further purification or is purified by preparative reverse phase HPLC.

Step 5: Preparation of Sinefungin Probe 5 (Compound 31A)

Conjugation of Compound 30A with Texas Red-X, Succinimidyl Ester (Life Technologies Catalog #T-6134): Compound 30A and Texas Red-X, succinimidyl ester are dissolved in a suitable solvent with a slight excess of a suitable base. The desired product, Sinefungin Probe 5, is obtained through workup and purification procedures disclosed elsewhere herein for other detection analytes.

Example 8

Saturation Binding: Sinefungin Probe 1A

Methods: The experiment was performed once, with two replicate wells for all methyltransferases per condition. The sole exception to this is NSD2 (see details below). The assay was performed in a ½ area, black, 96-well plate (Corning #3686) in a final volume of 30 μL. Methyltransferases (Table 1) were serially diluted two-fold in FP buffer (Cayman Catalog #600028) and 15 μL of a given dilution were added per well to the assay plate. Fifteen microliters of sinefungin probe 1A (10 nM) were added to each well, giving a final sinefungin probe 1A concentration of 5 nM. This concentration of sinefungin probe 1A was chosen because it had at least a 10-fold increase in fluorescence (excitation max 575 nm/emission max 615 nm) over background (buffer). The mixture was incubated in the dark at room temperature for 30 minutes and its fluorescence polarization was read using a BioTek Synergy 4.

For NSD2, the assay was performed essentially as above, but with the following changes. The assay was performed in a 20 μL total volume (10 μL NSD2/10 μL sinefungin probe 1) in low-volume, black, 384-well plates (Nunc #264705). The concentrations of sinefungin probe 1A and methyltransferase were identical to that of the 96-well format. The assay was performed once with three replicate wells per condition.

TABLE 1

| Methyltransferase | Cayman Product Item # |
| --- | --- |
| SET7/9 | 10320 |
| PRMT1 | 10350 |
| SET8 | 10319 |
| G9a | 49010353 |
| NSD2 | 10758 |

Figure 2:
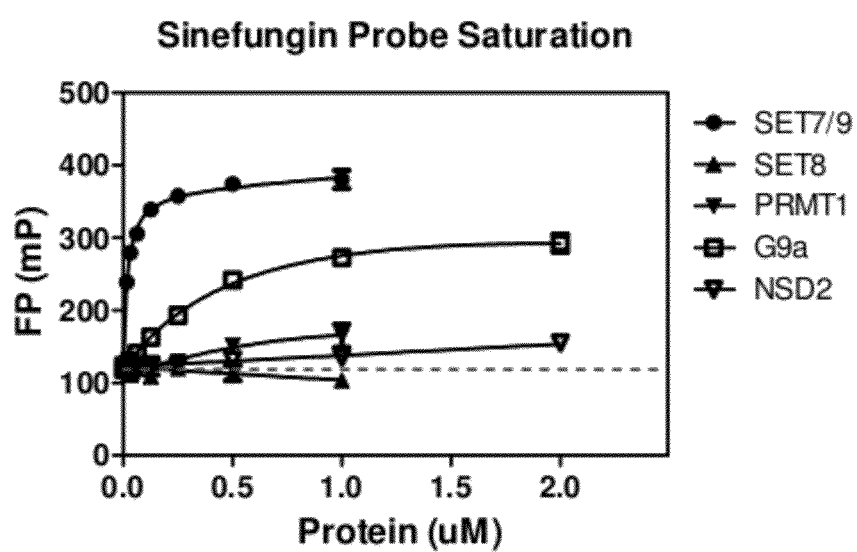
FIG. 2 is a plot illustrating saturation binding of Sinefungin Probe 1A with each of five different methyltransferase enzymes.

Results and Interpretation: Of the 5 methyltransferases tested, only SET7/9 and G9a displayed measurable affinity for sinefungin probe 1A (FIG. 2). SET7/9 bound sinefungin probe 1A with high affinity (Kd: 17 nM), while G9a has a lower affinity (Kd: ~700 nM) for the probe. These data suggest that sinefungin probe 1A is not a general S-adenosyl methionine (SAM)-binding site probe, but is selective for those binding sites that have structural characteristics which allow for the linker-fluorophore moiety of sinefungin probe 1A to be covalently attached at the sinefungin moiety 2'-ribose hydroxyloxygen atom.

Example 9

Sinefungin Probe 1A competition with SAM, SAH, and Unlabeled Sinefungin

Methods: Carboxymethyl cellulose-purified SAM, SAH (Cayman Catalog #700145), and sinefungin were diluted in a semi-Log manner in FP buffer (Cayman Catalog #600028). Five microliters of these dilutions were added to the wells of a low-volume, black, 384-well plate (Nunc #264705). Ten microliters of SET7/9 (60 nM) was added to the wells, followed by the addition of 40 nM sinefungin probe 1A (5 μL), providing final concentrations of 30 nM SET7/9 and 10 nM sinefungin probe 1. The assay was allowed to equilibrate at room temperature for 30 minutes in the dark. Fluorescence polarization was measured as above. The experiment was performed two independent times, each in duplicate.

Figure 3:
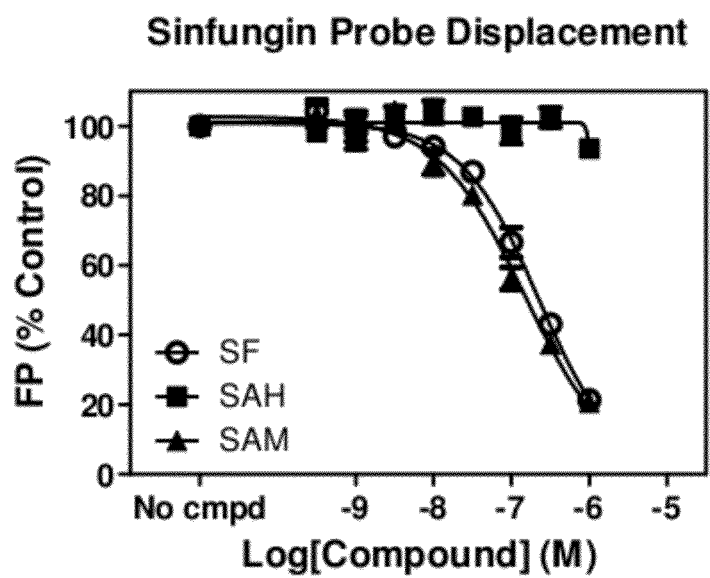
FIG. 3 is a plot illustrating concentration-response curves for SAM, SAH, and unlabeled sinefungin (SF) competing for binding to SET7/9 (30 nM) with Sinefungin Probe 1A (10 nM).

Results and Interpretation: Sinefungin Probe 1A was displaced in a concentration-dependent manner by SAM and unlabeled sinefungin with IC$_{50}$ values of 130 nM and 220 nM, respectively (FIG. 3). SAH did not compete with probe binding at concentrations below 1 μM. The potent inhibition of probe binding by SAM suggests that the compound is indeed binding at the SAM binding site. The inability of SAH to compete with sinefungin binding is likely explained by the low affinity of SAH for SET7/9. These data therefore suggest that Sinefungin Probe 1A is binding to SET7/9 in the SAM binding site.

Example 10

High-Throughput Screening of SET7/9 Using Sinefungin Probe 1A and Adaptation for Screening of GLP and MLL ("SAM-Screener" Assay)

Methods: A collection of 14,400 compounds from the Maybridge HitFinder collection of compounds was assayed for the displacement of Sinefungin Probe 1A from SET7/9 in a high-throughput manner using the SET7/9 SAM-Screener FP assay Cayman Catalog Item #600490). Thirty microliters of assay buffer (50 mM Tris pH 8.0, 50 mM KCl, 5 mM CHAPS, 2 mM DTT) was added to every well of a black 384-well polystyrene microtiter plate (Thermo-Fisher 364576). To every well, excluding control wells, was added one microliter of a DMSO solution containing a test compound. Control wells received either 1 μl DMSO or 1 μl of a sinefungin solution. The final concentration of sinefungin control or test compounds in the assay was 50 μM or 10 μM, respectively. To every well of the plate was added 10 μl of a SET7/9 solution to give a final assay concentration of 30 nM. After a 15-minute incubation at ambient temperature, 10 μl of Sinefungin Probe 1A solution was added to every well to give a final assay concentration of 10 nM in a total assay volume of 50 μl Samples were analyzed using a Biotek Synergy H4 plate reader in fluorescence polarization mode after a 30-minute incubation at ambient temperature in the dark. Data were analyzed using GeneData (v. 9.01).

Adaptation for GLP and MLL: Assays for probe binding to two other methyltransferases (GLP and MLL) were also adapted to high throughput format. The assay conditions were identical to the SET7/9 assay, however the protein concentration was increased to raise the signal:noise ratio for the assay. For GLP, the protein concentration was raised to 500 nM, while the concentration of MLL was raised to 1 μM. Data were analyzed in GraphPad Prism (v. 5.04) and/or GeneData (v. 9.01).

Concentration-Response Experiments: Compounds that displayed a Z-score<−3 from the mean of the test compounds wells were chosen for concentration-response follow-up experiments. In total, 47 compounds were selected for concentration-response follow up and were tested in 8-point serial concentration response curves in duplicate using the assay conditions and analysis methodology as described above.

Profiling of a pre-production version of the Cayman Chemical Epigenetics Screening Library (Cayman Catalog Item #11076) against SET7/9 and GLP was performed in a similar manner using Sinefungin Probe 1B. For GLP, the enzyme concentration was raised to 500 nM to produce a robust signal:noise ratio. Data were analyzed in GraphPad Prism (v. 5.04) and/or GeneData (v. 9.01).

Results: High-throughput adaptation of the SET7/9 SAM-Screener assay produced an assay capable of analyzing >20,000 data points per day with robust Z' scores (>0.6). High-throughput screening of the Maybridge HitFinder collection was performed in one day with an overall Z' score across the entire assay of 0.68 (Table 1). From this assay, 47 compounds were identified that had a Z score <−3 from the mean of the test compound wells. These compounds were subjected to confirmation concentration-response experiments, from which two compounds were determined to be active with an IC50 <250 μM. These compounds, KMN-10305 and KMN-10719 are currently being evaluated for their ability to inhibit methyltransferase activity.

TABLE 1

High-throughput screening data from an experiment that tested 14,400 compounds for Sinefungin Probe 1A-displacement activity from SET7/9.

|  | Compounds Tested | "Actives" | Confirmation Rate (% total) |
|---|---|---|---|
| Primary Screen | 14400 | 47 | 0.3 |
| CRC* 2° Assay | 47 | 2 | 0.01 |

*CRC = concentration response curve

A pre-production version of the Cayman Epigenetics Screening Library was profiled in an 8-point concentration-response format against the methyltransferases SET7/9 and GLP. For both sets of experiments the Z' values were >0.6 and from each compound. Of the 44 compounds tested in this experiment, only sinefungin showed appreciable inhibition against SET7/9. Similar results were observed for GLP, however, UNC0638 also inhibited probe binding with an $IC_{50}$ value of 32 nM.

Figure 10:
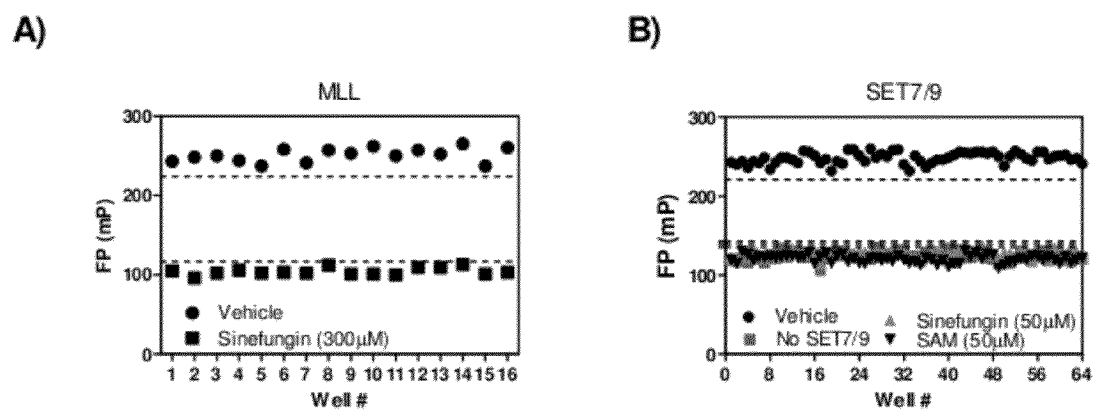
FIG. 10 is a plot illustrating binding affinity of Sinefungin Probe 1A in high-throughput fluorescence polarization-based assays for MLL and SET7/9.

This assay was also adapted for high throughput format against the methyltransferase MLL (Cayman Catalog Item #10658). Relevant data are illustrated in FIG. 10: The fluorescence polarization (FP) Sinefungin Probe 1A binding assay was adapted to a high-throughput inhibitor screening format for both A) MLL and B) SET7/9. The probe polarization is increased by >120 mp by binding to SET7/9 (30 nM) and by >145 mp by binding to MLL (1 μM). As controls, sinefungin (50 μM for SET7/9, 300 μM for MLL) or SAM fully inhibits probe binding. Sixty-four replicates were tested for each condition for SET7/9, sixteen replicates were tested for MLL. Z' factor scores were >0.5 for all conditions tested (SET7/9:sinefungin: 0.71; SAM: 0.72; no SET7/9: 0.69; MLL:sinefungin: 0.72).

Example 11

Sinefungin Probe SAR Studies

Sinefungin Probe 1A was tested for the ability to bind to 16 proteins, including several non-methyltransferase protein controls (Table 2). This probe binds to 4 methyltransferases (SET7/9, G9a, GLP, MLL) with Kd values <2 μM.

TABLE 2

Sinefungin Probe 1A affinity for each of the proteins tested.

| Protein | Sinefungin Probe 1A Affinity (μM) | Confirmation Assay Type |
|---|---|---|
| SET7/9 | 0.027 ± 0.0015 | Colorimetric |
| G9a | 1.8 ± 1.0 | Colorimetric |
| KMT5b | 6.1 ± 0.8 | Radiometric |
| PRDM9 | 2.6 ± 0.6 | Radiometric |
| GLP | 0.58 ± 0.05 | Colorimetric |
| MLL | 0.75 ± 0.065 | Radiometric |
| PRMT1 | >1.2 | Colorimetric |
| NSD2 | >2 | Radiometric |
| SET8 | >2 | Colorimetric |
| KMT5c | >2 | Radiometric |
| DNMT3b | >2 | N/A |
| PRMT4 | >2 | Radiometric |
| ASH2L | >10 | N/A |
| Lysozyme | >10 | N/A |
| Trypsin | >10 | N/A |
| Sumo | >10 | N/A |

All proteins were tested in a saturation-binding format and data are presented as the mean ± SEM from at least two independent experiments performed in duplicate. Enzymatic activities of the proteins were confirmed using an orthogonal assay as listed in the table.

Figure 11:
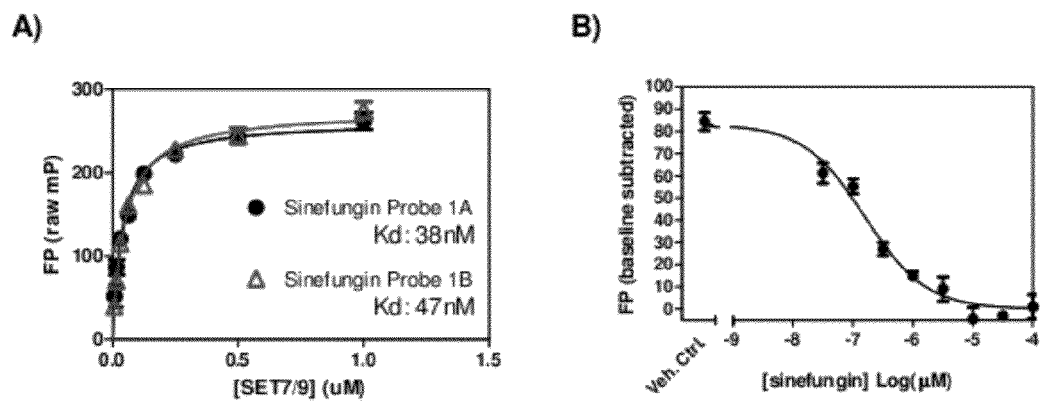
FIG. 11 is a plot illustrating the binding affinity of Sinefungin Probe 1A and Sinefungin Probe 1B to SET7/9.

An analog of Sinefungin Probe 1A, Sinefungin Probe 1B, wherein the hexyl portion of the linker moiety is replaced with PEG$_3$ and the Cal Fluor® Red 610 fluorophore moiety is replaced with the "Fluor585" (Texas Red)-derived fluorophore moiety, was tested for the ability to bind several methyltransferases, including SET7/9. These two probes bind to SET7/9 with essentially identical affinities and are displaced by sinefungin in a similar manner (FIG. 11: A) Sinefungin Probe 1A (comprising Cal Fluor® fluorophore) and Sinefungin Probe 1B (comprising Fluor585 fluorophore) bind to SET7/9 with similar affinities. Similar data have been observed for GLP and G9a. B) Sinefungin is able to displace Sinefungin Probe 1B binding to SET7/9 with a K$_i$ value of 120 nM, which corresponds well with the 168 nM K$_i$ values calculated for displacement of Sinefungin Probe 1A).

Similar experiments were performed using Sinefungin Probe 3, wherein the "click" triazole ring portion of the linker moiety of Sinefungin Probe 1B is replaced with the "non-click" tether-portion of the linker moiety as shown in Example 2 above.

Figure 12:
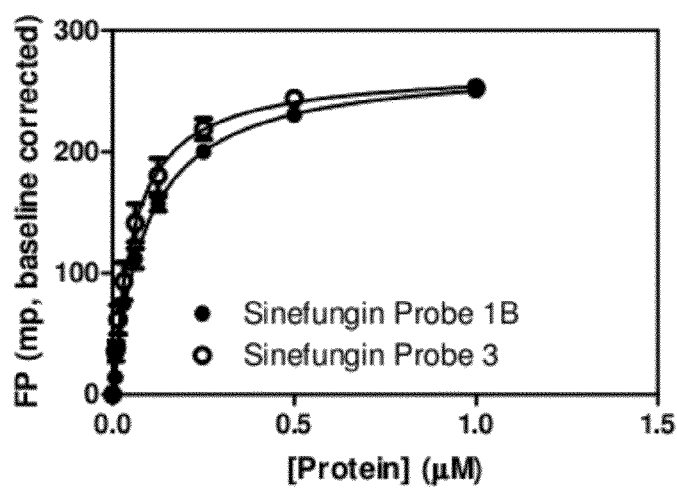
FIG. 12 is a plot illustrating the binding affinities of Sinefungin Probe 3 and Sinefungin Probe 1B to SET7/9.

Sinefungin Probe 3 bound to SET7/9 with similar affinity to that of the click-linker based probes Sinefungin Probes 1A and 1B (FIG. 12). This probe was tested in parallel with Sinefungin Probe 1B to determine whether it possessed increased affinity for any methyltransferases. None of the 7 methyltransferases tested (SET7/9, PRDM9, G9a, NSD2, MLL, KMT1b, SETS) showed significantly greater affinity for the non-click probe than the click-based probe.

Example 12

Radiometric Profiling of Various Thioadenosine and Aza-Adenosine Probe Synthetic Precursors Overview: Three adenosine-type probe synthetic precursors were tested against a panel of 7 methyltransferases using a radiometric methyltransferase assay. In general, Thioadenosine Probe 1 synthetic precursor Compound 16A displayed inhibitory activity against 4 of the 7 enzymes tested, while two Aza-adenosine probe precursors, Compounds 20A-iv and 20A-iii, showed substantially less potency against the panel of methyltransferases.

Reagents: Compound 16A was prepared by the method described in Example 4 and illustrated in FIG. 5. The Compounds 20A-iv and 20A-iii were prepared according to methods described in Example 6 and illustrated in FIG. 7. Enzymes were obtained from the Cayman Catalog with the exception of PRMT4 and PRMT6, which were produced in baculovirus and purified to near homogeneity using Ni-affinity chromatography. Human core histones were purified from HeLa nuclear pellet per the method of Coté et al. S-adenosylmethionine (SAM) was obtained from Sigma-Aldrich (Cat #A7007) and S-[methyl-3H]-SAM was obtained from Perkin-Elmer (Cat#NET155H001MC).

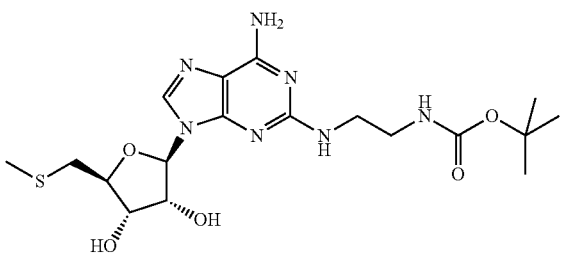

Compound 16A

N$^1$—Boc—N$^2$-(5'-MTA-2-yl)EDA

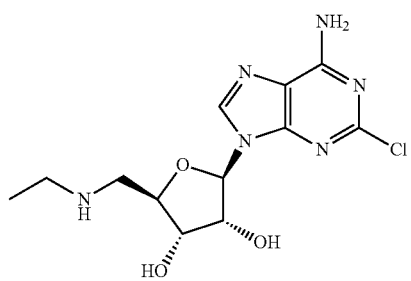

Compound 20A-iv

2-Chloroadenosine-5'-ethylamine

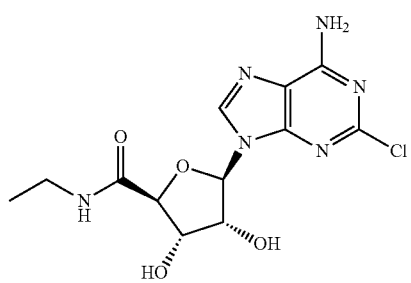

Compound 20A-iii

2-Chloroadenosine-5'-N-ethylcarboxamide

Structures of the compounds that were tested in this profiling experiment.

Methods: Compounds or vehicle control were diluted in assay buffer (50 mM Tris pH 8.0, 150 mM NaCl, 3 mM MgCl2, 5% glycerol, 1 mM dithiothreitol) to a final assay concentration of 10 µM, 1 µM, or 0.1 µM and were plated into V-bottom polypropylene 96-well plates. To this was added enzyme diluted to provide a final assay concentration (GLP: 10 nM; PRMT1: 100 nM; SET7/9: 120 nM; PRDM9: 120 nM; PRMT4: 150 nM; PRMT6: 120 nM; G9a: 200 nM) and the compound was allowed to preincubate for 10 minutes at room temperature. Reactions were initiated by adding core histones, SAM, and S-[methyl-3H]-SAM to final assay concentrations of 2.5 µM, 700 nM and 300 nM, respectively. Reactions were allowed to progress at room temperature for 30 minutes, at which time they were quenched with bovine serum albumin and SAM to final reaction concentrations of 0.33% and 100 µM, respectively. Samples were mixed immediately after quenching and transferred to a 96-well GFC Uni-Filter microtiter filter plate (Perkin Elmer, Cat#6005174) that contained 50 µl of 20% TCA. Samples were allowed to precipitate for at least 5 minutes at room temperature. The samples were filtered onto the GFC membrane and washed four times with 100 µl of 10% TCA and once with 100 µl of 95% EtOH. To each well was added 25 µl of MicroScint-20 (Perkin-Elmer Cat#6013621) and samples were analyzed using a TopCount NXT microplate scintillation counter. The experiment was performed one time in duplicate for all compound concentrations tested and in triplicate for the vehicle and no enzyme controls. All data was analyzed in GraphPad Prism (v. 5.04).

Figure 13:
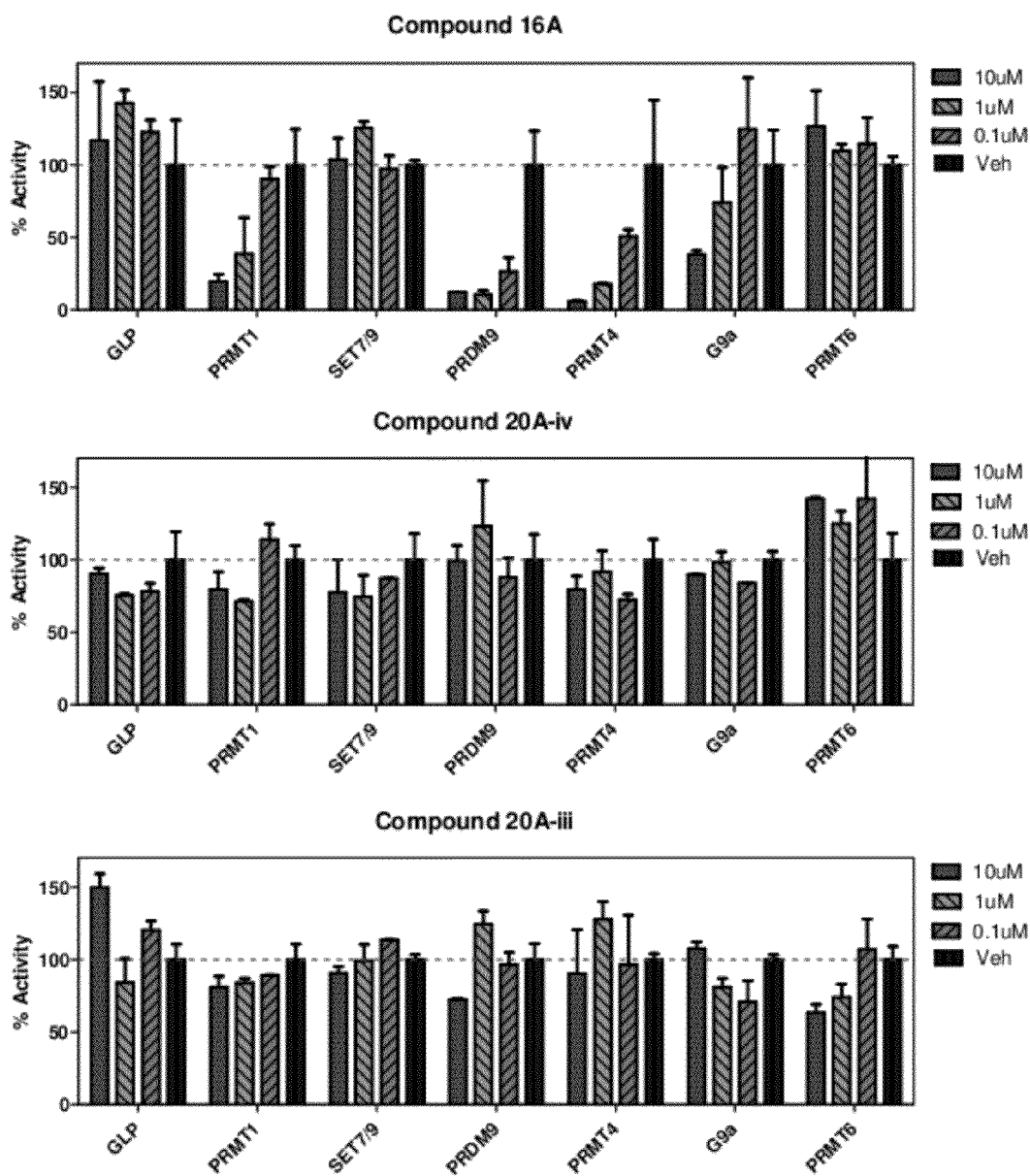
FIG. 13 plots profiling data for Probe synthetic precursors Compounds 16A, 20A-iv, and 20A-iii against seven methyltransferases.

Results: Compound 16A displayed the greatest inhibitory activity against the broadest panel of enzymes (FIG. 13). This compound inhibits PRMT1 and PRMT4, PRDM9, and G9a, while not dramatically altering the activity of GLP, PRMT6 and SET7/9. Compounds 20A-iv and 20A-iii did not show appreciable inhibition against the enzymatic activity of any of the enzymes tested, with the exception of PRMT6, for which Compound 20A-iii displayed some modest inhibition.

Figure 14:
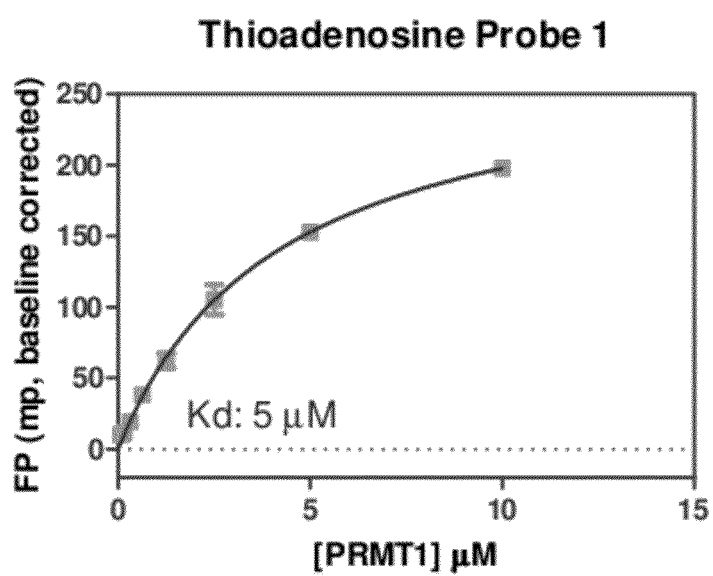
FIG. 14 is a plot illustrating the binding affinity of Thioadenosine Probe 1 to PRMT1.

Thioadenosine Probe 1 displayed about a 5 µM binding affinity (Kd) with PRMT1 (FIG. 14).

Example 13

TR-FRET Assay Procedure

Procedure:
Materials Required:
Buffer: FP buffer (e.g. Cayman Catalog #600028)
Receptor: Lanthanide chelate-labeled SAM-utilizing protein (direct chemical labeling or secondary labeling via labeled antibody or streptavidin; label example: LanthaScreen Tb chelate, Invitrogen)
Assay Plate: low volume, 384 well black plate (e.g. Nunc #264705)
Dilution plate: ½ area 96-well plate (e.g. Corning 3695)
Suitable multimode plate reader (e.g. BioTek Synergy H4)

The assay described here is an isothermal saturation binding experiment designed to measure the affinity (Kd) of Sinefungin Probe 1A, Sinefungin Probe 2A, or a similar sinefungin-linker-fluorophore probe (probe), as exemplified in the embodiments described herein, with a donor fluorophore (a lanthanide chelate)-labeled SAM-utilizing protein (receptor). Simple adaptation would allow this assay to be used for competition binding experiments including high throughput screening. The assay is described in a 384-well format, but can be scaled to desired volume or plate format as needed.

The assay is performed in a total volume of twenty microliters, with ten microliters comprising a solution of the receptor and ten microliters of the probe. Final concentrations of the reagents are as such: receptor: 0 nM or 10 nM; probe or general probe: 1.4 nM→3 µM in a series of twelve two-fold dilutions.

1) The probe is serially diluted two-fold in a 96 well plate across one of the rows, generating 12 dilutions of the probe or general probe.
   a. The probe is diluted to 6 µM in buffer and is subsequently serially diluted across plate by adding 100 µL of 6 µM stock to well A1 and 50 µL buffer to wells A2-A12. Serially dilute by transferring 50 µL in a stepwise manner across the row, mixing thoroughly in each well.
2) Transfer 10 µL of the diluted probe to two sets of duplicate wells (four wells total per concentration of probe) in a low-volume 384 well black plate.
3) To one set of duplicate wells, add 10 µL of 20 nM receptor. To the other set of duplicate wells, add 10 µL buffer.
4) Allow the reaction to incubate for 30 minutes at room temperature, protected from light.
5) Analyze the reaction using a BioTek Synergy H4 (or similar) multimode plate reader with TR-FRET capability.
   a. Instrument sensitivity is adjusted by normalizing the fluorescence values to a buffer-filled (200 µL) well.
   b. Samples are measured in a time resolved manner using a 200 µs delay before initiating a 500 µs data collection window.
   c. Data are collected using a xenon flash bulb and appropriate excitation and emission filter sets for the FRET pair:
      i. E.g. Tb chelate/fluorescein FRET pair: Excitation 360 nm/40 nm bandpass; Emission 460 nm/40 nm bandpass and 528 nm/20 nm bandpass.
6) Data analysis and Expected results:
   a. Data are transformed as the ratio of the 528 nm emission/460 nm emission (TR-FRET ratio) and are plotted on an XY scatter graph as TR-FRET ratio vs. [probe] (nM).
      i. For the probe dilution series that contains only buffer and probe, it is expected that the TR-FRET ratio will increase in a linear fashion with a shallow slope. This is background signal from the assay.
      ii. For the probe dilution series that contains both probe and receptor, the TR-FRET ratio will increase in the shape of a rectangular hyperbola summed with a background linear component.
   b. For each concentration of probe, subtract the assay background (probe+buffer wells) from the saturation binding wells (probe+receptor wells) to obtain the receptor-specific TR-FRET signal.
   c. Calculate Kd using nonlinear regression to fit the background-corrected data to the model:

$$Y = B_{max} * X / (Kd + X)$$

Adaptations:

The assay can be adapted for competition analysis of unlabeled competitors by testing increasing concentrations of the unlabeled competitor against a fixed concentration of probe and receptor. Ideally, the probe concentration in this format should be approximately 80% of the maximal TR-FRET signal and receptor concentration should be less than twice the expected $IC_{50}$ value of the competitor. For this experiment, plot the data as TR-FRET Ratio vs. $\text{Log}_{10}$[competitor] (M). Calculate $IC_{50}$ using nonlinear regression to fit the data to the model:

$$Y = \text{Bottom} + (\text{Top} - \text{Bottom}) / (1 + 10^{((\text{Log } IC_{50} - X) * \text{Hill-Slope})})$$

Where:
Bottom=lower bound of TR-FRET signal (assay background, e.g. vast excess of competitor)
Top=upper bound of TR-FRET signal (no competitor present)
HillSlope=Hill coefficient; the slope of the curve around the $IC_{50}$ value References The standard fitting models described here were obtained from GraphPad Prism version 5.04.

It should be understood that the detailed description and specific examples, while disclosing exemplary embodiments of the invention, are intended for purposes of illustration only and are not intended to limit the scope of the invention.

What is claimed is:

1. A fluorescent detection analyte having the structure of Formula (II):

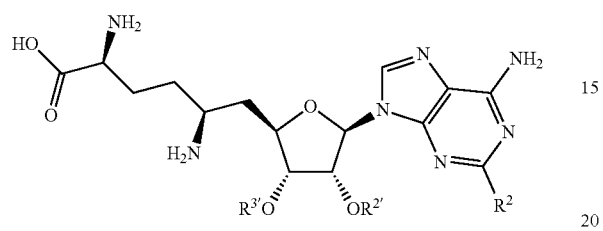

(II)

wherein any two of R², R²', and R³'R³' are hydrogen and the third is a linker component having a linker moiety bonded to a fluorophore moiety.

2. A fluorescent detection analyte having the structure of Formula (III):

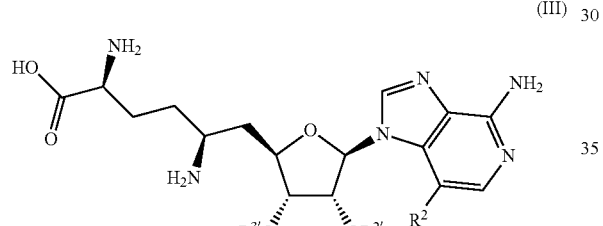

(III)

wherein any two of R², R²', and R³' are hydrogen and the third is a linker component having a linker moiety bonded to a fluorophore moiety.

3. A fluorescent detection analyte having the structure of Formula (IV):

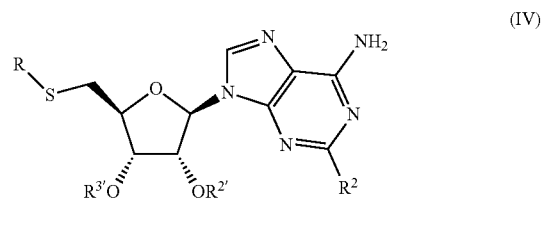

(IV)

wherein any two of R², R²', and R³'R³' are hydrogen and the third is a linker component-having a linker moiety bonded to a fluorophore moiety and wherein R is hydrogen, $C_{1-8}$ alkyl, $C_{2-6}$ alkynyl, $C_{3-6}$ cycloalkyl, $C_{6-10}$ aryl, five-to-ten membered heteosryl, five- to ten-membered heterocycyl, $C_{1-8}$ acyl, or [(S)-2-aminobutanoic acid]-4-yl.

4. A fluorescent detection analyte selected from the group consisting of Sinefungin Probe 1A, Sinefungin Probe 1B, Sinefungin Probe 2A, Sinefungin Probe 2B, Sinefungin Probe 3, Sinefungin Probe 4, Sinefungin Probe 5, Sinefungin Probe 6, Sinefungin Probe 7, Sinefungin Probe 8, Sinefungin Probe 9, Sinefungin Probe 10, Sinefungin Probe 11, Sinefungin Probe 12, Sinefungin Probe 13; wherein any A⁻ is $PF_6$ or trifluoroacetate, or a mixture thereof, each respectively illustrated blow:

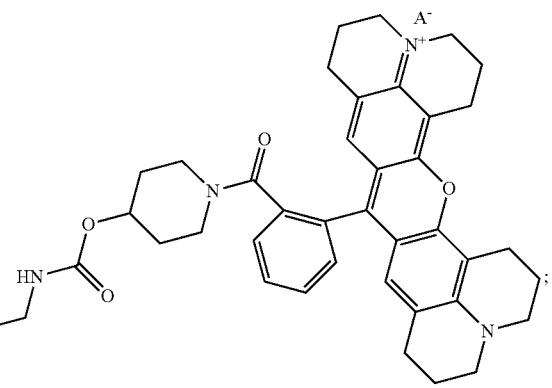

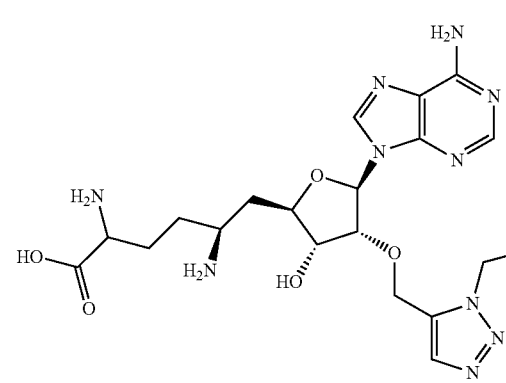

A- is $PF_6^-$ or $F_3COO_2^-$ or a mixture thereof
Compound 1A
(Sinefungin Probe 1A)

-continued
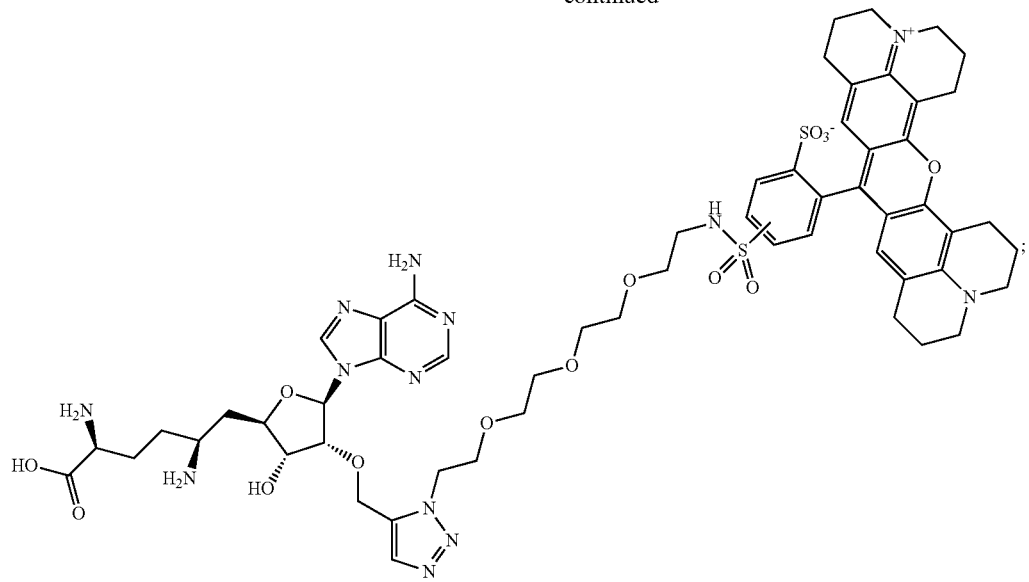
Compound Regioisomer Mixture 1B
(Sinefungin Probe 1B)
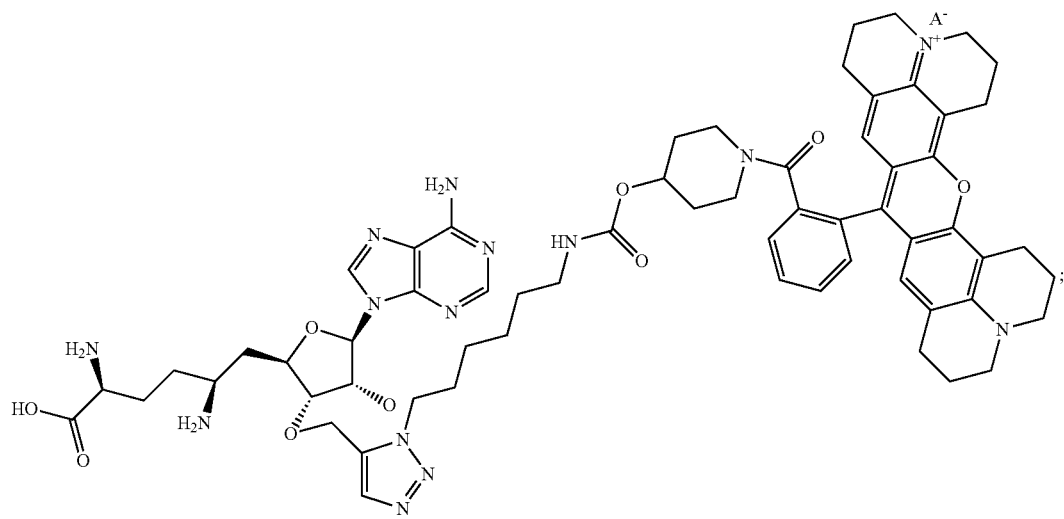
A⁻ is PF$_6^-$ or F$_3$COO$_2^-$ or a mixture thereof
Compound 2A
(Sinefungin Probe 2A)
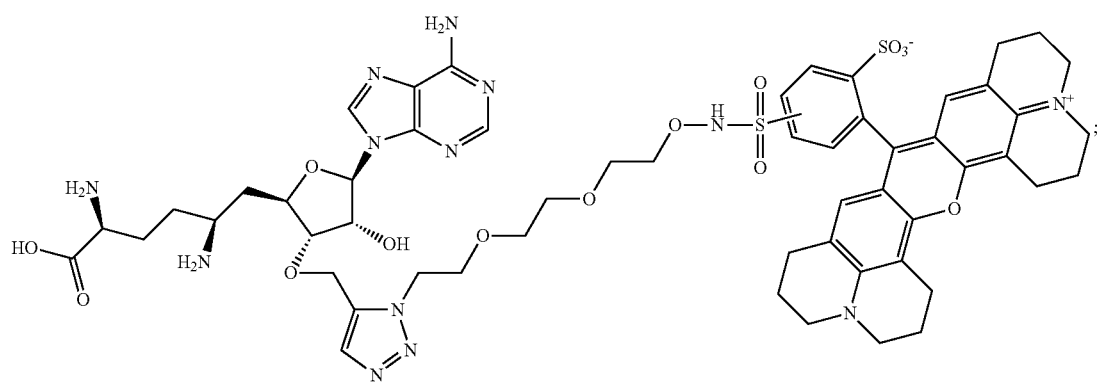
Sinefungin Probe 2B -continued
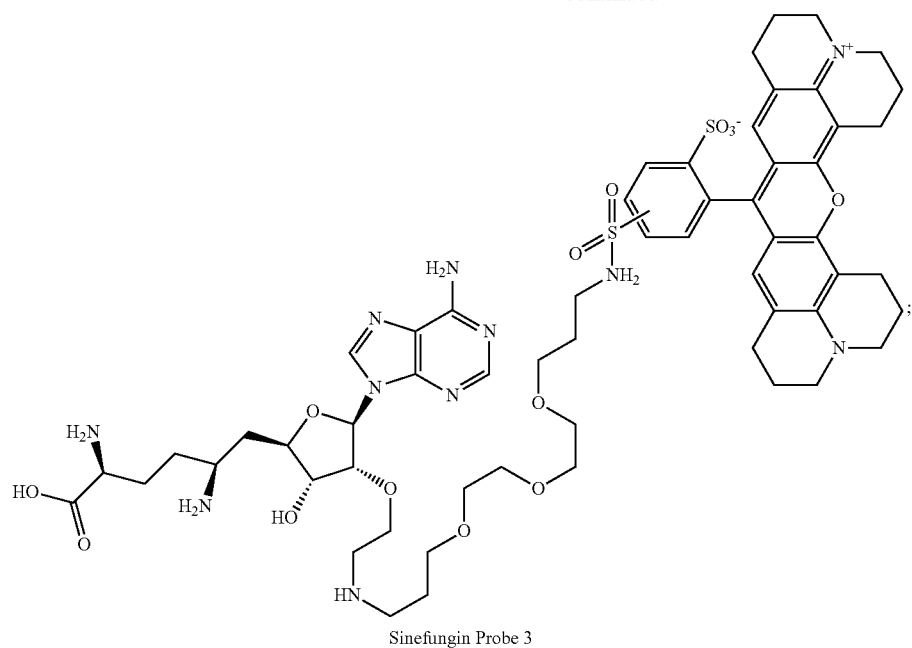
Sinefungin Probe 3
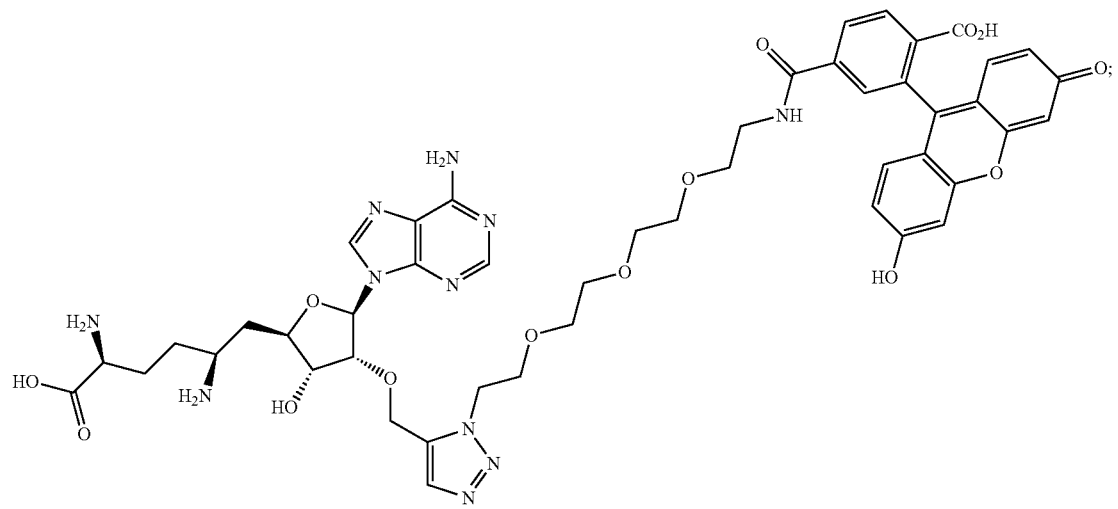
Sinefungin Probe 4

-continued
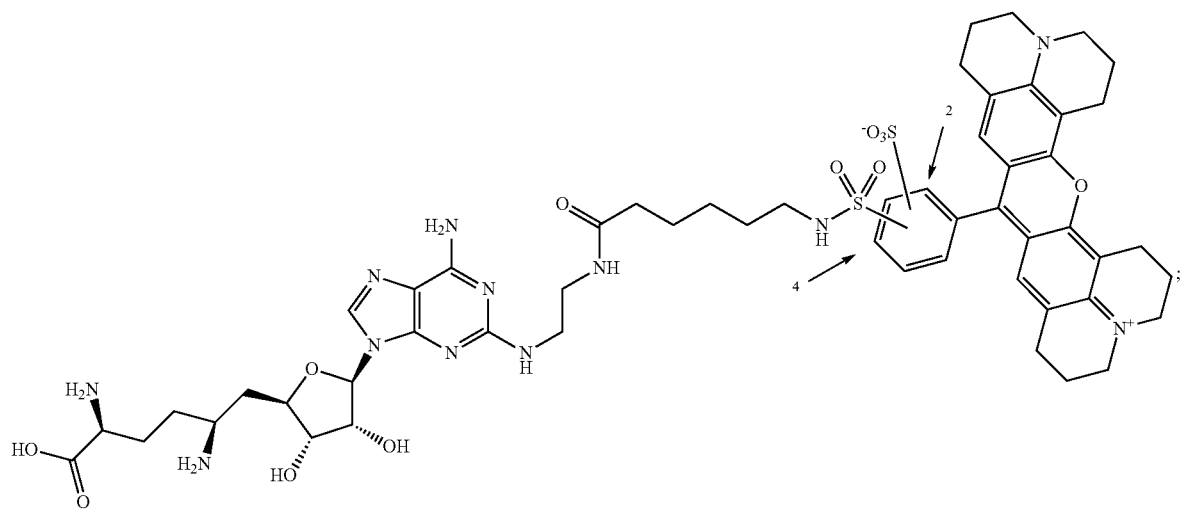
Sinefungin Probe 5
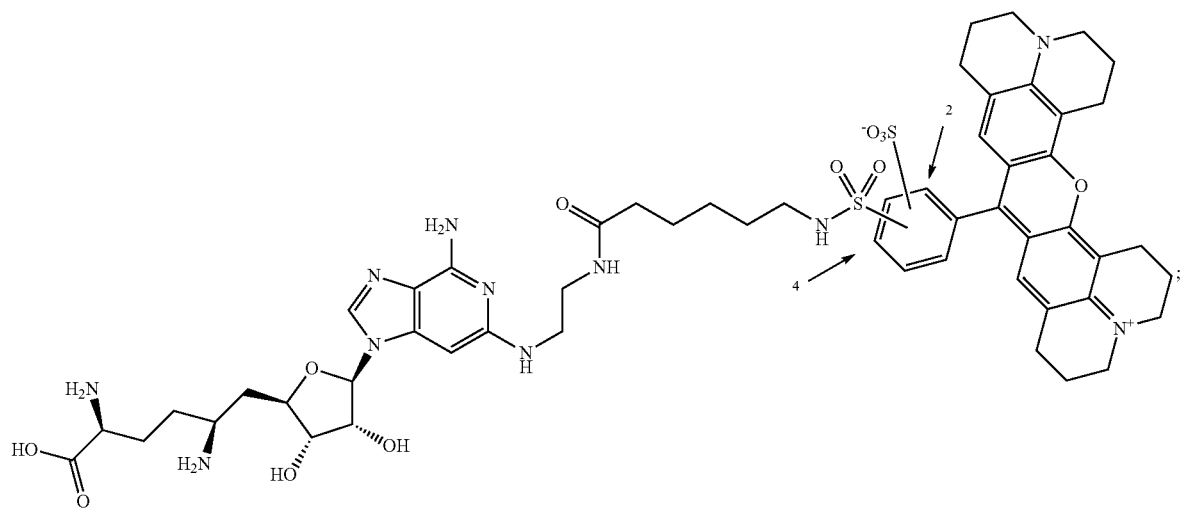
Sinefungin Probe 6

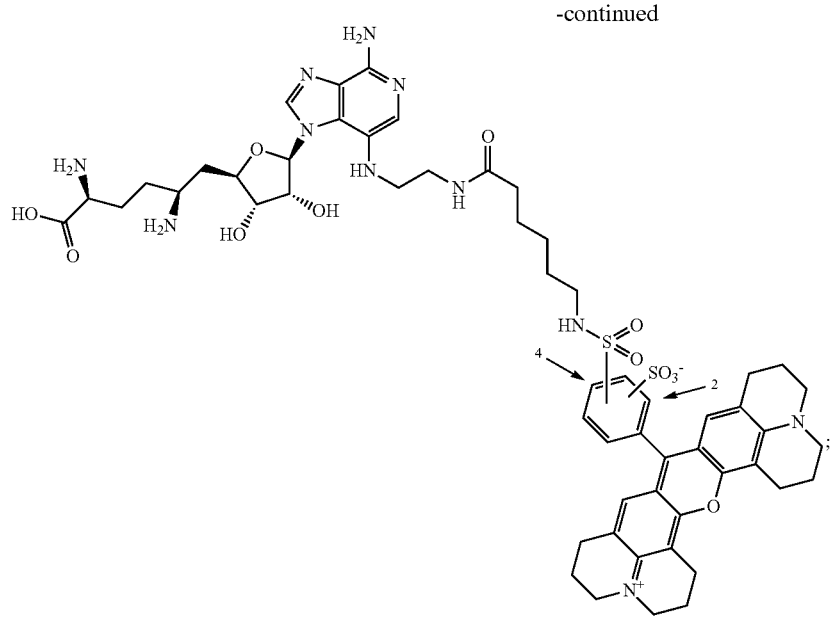
Sinefungin Probe 7
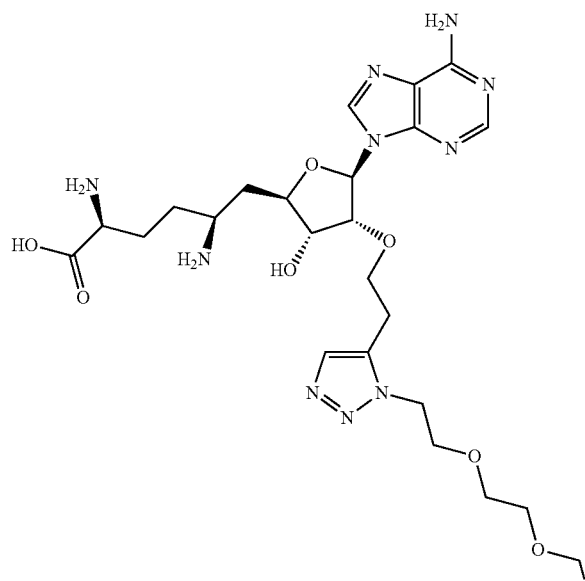

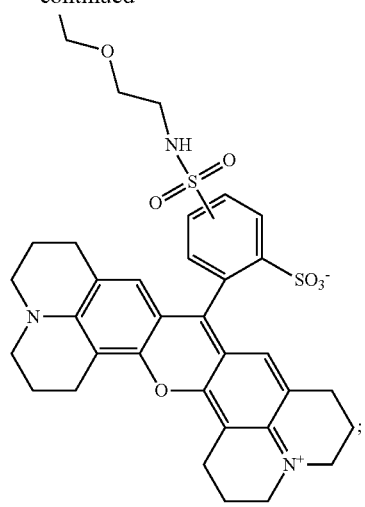
Sinefungin Probe 8
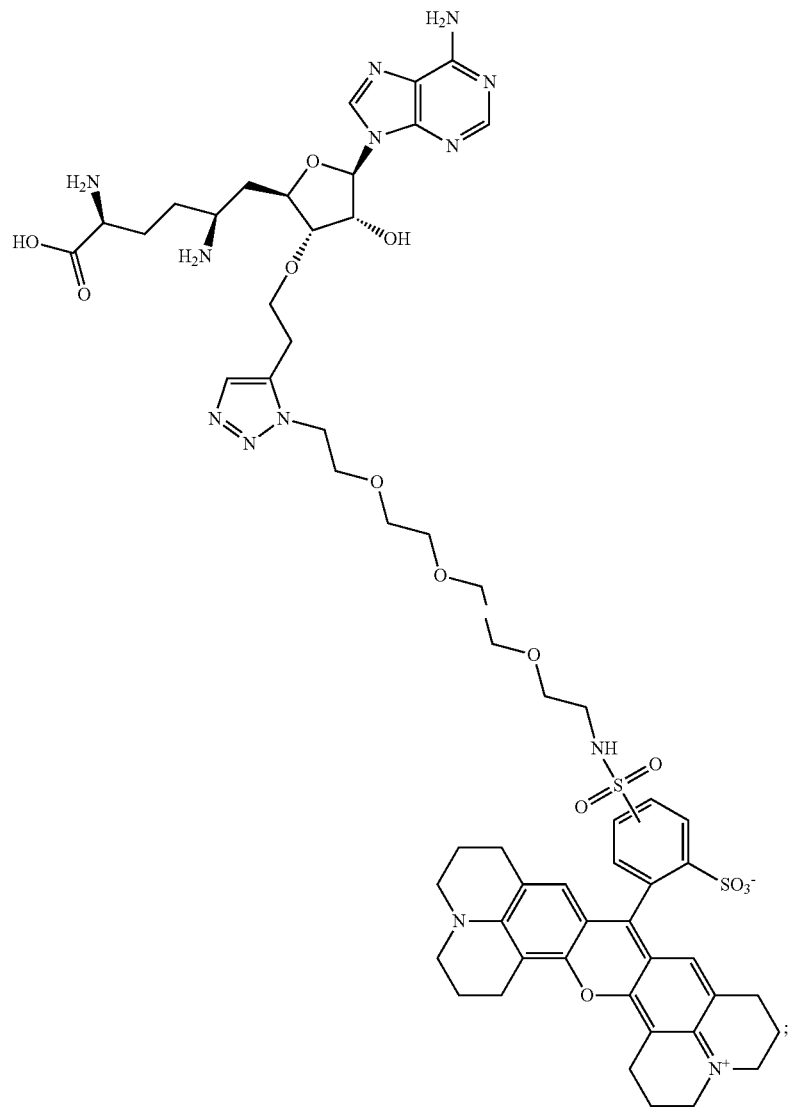
Sinefungin Probe 9

-continued
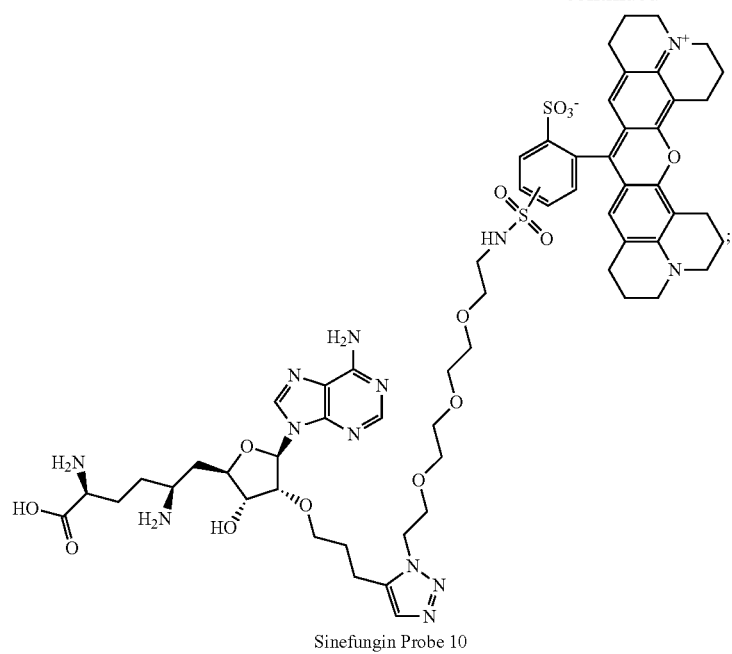
Sinefungin Probe 10
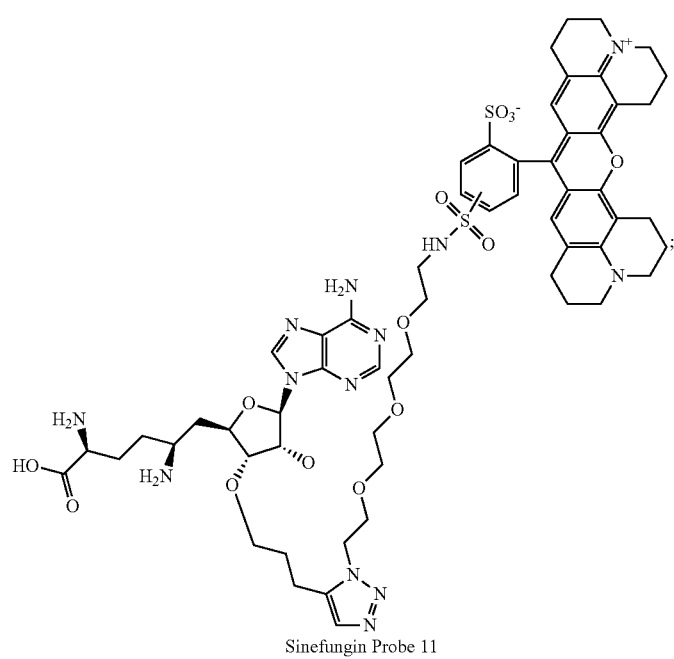
Sinefungin Probe 11

-continued
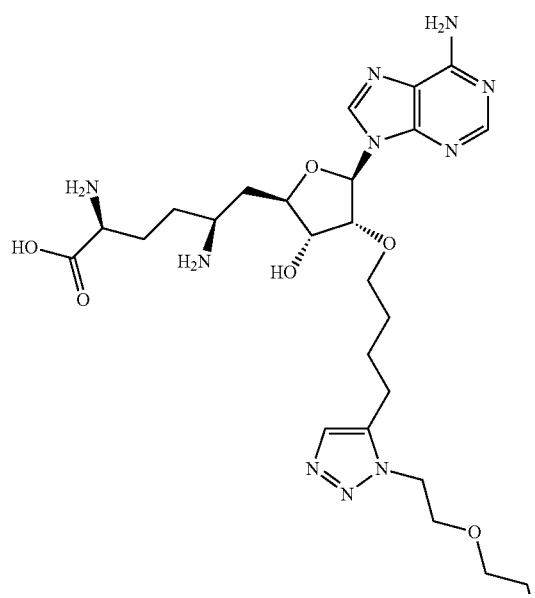
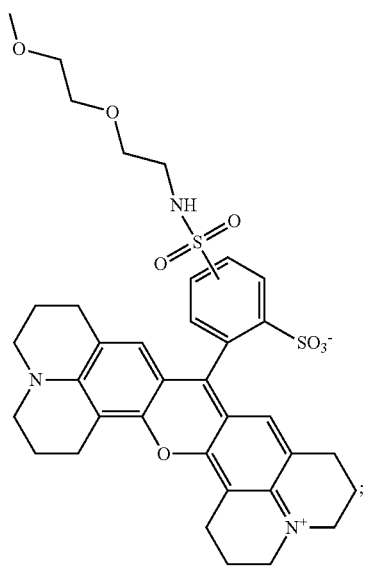
Sinefungin Probe 12

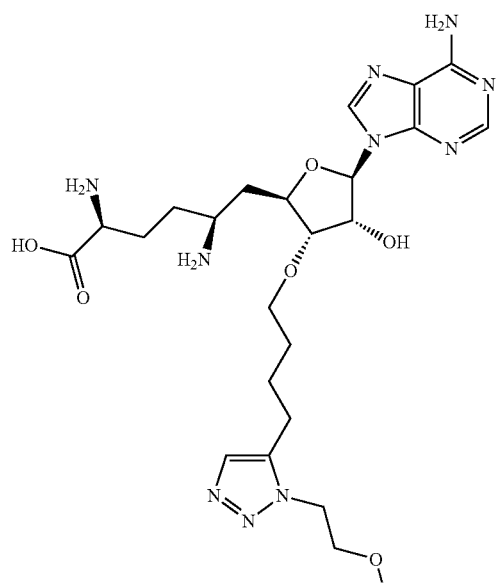
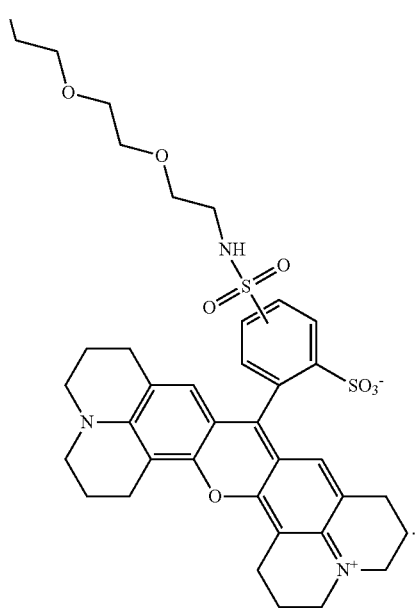
Sinefungin Probe 13

5. A fluorescent detection analyte selected from the group consisting of Thioadenosine Probe 1 and Thioadenosine Probe 2 each respectively illustrated blow:

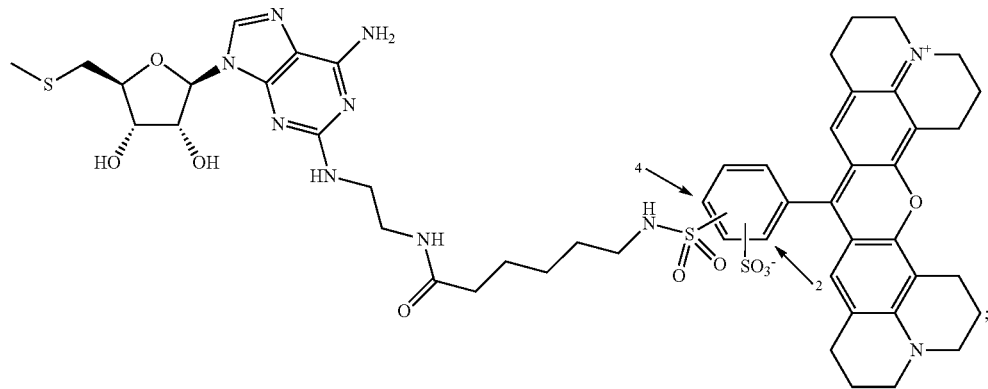

Thioadenosine Probe 1

Thioadenosine Probe 2

6. A fluorescent detection analyte selected from the group consisting of Aza-adenosine Probe 1, Aza-adenosine Probe 3, Aza-adenosine Probe 5, Aza-adenosine Probe 6, Aza-adenosine Probe 7, Aza-adenosine Probe 8, Aza-adenosine 9, Aza-adenosine Probe 10, Aza-adenosine Probe 11, each respectively illustrated below:

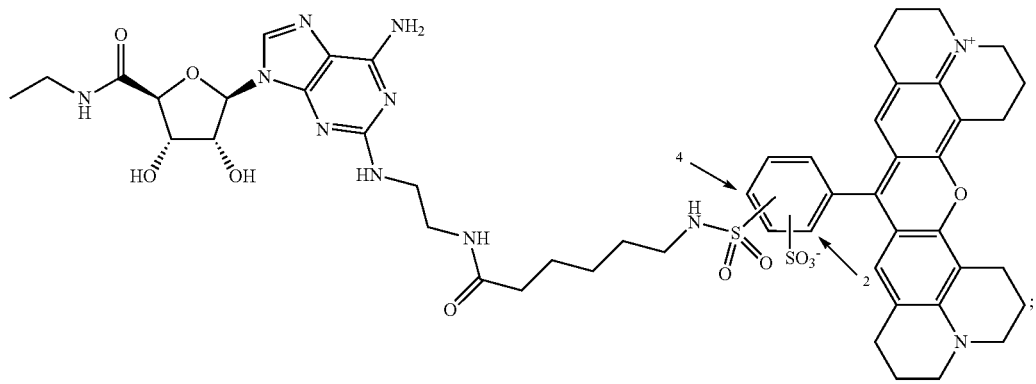

Aza-adenosine Probe 1 (Compound 22A-iii)

-continued
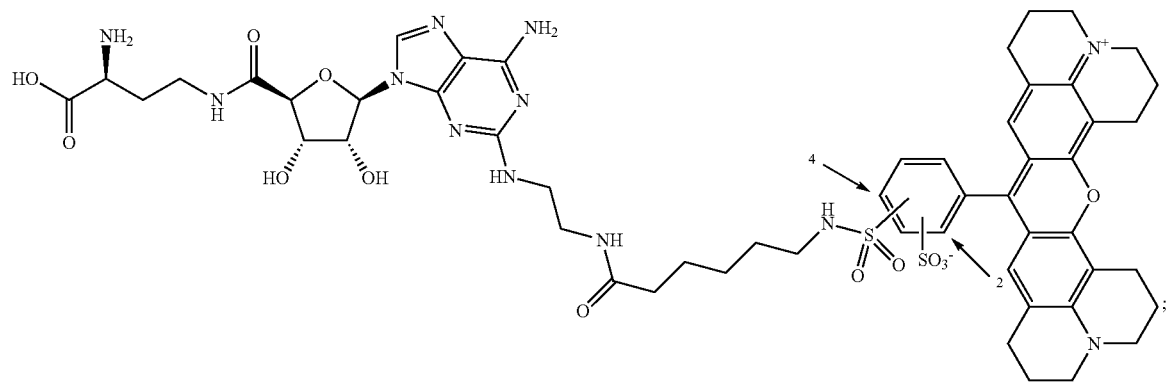
Aza-adenosine Probe 3 (Compound 22B-iii)
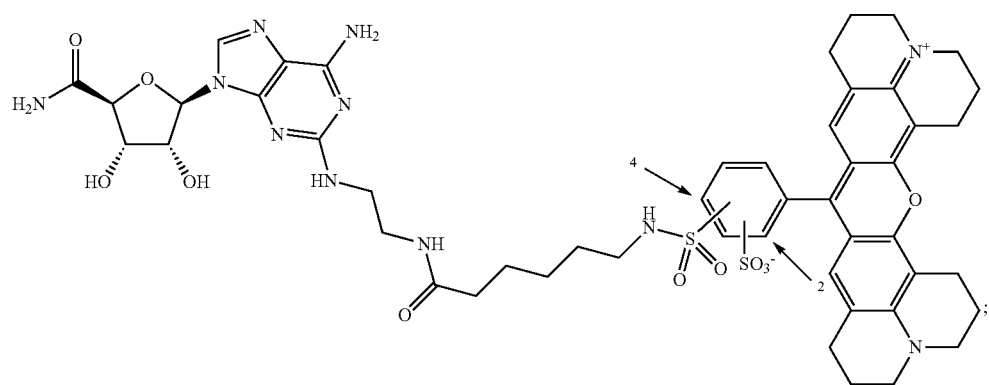
Aza-adenosine Probe 5
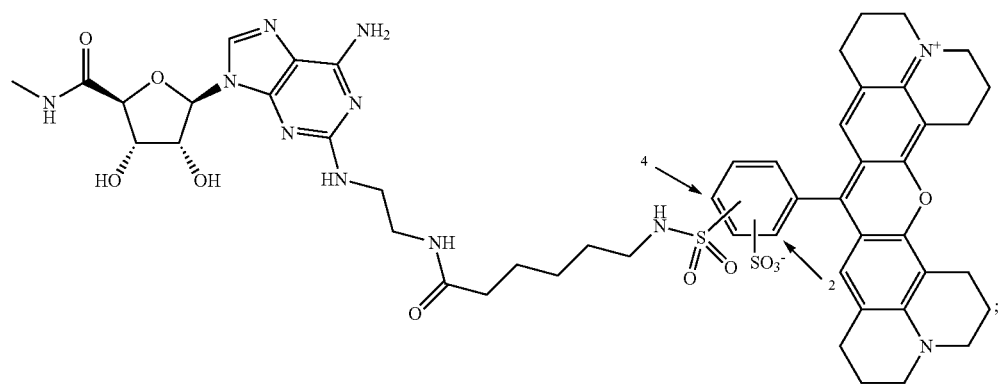
Aza-adenosine Probe 6

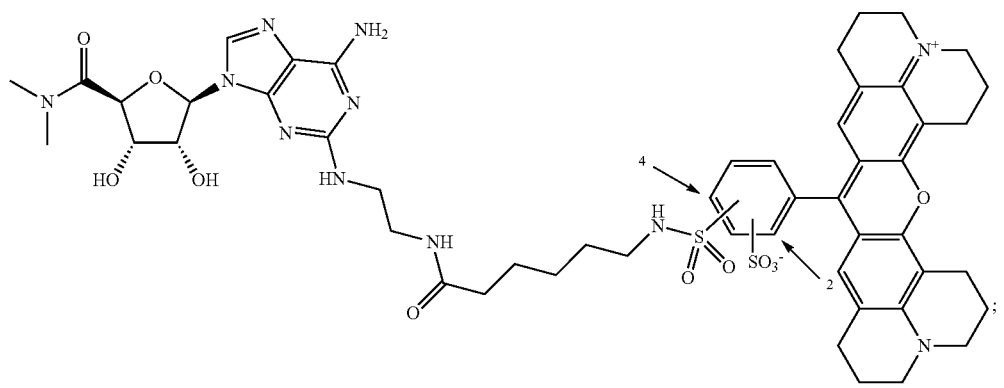
Aza-adenosine Probe 7
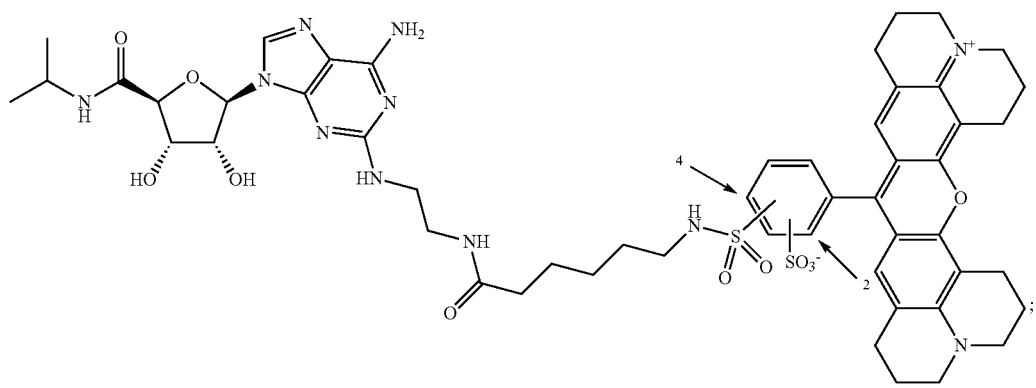
Aza-adenosine Probe 8
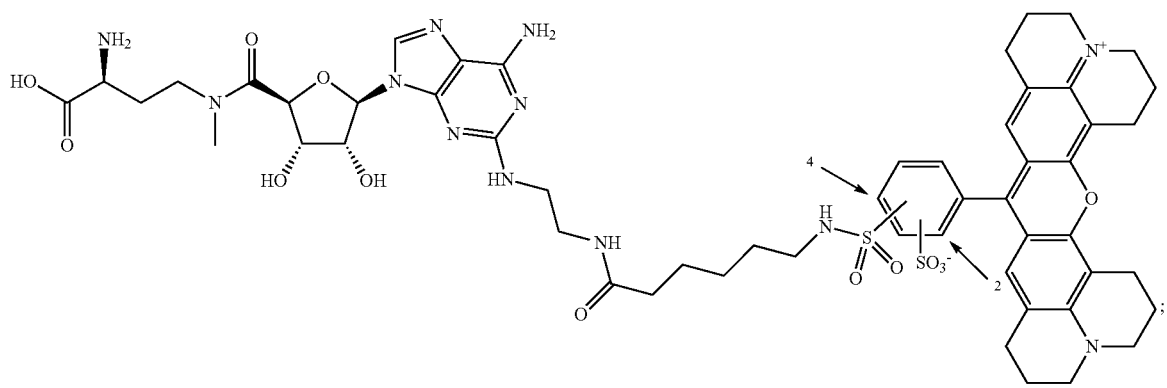
Aza-adenosine Probe 9

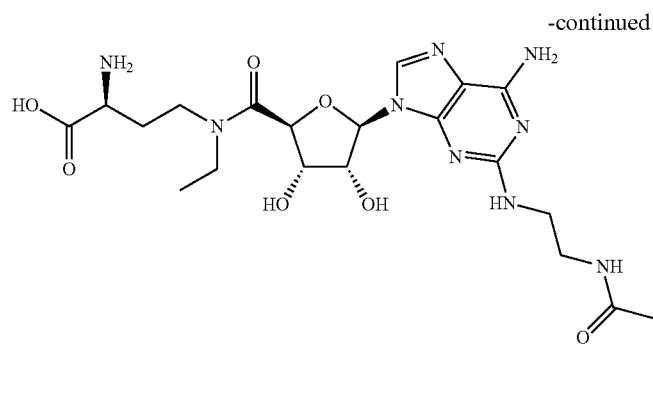
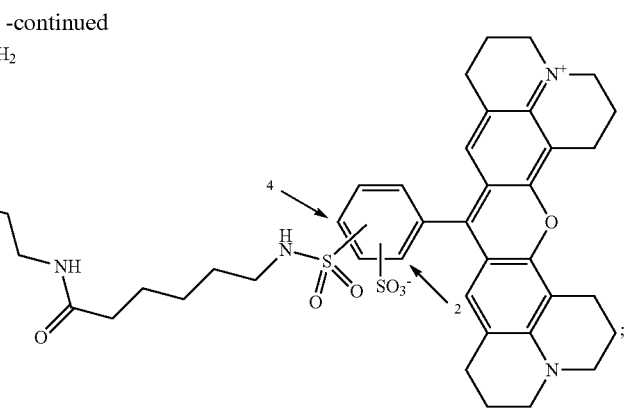

Aza-adenosine Probe 10

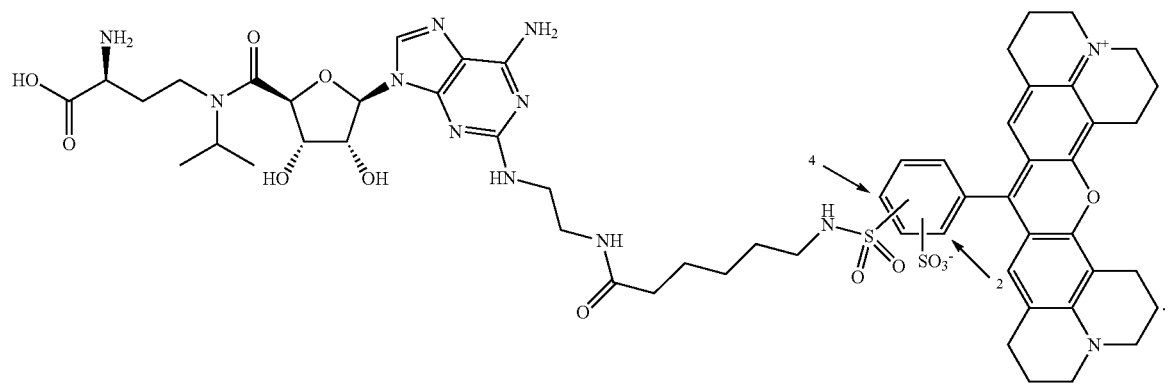

Aza-adenosine Probe 11

7. A fluorescent detection analyte selected from the group consisting of Aza-adenosine Probe 2, Aza-adenosine Probe 4, Aza-adenosine Probe 12, Aza-adenosine Probe 13, Aza-adenosine Probe 14, Aza-adenosine Probe 15, Aza-adenosine Probe 16, Aza-adenosine Probe 17, Aza-adenosine Probe 18, Aza-adenosine Probe 19, Aza-adenosine Probe 20, and Aza-adenosine Probe 21, each respectively illustrated blow:

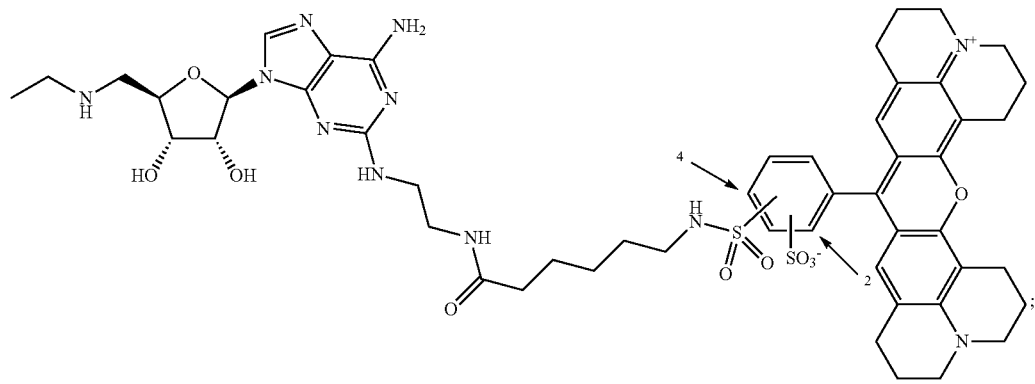

Aza-adenosine Probe 2 (Compound 22A-iv)

-continued
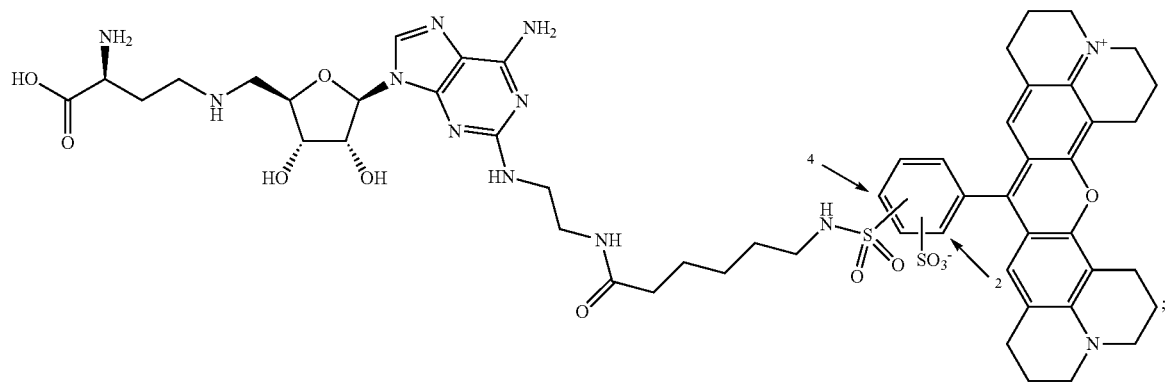
Aza-adenosine Probe 4 (Compound 22B-iv)
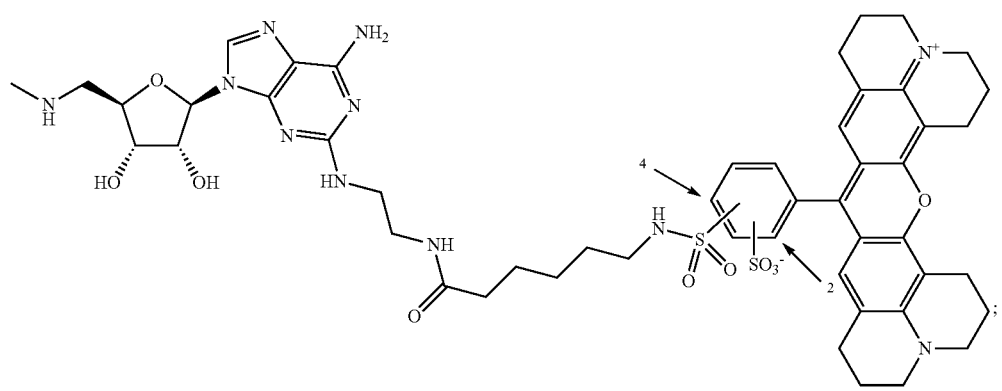
Aza-adenosine Probe 12
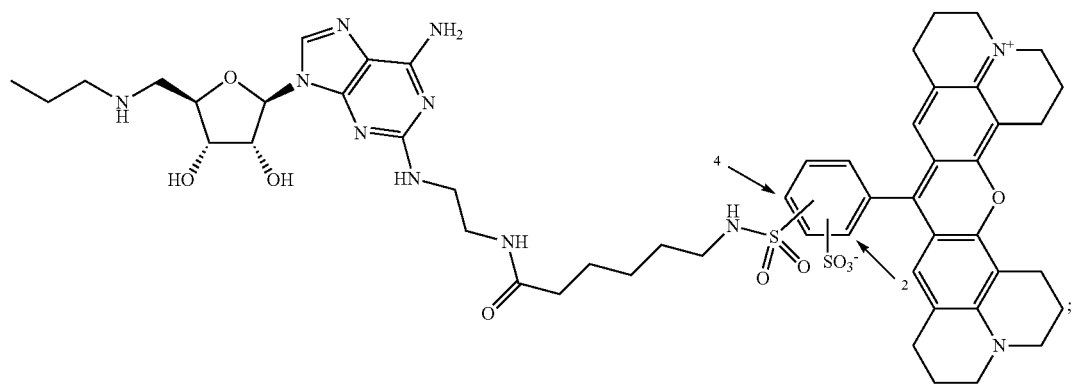
Aza-adenosine Probe 13

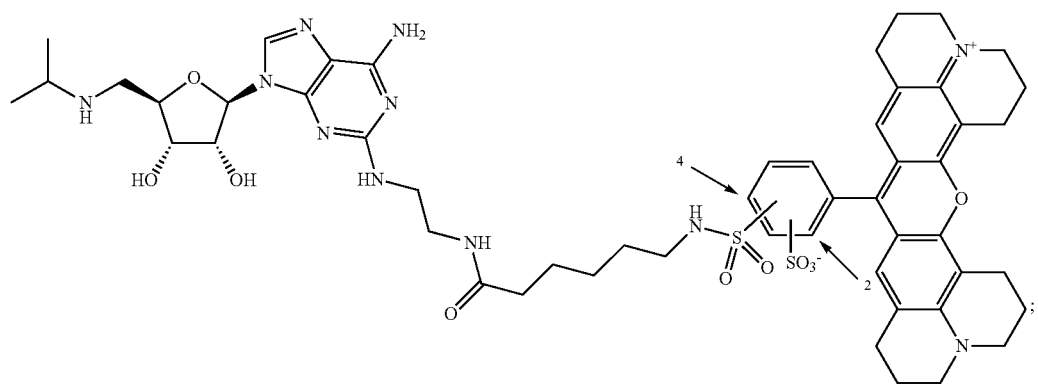
Aza-adenosine Probe 14
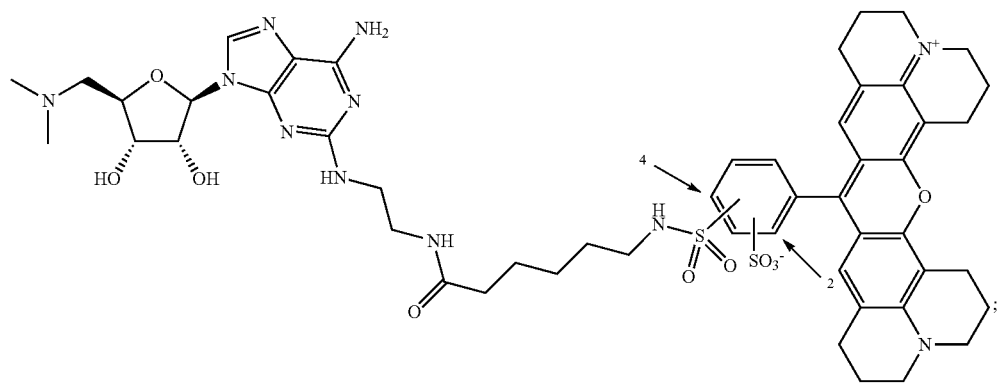
Aza-adenosine Probe 15
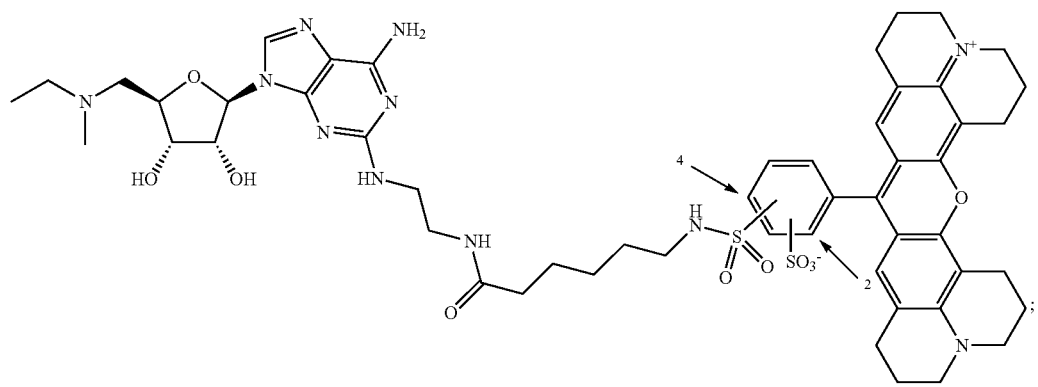
Aza-adenosine Probe 16

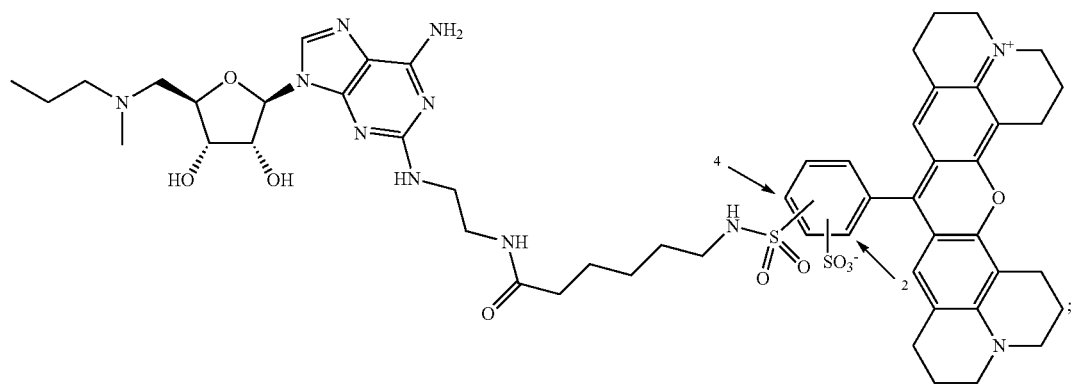
Aza-adenosine Probe 17
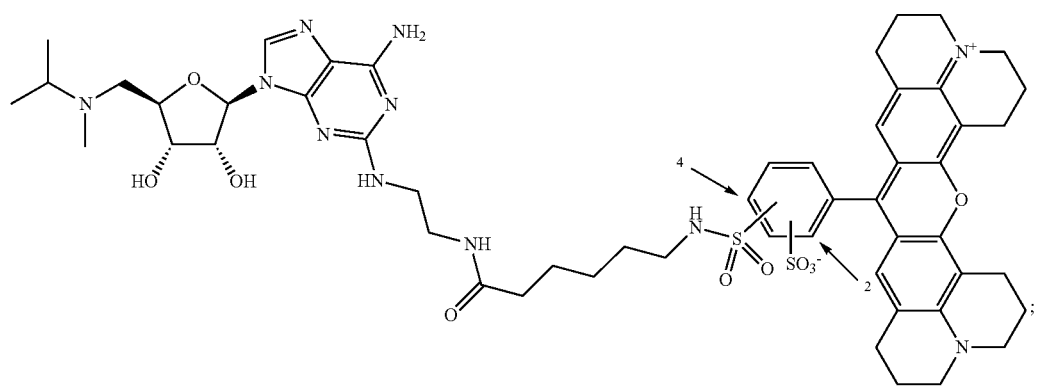
Aza-adenosine Probe 18
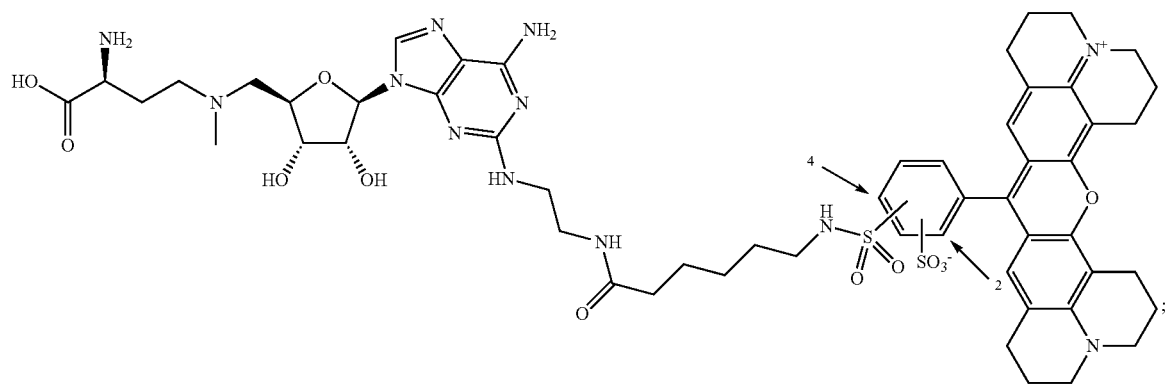
Aza-adenosine Probe 19

-continued
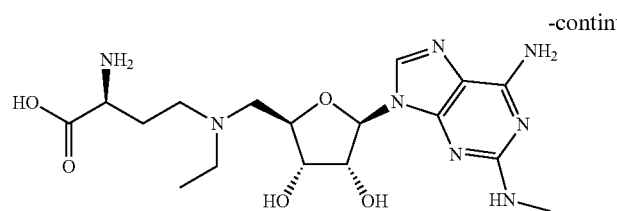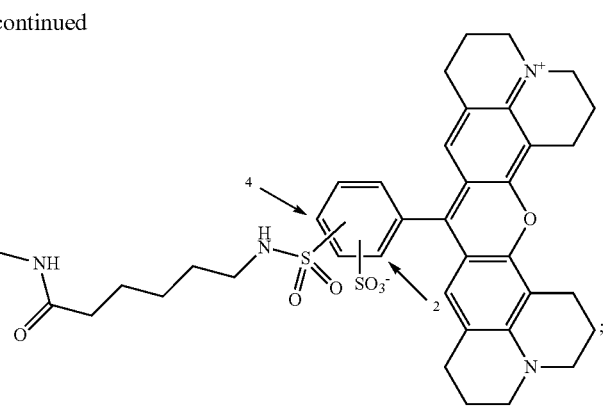
Aza-adenosine Probe 20
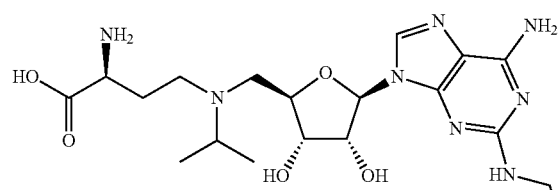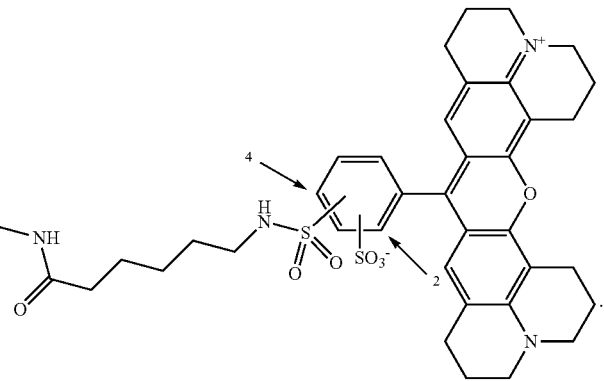
Aza-adenosine Probe 21
* * * * *